(12) United States Patent
Kondo et al.

(10) Patent No.: US 10,539,578 B2
(45) Date of Patent: Jan. 21, 2020

(54) METHOD FOR DIAGNOSING, TREATING, OR PREVENTING MOOD DISORDERS

(71) Applicants: JAPAN TOBACCO INC., Tokyo (JP); VIRUS IKAGAKU KENKYUSHO INC., Toyonaka-shi, Osaka (JP)

(72) Inventors: Kazuhiro Kondo, Tokyo (JP); Nobuyuki Kobayashi, Tokyo (JP); Naomi Oka, Tokyo (JP)

(73) Assignees: JAPAN TOBACCO INC., Tokyo (JP); VIRUS IKAGAKU KENKYUSHO INC., Toyonaka-Shi (JP)

(*) Notice: Subject to any disclaimer, the term of this patent is extended or adjusted under 35 U.S.C. 154(b) by 0 days.

(21) Appl. No.: 16/066,259

(22) PCT Filed: Dec. 28, 2016

(86) PCT No.: PCT/JP2016/089235
§ 371 (c)(1),
(2) Date: Jun. 26, 2018

(87) PCT Pub. No.: WO2017/115878
PCT Pub. Date: Jul. 6, 2017

(65) Prior Publication Data
US 2019/0018022 A1 Jan. 17, 2019

Related U.S. Application Data

(60) Provisional application No. 62/271,579, filed on Dec. 28, 2015.

(51) Int. Cl.
*G01N 33/68* (2006.01)
*G01N 33/541* (2006.01)
*G01N 33/543* (2006.01)

(52) U.S. Cl.
CPC ....... *G01N 33/6896* (2013.01); *G01N 33/541* (2013.01); *G01N 33/54306* (2013.01); *G01N 33/6857* (2013.01); *G01N 2333/03* (2013.01); *G01N 2469/20* (2013.01); *G01N 2800/304* (2013.01); *G01N 2800/50* (2013.01); *G01N 2800/60* (2013.01)

(58) Field of Classification Search
CPC ...... A61K 9/0043; A61K 35/76; A61K 51/08; A61K 9/00; A61K 9/0073; A61K 9/12; C12N 2710/16122; C12N 2710/16222; C12N 15/09; C12N 5/10; C12Q 2600/118; G01N 2800/14; G01N 33/5058; G01N 33/6896; G01N 33/54306; G01N 33/541; G01N 2800/60; G01N 2800/50; G01N 2800/304; G01N 2469/20; G01N 2333/03; G01N 33/6857; G01N 33/531; G01N 33/53; C07K 19/00
See application file for complete search history.

(56) References Cited

U.S. PATENT DOCUMENTS

| | | |
|---|---|---|
| 5,001,049 A | 3/1991 | Klein et al. |
| 7,972,804 B2 | 7/2011 | Lee et al. |
| 8,343,727 B2 | 1/2013 | Takakura et al. |
| 8,431,352 B2 | 4/2013 | Kondo et al. |
| 8,642,045 B2 | 2/2014 | Konda |
| 9,139,617 B2 | 9/2015 | Takakura et al. |
| 2006/0034855 A1 | 2/2006 | Solomon |
| 2008/0176340 A1 | 7/2008 | Soldo et al. |
| 2008/0227111 A1 | 9/2008 | Ichii et al. |
| 2008/0280283 A1 | 11/2008 | Kondo |
| 2009/0068253 A1 | 3/2009 | Guilford |
| 2010/0247486 A1 | 9/2010 | Kondo |
| 2010/0281150 A1 | 11/2010 | Kondo et al. |
| 2010/0281550 A1 | 11/2010 | Kondo et al. |
| 2010/0311076 A1 | 12/2010 | Takakura et al. |
| 2011/0020789 A1 | 1/2011 | Kondo |
| 2011/0053145 A1 | 3/2011 | Takakura et al. |
| 2011/0166106 A1 | 7/2011 | Marschall et al. |
| 2012/0064543 A1 | 3/2012 | Kakakura et al. |
| 2012/0107842 A1 | 5/2012 | Takakura et al. |
| 2012/0269824 A1 | 10/2012 | Varnum et al. |
| 2013/0137088 A1* | 5/2013 | Kondo ............... C07K 14/005 435/5 |
| 2013/0217044 A1 | 8/2013 | Kondo et al. |
| 2016/0068918 A1 | 3/2016 | Kondo |
| 2017/0138957 A1 | 5/2017 | Kondo et al. |
| 2017/0190745 A1 | 7/2017 | Kondo et al. |

FOREIGN PATENT DOCUMENTS

| | | |
|---|---|---|
| EP | 0615750 A2 | 9/1994 |
| EP | 2199391 A1 | 6/2010 |
| EP | 2405268 A1 | 1/2012 |

(Continued)

OTHER PUBLICATIONS

Liljeroos L, Malito E, Ferlenghi I, Bottomley MJ. Structural and Computational Biology in the Design of Immunogenic Vaccine Antigens. J Immunol Res. 2015;2015:156241. Epub Oct. 7, 2015.*

(Continued)

*Primary Examiner* — Rachel B Gill

(74) *Attorney, Agent, or Firm* — Birch, Stewart, Kolasch & Birch, LLP

(57) ABSTRACT

An embodiment of the present invention provides a novel method for diagnosing, treating, or preventing a mood disorder. The method includes the step of measuring, by using a fusion protein, a level of the anti-fusion protein antibody in a biological sample.

10 Claims, 16 Drawing Sheets
(14 of 16 Drawing Sheet(s) Filed in Color)
Specification includes a Sequence Listing.

(56) References Cited

FOREIGN PATENT DOCUMENTS

| EP | 2416158 A1 | 2/2012 |
|---|---|---|
| JP | 2-233697 A | 9/1990 |
| JP | 8-43392 A | 2/1996 |
| JP | 11-196870 A | 7/1999 |
| JP | 2004-301646 A | 10/2004 |
| JP | 2008-261841 A | 10/2008 |
| JP | 4218842 B2 | 2/2009 |
| JP | 4920084 B2 | 4/2012 |
| JP | 2012-110329 A | 6/2012 |
| JP | 2013-150553 A | 8/2013 |
| JP | 2013-181034 A | 9/2013 |
| JP | 2014-19658 A | 2/2014 |
| WO | WO 2006/006634 A1 | 1/2006 |
| WO | WO 2009/028625 A1 | 3/2009 |
| WO | WO 2009/041501 A1 | 4/2009 |
| WO | WO 2010/101157 A1 | 9/2010 |
| WO | WO 2010/114029 A1 | 10/2010 |
| WO | WO 2015/199247 A1 | 12/2015 |

OTHER PUBLICATIONS

Reddy Chichili VP, Kumar V, Sivaraman J. Linkers in the structural biology of protein-protein interactions. Protein Sci. Feb. 2013;22(2):153-67. Epub Jan. 8, 2013.*

Gizurarson S. Anatomical and histological factors affecting intranasal drug and vaccine delivery. Curr Drug Deliv. Nov. 2012;9(6):566-82.*

Reynaud JM, Horvat B. Animal models for human herpesvirus 6 infection. Front Microbiol. Jul. 4, 2013;4:174.*

Donati et al., "Variant-Specific Tropism of Human Herpesvirus 6 in Human Astrocytes," Journal of Virology (Aug. 2005), vol. 79, No. 15, pp. 9439-9448.

English translation of International Preliminary Report on Patentability and Written Opinion dated Jul. 12, 2018, in PCT International Application No. PCT/JP2016/089235 (Forms PCT/IB/338, PCT/IB/373 and PCT/ISA/237).

English translation of International Search Report dated Feb. 7, 2017, in PCT International Application No. PCT/JP2016/089235.

Kondo et al., "Association of Human Herpesvirus 6 Infection of the Central Nervous System with Recurrence of Febrile Convulsions," The Journal of Infectious Diseases (1993), vol. 167, pp. 1197-1200.

Tuke et al., "Distribution and quantification of human herpesvirus 6 in multiple sclerosis and control brains," Multiple Sclerosis (2004), vol. 10, pp. 355-359.

Yamamoto, Y. and T. Sakisaka, "Molecular Machinery for Insertion of Tail-Anchored Membrane Proteins into the Endoplasmic Reticulum Membrane in Mammalian Cells," Molecular Cell (Nov. 9, 2012), vol. 48, pp. 387-397.

Dominguez et al., "Human Herpesvirus 6B Genome Sequence: Coding with Human Herpesvirus 6A," Journal of Virology, vol 73, No. 10, Oct. 1999, pp. 8040-8052.

Extended European Search Report for Application No. 08833887.6 dated Dec. 21, 2010.

Extended European Search Report dated May 3, 2012, in European Patent Application No. 10758800.6.

Eymard et al., "Human herpesvirus 6 and chronic fatigue syndrome," Canadian Journal of Infectious Diseases, vol. 4, No. 4, Jul./Aug. 1993, pp. 199-202.

GENBANK, Accession No. U92288.1, Nucleotide Database, Oct. 7, 2005, http://www.ncbi.nlm.nih.gov/nuccore/U92288.1, 12 pages provided.

International Search Report dated Jun. 29, 2010, in International Application No. PCT/JP2010/055884.

International Search Report dated Oct. 28, 2008 for International Application No. PCT/JP2008/067300.

Japanese Office Action issued in Japanese Patent Application No. 2013-063090 dated Sep. 2, 2014.

Kobayashi et al., "Hito Herpesvirus (HHV)-6 Senpuku Kansen Tokuiteki Tanpaku ni yoru Utsu Shojo no Hassho Kijo," Dai 55 Kai The Japanese Society of Virology Gakujutsu Shukai Program. Shorokushu, Oct. 1, 2007, p. 120.

Kogelnik et al., "Use of valganciclovir in patients with elevated antibody titers against Human Herpesvirus-6 (HHV-6) and Epstein-Barr Virus (EBV) who were experiencing central nervous system dysfunction including long-standing fatigue", J. of Clinical Virology, vol. 37, Suppl. 1, 2006, pp. S33-S38.

Kondo et al., "Recognition of a Novel Stage of Betaherpesvirus Latency in Human Herpesvirus 6," Journal of Virology, vol. 77, No. 3, Feb. 2003, pp. 2258-2264.

Kondo et al., "Detection of a Gene Cluster that is Dispensible for Human Herpesvirus 6 Replication and Latency," Journal of Virology, vol. 77, No. 19, Oct. 2003, pp. 10719-10724.

Kondo et al., "Identification of Human Herpesvirus 6 Latency-Associated Transcripts," Journal of Virology, vol. 76, No. 8, Apr. 2002, pp. 4145-4151.

Kondo et al., Latent human herpesvirus 6 infection of human monocytes/macrophages, Journal of General Virology, vol. 72, 1991, pp. 1401-1408.

Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2006, 03, Heisei 17 Nendo Sokatsu • Buntan Kenkyu Hokokusho. pp. 19-23.

Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2007, 03, Heisei 18 Nendo Sokatsu • Buntan Kenkyu Hokokusho, pp. 13-18.

Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2008. 03, Heisei 19 Nendo Sokatsu • Buntan Kenkyu Hokokusho, pp. 17-23.

Kondo et al., "Identification of a novel HHV-6 latent-protein associated with CFS and mood disorders", Neuroscience Research, vol. 68S, 2010, p. e51, XP002609007.

Kondo, "Herpesvirus Kansen to Hiro," Virus, vol. 55, No. 1, 2005, pp. 9-17.

Kondo, "Hito Herpesvirus 6 (HHV-6) to CFS," Prog. Med., vol. 25, 2005, pp. 1315-1319.

Kondo, "Human herpesvirus latency and fatigue," Virus, vol. 55, No. 1, 2005, pp. 9-18, with English abstract.

Kondo, "Virus no Senpuku Kansen Tanpakushitsu to Hiro," Molecular Medicine, vol. 41, No. 10, 2004, pp. 1216-1221.

Mirandola et al., "Temporal Mapping of Transcripts in Herpesvirus 6 Variants", Journal of Virology, vol. 72, No. 5, 1998, pp. 3837-3844.

NCBI Database, "Human herpesvirus 6B, complete genome," Reference Sequence: NC_000898.1, Apr. 5, 2007, pp. 1-61.

New Zealand Office Action for Application No. 599590 dated Aug. 22, 2013.

Patnaik et al., "Prevalence of IgM Antibodies to Human Herpesvirus 6 Early Antigen (p41/38) in Patients with Chronic Fatigue Syndrome", The Journal of Infectious Diseases, vol. 172, 1995, pp. 1364-1367, XP002609186.

Reeves et al., "Human Herpesviruses 6 and 7 in Chronic Fatigue Syndrome: A Case-Control Study", Clinical Infectious Diseases, vol. 31, 2000, pp. 48-52, XP002609184.

U.S. Office Action issued in U.S. Appl. No. 13/756,858 dated May 19, 2015.

Wallace et al., "Human Herpesviruses in Chronic Fatigue Syndrome", Clinical and Diagnostic Laboratory Immunology, vol. 6, No. 2, Mar. 1999, pp. 216-223, XP002609185.

English tranlsation of International Preliminary Report on Patentability and Written Opinion dated Jan. 5, 2017, in International Application No. PCT/JP2015/069080.

Extended European Search Report, dated Nov. 24, 2017, for European Application No. 15811939.6.

Harberts et al., "Human herpesvirus-6 entry into the central nervous system through the olfactory pathway," PNAS, vol. 108, No. 33, Aug. 16, 2011, pp. 13734-13739.

HHV-6 Foundation, "HHV-6 & Chronic Fatigue Syndrome (CFS/ME)," https://hhv-6foundation.org, Jul. 10, 2013, 9 pages.

HHV-6 Foundation, "HHV-6A can travel through the nose to the brain," https://hhv-6foundation.org, Aug. 9, 2011, 6 pages.

(56) References Cited

OTHER PUBLICATIONS

International Search Report dated Sep. 29, 2015, in International Application No. PCT/JP2015/069080.
Johnson, "The Symposium on Viruses in Chronic Fatigue Syndrome (ME/CFS)(May 2008): Part I," Phoenix Rising, Mar. 6, 2011, pp. 1-6.
Kalinke et al., "Host strategies against virus entry via the olfactory system," Virulence, vol. 2, No. 4, Jul./Aug. 2011, pp. 367-370 (5 pages).
Kobayashi et al., "Identification of Novel HHV-6 Latent Protein Associated with Mood Disorders in CFS, Depressive Disorder, Bipolar Disorder and HHV-6 Encephalopathy," 6th International Conference on HHV-6 & 7, Baltimore, Maryland, USA, Jun. 22, 2008, 1 page (abstract only).
Milho et al., "A Heparan-Dependent Herpesvirus Targets the Olfactory Neuroepithelium for Host Entry," PLOS Pathogens, vol. 8, Issue 11, e1002986, Nov. 2012, pp. 1-15.
Phoenix Rising, "Whatever happened to . . . research on SITH-1 protein made by HHV-6 in ME/CFS patients," http://forums.phoenixrising.me, Apr. 3, 2018, pp. 1-6.
Rudinger, "Characteristics of the amino acids as components of a peptide hormone sequence", Peptide Hormones (ed. J.A. Parsons), University Park Press, Baltimore, MD, 1976, pp. 1-7.
Sanders, "Common virus may ride up nose to brain," Science News, Aug. 8, 2011, p. 1-2.
U.S. Advisory Action for U.S. Appl. No. 12/679,816, dated Aug. 7, 2012.
U.S. Advisory Action for U.S. Appl. No. 15/462,031, dated Jun. 26, 2018.
U.S. Advisory Action dated Jan. 19, 2017, in U.S. Appl. No. 13/756,858.
U.S. Notice of Allowance for U.S. Appl. No. 12/679,816, dated Oct. 3, 2012.
U.S. Notice of Allowance for U.S. Appl. No. 12/679,816, dated Feb. 21, 2013.
U.S. Notice of Allowance for U.S. Appl. No. 13/257,754, dated May 13, 2015.
U.S. Notice of Allowance for U.S. Appl. No. 15/321,884, dated Apr. 19, 2018.
U.S. Office Action dated Mar. 30, 2018, for U.S. Appl. No. 13/756,858.
U.S. Office Action dated Sep. 20, 2017, for U.S. Appl. No. 13/756,858.
U.S. Office Action for U.S. Appl. No. 12/679,816, dated Jul. 21, 2011.
U.S. Office Action for U.S. Appl. No. 12/679,816, dated Mar. 12, 2012.
U.S. Office Action for U.S. Appl. No. 13/257,754, dated Jun. 12, 2014.
U.S. Office Action for U.S. Appl. No. 13/257,754, dated Nov. 19, 2014.
U.S. Office Action for U.S. Appl. No. 13/756,858, dated Mar. 22, 2017.
U.S. Office Action for U.S. Appl. No. 13/756,858, dated Nov. 27, 2018.
U.S. Office Action for U.S. Appl. No. 13/756,858, dated Oct. 24, 2016.
U.S. Office Action for U.S. Appl. No. 15/321,884, dated Mar. 15, 2017.
U.S. Office Action for U.S. Appl. No. 15/321,884, dated Oct. 20, 2017.
U.S. Office Action for U.S. Appl. No. 15/462,031, dated Dec. 14, 2018.
U.S. Office Action for U.S. Appl. No. 15/462,031, dated Jan. 29, 2018.
U.S. Office Action for U.S. Appl. No. 15/462,031, dated Jun. 28, 2017.
U.S. Office Action issued in U.S. Appl. No. 13/732,981 dated Oct. 21, 2016.
U.S. Office Action issued in U.S. Appl. No. 13/756,858 dated Oct. 23, 2015.
U.S. Office Action, dated Apr. 21, 2016, for U.S. Appl. No. 13/732,981.
U.S. Office Action, dated Feb. 8, 2016, for U.S. Appl. No. 13/756,858.
Wen, "Olfactory Targeting Through Intranasal Delivery of Biopharmaceutical Drugs to the Brain—Current Development," Discovery Medicine, Jun. 13, 2011, pp. 1-8.

* cited by examiner

SITH-1(FOR IFA)

SITH-1(FOR ELISA)

SITH-CAML
(FOR IFA, ELISA)

CAML-SITH
(FOR IFA, ELISA)

CAML(FOR IFA)

CAML(FOR ELISA)

CAML

SITH-1

SITH-CAML

CAML-SITH

LITMUS28i

HEALTHY INDIVIDUAL 1

HEALTHY INDIVIDUAL 2

SUPPRESSION OF SITH-1 EXPRESSION BY GANCICLOVIR

METHOD FOR DIAGNOSING, TREATING, OR PREVENTING MOOD DISORDERS

CROSS REFERENCE TO RELATED APPLICATIONS

This application is the National Phase of PCT International Application No. PCT/JP2016/089235, filed on Dec. 28, 2016, which claims priority under 35 U.S.C. 119(e) to U.S. Provisional Application No. 62/271,579, filed on Dec. 28, 2015, all of which are hereby expressly incorporated by reference into the present application.

TECHNICAL FIELD

The present invention relates to a method for diagnosing or treating a mood disorder. Specifically, the present invention relates to a novel method for diagnosing, treating, or preventing a mood disorder by using, as an index(es), a level(s) of an antibody (or antibodies each) recognizing a fusion protein of a certain protein.

BACKGROUND ART

A mood disorder, which is a mental disorder typified by depression and bipolar disorder, is recently becoming more prevalent and is becoming a major social problem. A mood disorder is basically treated by pharmacotherapy in which a tricyclic antidepressant, a selective serotonin reuptake inhibitor (SSRI), a serotonin and norepinephrine reuptake inhibitor (SNRI), and/or the like is/are used.

Human herpesvirus-6 (HHV-6) is a virus found in the peripheral blood of an AIDS patient, and belongs to a herpesvirus 13 subfamily. HHV-6 has two variants: HHV-6 variant A (HHV-6A) and HHV-6 variant B (HHV-6B). Most humans are initially infected by HHV-6B during infancy, and roseola infantum occurs at development of infection. At an acute stage of initial infection, HHV-6B is highly likely to invade into a brain and latently infect the brain. The latent infection remains even after an infected person becomes an adult (Non-Patent Literature 1). Latent infection means an infection state in which a virus remains in a host cell without producing infectious viral particles. It is suggested that in a brain, mainly glial cells of a frontal lobe, a hippocampal region, and the like contract HHV-6B latent infection (Non-Patent Literatures 2 and 3). In addition, macrophages in peripheral blood also suffer HHV-6 latent infection, and fatigue developed by daily living or the like causes the HHV-6 to be reactivated and released into saliva (Patent Literature 1).

During latent infection with HHV-6, no virus is produced. It is known, however, that there exists an "intermediate stage" which is a relatively stable stage and in which genes are actively expressed. As a protein expressed in an intermediate stage, (Small protein encoded by the Intermediate stage Transcript of HHV-6)-1 (hereinafter referred to as "SITH-1") is identified (Patent Literature 2). Since an antibody against SITH-1 is detected specifically in a patient of a mood disorder such as depression, a method for diagnosing a mood disorder has been developed, which method includes detecting and measuring an anti-SITH-1 antibody in a specimen from a human subject (Patent Literature 2). It was also disclosed that in a case where a SITH-1 gene, which was linked to a glial cell-specific expression promoter, was introduced into the brain of a mouse with use of an adenovirus vector and was expressed, the mouse exhibited behavioral abnormalities such as those caused by a mental disorder (Patent Literature 2).

Calcium-signal modulating cyclophilin ligand (CAML) is originally isolated as an endoplasmic reticulum membrane protein that regulates T cell receptor signaling. CAML is subsequently found to function as a TRC40 receptor in an endoplasmic reticulum membrane (Non-Patent Literature 4). It has been known that CAML is strongly expressed in lymphocytes and in a brain, and has a function to increase an intracellular calcium concentration when strongly bound to SITH-1 in a cell (Patent Literature 2).

CITATION LIST

Patent Literatures

[Patent Literature 1] PCT International Publication No. WO 2006-006634 A1 (Publication Date: Jan. 19, 2006)
[Patent Literature 2] PCT International Publication No. WO 2009-041501 A1 (Publication Date: Apr. 2, 2009)
[Patent Literature 3] PCT International Publication No. WO 2015-199247 A1 Publication Date: Dec. 30, 2015

Non-Patent Literatures

[Non-Patent Literature 1] Kondo K et al., J infect Dis, 167: 1197-1200, 1993
[Non-Patent Literature 2] Tuke et al., Multiple Sclerosis, 10: 355-359, 2004
[Non-Patent Literature 3] Donati et al., Journal of Virology Vol. 79, No. 15: 9439-9448, 2005
[Non-Patent Literature 4] Yamamoto. et al., Molecular Cell, 48, 387-397 (2012)

SUMMARY OF INVENTION

Technical Problem

The mechanism of development of a mood disorder has not been sufficiently understood yet. In regard to diagnosis and treatment of mood disorder, in particular, there are demands for further development of methods of diagnosing and treating a mood disorder. Under the circumstances, an object of an embodiment of the present invention is to provide a novel method for diagnosing and/or treating a mood disorder, which method is superior to conventional techniques.

Solution to Problem

In order to attain the above object, the inventors of the present invention conducted diligent studies on a method for diagnosing a mood disorder. As a result, the inventors of the present invention have found that: (a) measurement of a level of an antibody recognizing a fusion protein of a certain protein, in a biological sample, makes it possible not only to determine whether or not a human subject has a mood disorder but also to assess/evaluate risk (degree of risk) of developing a target disorder in the human subject; and (b) the method of an embodiment of the present invention has a remarkably improved detection sensitivity as compared to a conventional method.

Consequently, the inventors have accomplished the present invention. The present invention may encompass the following invention group.

(1) A fusion protein including a SITH-1 protein and a CAML protein.

(2) A method for producing a soluble conjugate of a SITH-1 protein and a CAML protein, the method including the step of obtaining a soluble fusion protein by fusion of the SITH-1 protein and the CAML protein.

(3) A diagnosis method for a mood disorder, including the steps of: measuring an anti-SITH-1 antibody level in a biological sample isolated from a human subject; and measuring an anti-CAML antibody level in the biological sample.

Advantageous Effects of Invention

An embodiment of the present invention advantageously makes it possible to provide a novel method for diagnosing or treating a mood disorder.

BRIEF DESCRIPTION OF DRAWINGS

The patent or application file contains at least one color drawing. Copies of this patent or patent application publication with color drawing will be provided by the USPTO upon request and payment of the necessary fee.

Figure 20:
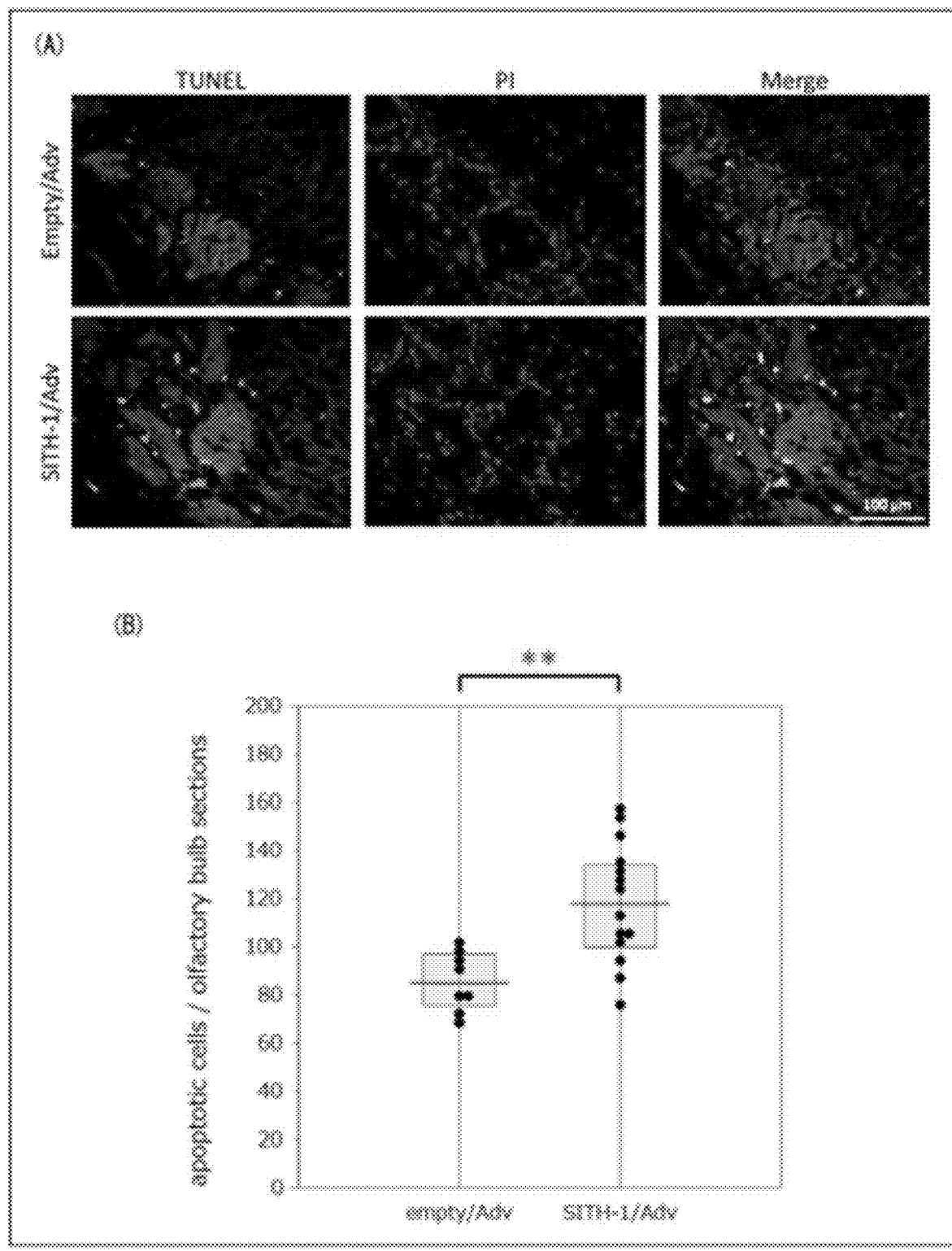
FIG. 20 shows the results of TUNEL staining of olfactory bulbs, in accordance with Example 7 of the present invention.

(A) of FIG. 20 is a view showing TUNEL stained images of olfactory bulbs of empty/Adv nasal administration mice and SITH-1/Adv nasal administration mice. (B) of FIG. 20 is a view showing the results of counting the number of cells positive for TUNEL staining of olfactory bulbs.

Figure 21:
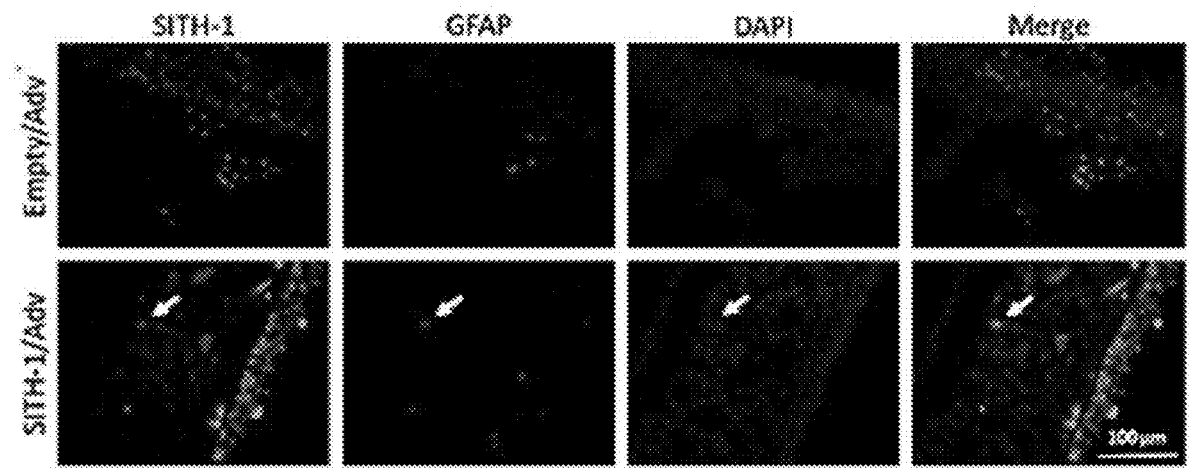

FIG. 21 shows the results of immunohistological staining of olfactory epithelia by an anti-SITH-1 antibody, in accordance with Example 7 of the present invention. FIG. 21 shows immunohistologically stained images of olfactory epithelium cells of empty/Adv nasal administration mice and SITH-1/Adv nasal administration mice.

Figure 22:
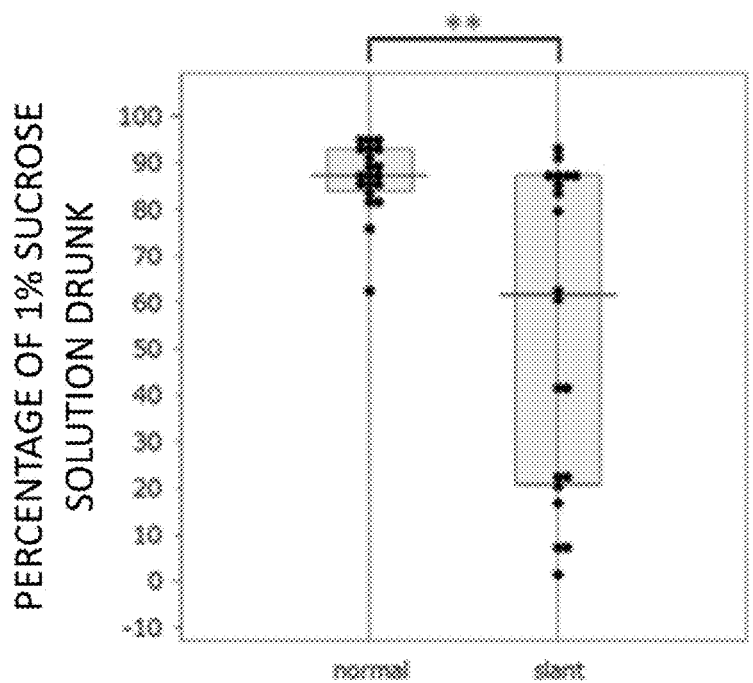

FIG. 22 shows the results of a stress vulnerability test of SITH-1/Adv nasal administration mice, in accordance with Example 7 of the present invention.

Figure 23:
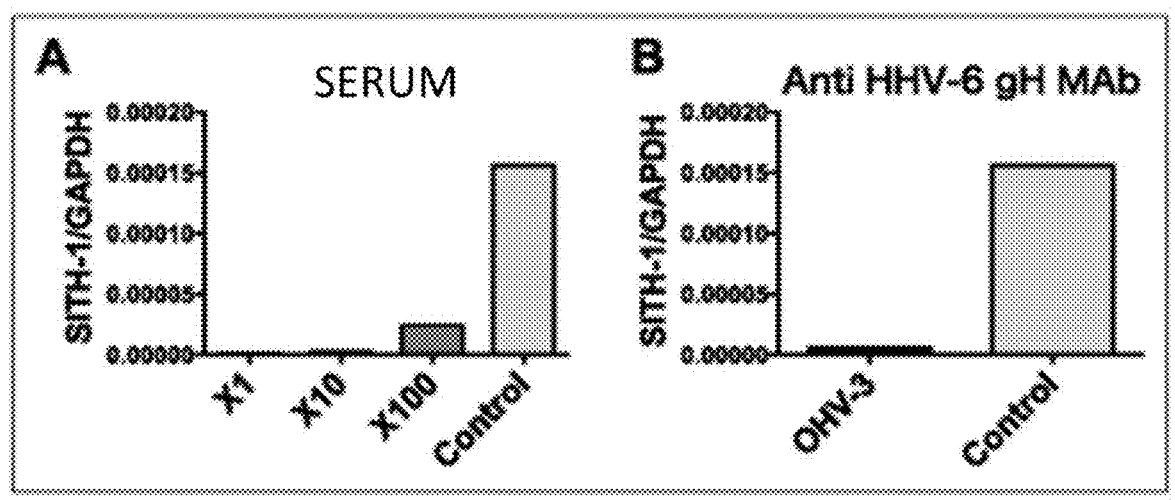

FIG. 23 shows the results of SITH-1 expression of HHV-6-infected U373, in accordance with Example 7 of the present invention.

Figure 24:
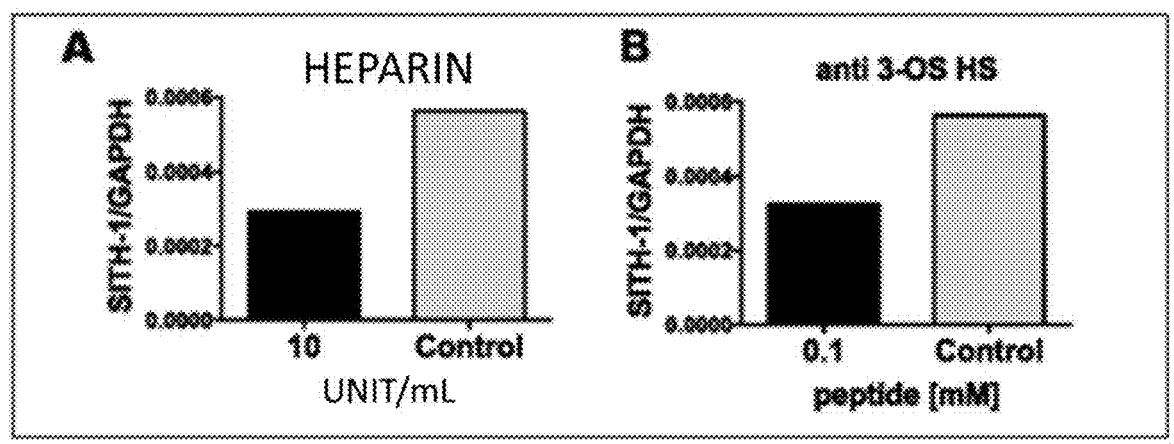

FIG. 24 shows the results of SITH-1 expression of HHV-6-infected U373, in accordance with Example 7 of the present invention.

Figure 25:
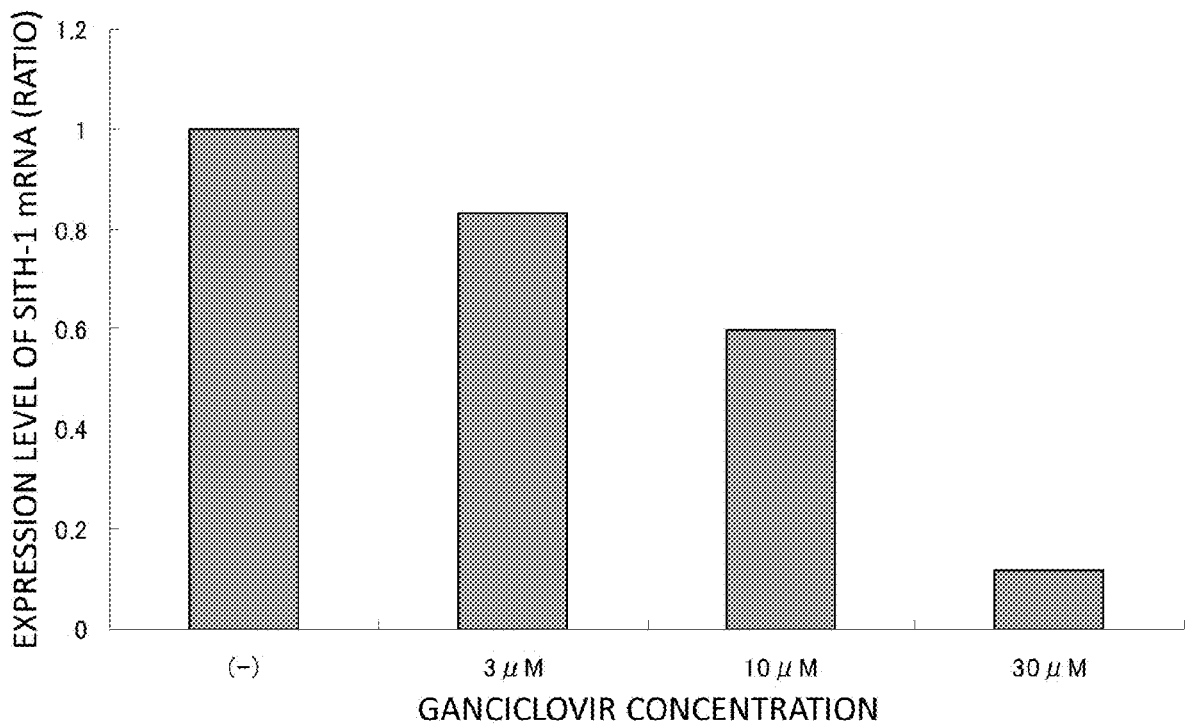

FIG. 25 illustrates suppression of SITH-1 expression by ganciclovir, in accordance with Example 8 of the present invention.

Figure 26:
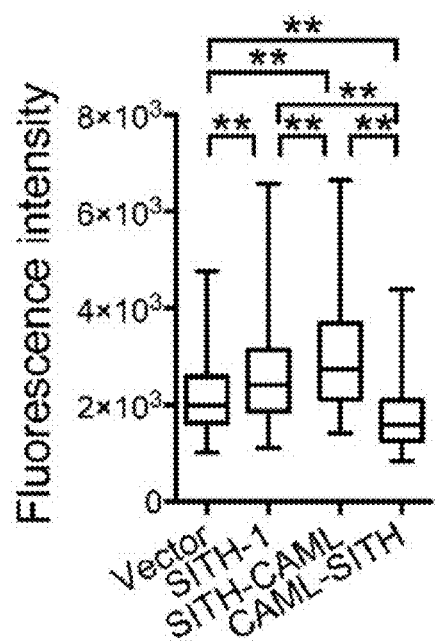

FIG. 26 indicates the effects of SITH-1 expression and expression of fusion proteins on intracellular calcium concentration, in accordance with Example 9 of the present invention.

Figure 27:
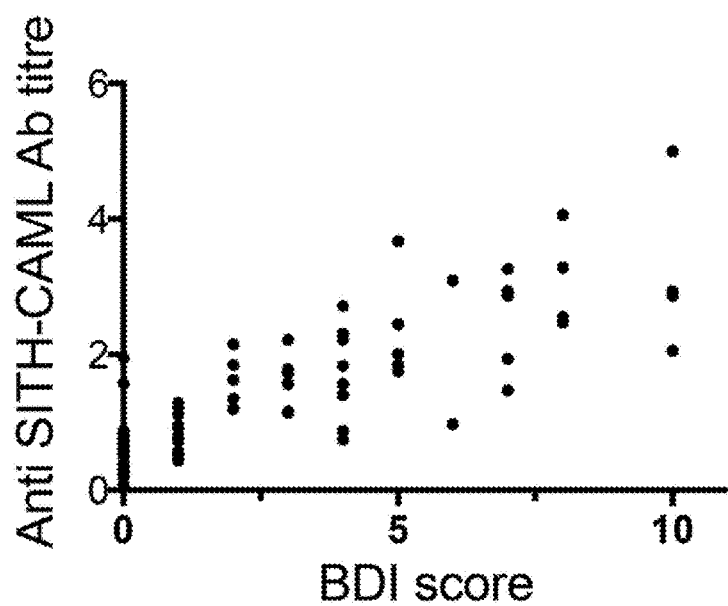

FIG. 27 illustrates a correlation between antibody titer of an anti-S-C antibody in healthy subject serum and BDI score, in accordance with Example 10 of the present invention.

DESCRIPTION OF EMBODIMENTS

The following description will discuss an embodiment of the present invention in detail. Note that all of the academic documents and patent literatures listed herein are incorporated by reference herein. Unless otherwise specified herein, "A to B" which indicates a numerical range means "equal to or greater than A and equal to or less than B".

Explanation of Terms

As used herein, the term "protein" is interchangeable with the term "polypeptide". A "protein" includes a structure of amino acids linked to each other by a peptide bond. A "protein" may further include a structure of a sugar chain, an isoprenoid group or the like. The term "protein", unless otherwise specified, includes in its scope a polypeptide that contains a known analog of a naturally occurring amino acid capable of functioning similarly to the naturally occurring amino acid.

In an embodiment of the present invention, the phrase "one or several amino acids are substituted, deleted, inserted and/or added" means a substitution, deletion, insertion, and/or addition of such a number of amino acids (preferably 10 or less, 7 or less, 5 or less, 4 or less, 3 or less, 2 or less, even more preferably 1 or less) that can be substituted, deleted, inserted, and/or added by a conventionally-known method for preparation of a mutant peptide, such as site-directed mutagenesis. An amino acid residue to be substituted is preferably substituted by another amino acid in which a property of a side chain of the amino acid residue is preserved. Examples of the property of the side chain of the amino acid encompass hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxyl group-containing side chain (S, T, Y), amino acids having a sulfur atom-containing side chain (C, M), amino acids having a carboxylic acid and amide-containing side chain (D, N, E, Q), amino acids having a base-containing side chain (R, K, H), and amino acids having an aromatic group-containing side chain (H, F, Y, W). Further, it is also known that amino acids are classified by, for example, the mutational matrix (Taylor 1986, J, Theor. Biol. 119, 205-218; Sambrook, J. et al., Molecular Cloning 3rd ed. A7.6-A7.9, Cold Spring Harbor Lab. Press, 2001). Briefly, this classification is as follows: Aliphatic amino acids (L, I, V), aromatic amino acids (H, W, Y, F), charged amino acids (D, E, R, K, H), positively charged amino acids (R, K, H), negatively charged amino acids (D, E), hydrophobic amino acids (H, W, Y, F, M, L, I, V, C, A, G, T, K), polar amino acids (T, S, N, D, E, Q, R, K, H, W, Y), small amino acids (P, V, C, A, G, T, S, N, D), micro amino acids (A, G, S), and large (non-small) amino acids (Q, E, R, K, H, W, Y, F, M, L, I). Note that the letters in the above parentheses are each a one letter amino acid code. An amino acid residue to be substituted is preferably substituted by another amino acid belonging to the same classification.

In an embodiment of the present invention, the phrase "amino acid sequence having a high homology" refers to an amino acid sequence for which the whole of the amino acid sequence (or a region of the amino acid sequence which region is necessary to express a function) has a sequence identity, to a target amino acid sequence, of at least 80% or more, preferably 85% or more, more preferably 90% or more, even more preferably 95% or more, 96% or more, 97% or more, 98% or more, 99% or more, or 99.5% or more. The homology of the sequence can be determined by, for example, the BLASTX program (amino acid level) (Altschul et al. J. Mol. Biol., 215: 403-410, 1990). This program is based on the algorithm BLAST by Karlin and Altschul (Proc. Natl. Acad. Sci. USA, 87:2264-2268, 1990, Proc. Natl. Acad. Sci. USA, 90: 5873-5877, 1993). For analysis of an amino acid sequence by the BLASTX program, parameters are set so that score=50 and word length=3, for example. Analysis of an amino acid sequence by the Gapped BLAST program can be carried out as described by Altschul et al. (Nucleic Acids Res. 25: 3389-3402, 1997). For analysis by the BLAST program and the Gapped BLAST program, default parameters of these programs are used. Specific methods for carrying out these analyses are conventionally known. In order to optimally align a compared amino acid sequence, addition or deletion (e.g., a gap) may be allowed.

The term "homology" as used herein refers to a percentage (e.g., homology, positive) of the number of amino acid residues having properties similar to those of the compared amino acid sequence. However, more preferably, the term "homology" is a percentage (identity) of the number of amino acid residues identical to those of the compared amino acid sequence. Note that the properties of the amino acid are as described above.

The term "gene" as used herein is interchangeable with "polynucleotide", "nucleic acid", or "nucleic acid molecule". "Polynucleotide" means a polymer of nucleotides.

Therefore, the term "gene" used herein encompasses not only double stranded DNA but also (i) single stranded DNA, such as a sense strand and an antisense strand, by which double stranded DNA is constituted and (ii) RNA (such as mRNA). An antisense strand can be used as a probe or as an antisense drug.

Examples of the "DNA" encompass cDNA and genomic DNA each of which is obtained by, for example, cloning, a chemical synthesis technique, or a combination of cloning and a chemical synthesis technique. That is, the DNA can be (i) a "genome" DNA that includes a non-coding sequence such as an intron in the form included in the genome of an animal or (ii) cDNA that can be obtained based on mRNA by use of a reverse transcriptase and a polymerase, that is, "transcriptional" DNA that includes no non-coding sequence such as an intron.

Note that the term "nucleic acid" herein encompasses a polynucleotide composed of any simple nucleotides and/or modified nucleotides. Examples of the nucleic acid encompass cDNA, mRNA, total RNA, and hnRNA. Examples of "modified nucleotide" encompass (i) phosphate esters including inosine, acetylcytidine, methylcytidine, methyladenosine, and methylguanosine and (ii) an acquired nucleotide which can occur by the effect of an ultraviolet ray or a chemical substance.

As used herein, the term "nucleotide sequence" is interchangeable with "nucleic acid sequence", and is represented as a sequence of deoxyribonucleotide (which is abbreviated as A, G, C, and T). A polynucleotide or a "nucleotide sequence" of a polynucleotide means (i) a sequence of deoxyribonucleotides with respect to a DNA molecule or the polynucleotide and (ii) a sequence corresponding to ribonucleotides (A, G, C, and U) with respect to an RNA molecule or the polynucleotide (Note that each of thymidine deoxynucleotides (T) in a deoxynucleotide sequence as defined herein is substituted by a uridine (U) of the ribonucleotides.).

In an embodiment of the present invention, "mood disorder" refers to a state in which a continuous change in mood (emotion) for a certain period of time causes a feeling of disturbance and/or interferes with daily living in some manner. Representative examples of the mood disorder are (i) depression, in which only a depressive state is observed as a symptom and (ii) bipolar disorder, in which manic states and depressive states are repeated. Although various causes for mood disorder are considered, many details are unknown. Medically, mood disorders are operationally diagnosed according to diagnostic criteria set by (i) the DSM (Diagnostic and Statistical Manual of Mental Disorders) which is introduced by the American Psychiatric Association or (ii) the ICD (International Statistical Classification of Diseases and Related Health Problems) which is an international standard for diseases. The term mood disorder, as used herein, preferably does not include a temporary depressive state caused by a stressor.

In an embodiment of the present invention, "depressive state" refers to a state in which a patient presents symptoms of depression, regardless of the duration or severity of the symptoms. A symptom of depression is characterized by at least one of the following: sad feelings, discouraged feelings about the future, anxiety about and/or fear of failure, decreased sense of contentment, abnormal feelings of guilt, a sense of being punished, a sense of disappointment in oneself, a feeling of inferiority, suicide attempt, wanting to cry, irritability, loss of interests, blockage of one's thought process and a decreased ability to make decisions, feelings of inferiority regarding one's appearance, psychomotor suppression and a feeling of inability to work, sleeplessness, easy fatigability, decreased appetite, weight loss, anxiety about psychosomatic symptoms and health, and decreased libido. As used herein, the term "depression" indicates, as described above, a type of mood disorder which is diagnosed by the above-described diagnostic criteria.

As used herein, the term "healthy subject" indicates a normal individual who does not have a mood disorder.

In an embodiment of the present invention, the phrase "having risk (degree of risk) of developing" refers to a state in which onset of a disorder has not occurred, but in which onset is more likely to occur than in a healthy subject. "Having risk of developing a mood disorder" encompasses (i) a state in which an individual is at a stage prior to onset of a mood disorder and is highly likely to develop the mood disorder and (ii) a state in which an individual is in a depressive state that does not satisfy the diagnostic criteria for a mood disorder. The phrase "a depressive state that does not satisfy the diagnostic criteria for a mood disorder" can also be phrased as "a depressive state in which onset of a mood disorder has not occurred".

In an embodiment of the present invention, the phrase "evaluating/examining/diagnosing the risk (degree of risk) of developing a mood disorder" includes (i) evaluating/examining/diagnosing the presence or absence of risk (degree of risk) of developing a mood disorder, and/or the degree (high/low) of that risk and (ii) evaluating/examining/diagnosing the presence or absence of risk (degree of risk) of showing a depressive state, and/or the degree (high/low) of that risk. In other words, in a case where it has been determined through evaluation/examination/diagnosis that an individual has risk, the phrase "evaluating/examining/diagnosing the risk (degree of risk) of developing a mood disorder" further encompasses an aspect in which the degree of the risk is evaluated/examined/diagnosed.

In an embodiment of the present invention, the term "diagnose" refers to identifying a disorder or a condition of a disorder by assessing/evaluating: (i) whether or not a human subject has a target disorder; (ii) a degree of severity of a target disorder affecting a human subject, (iii) the risk (degree of risk) of developing a target disorder in a human subject, (iv) the presence or absence of a predisposing factor for a target disorder in a human subject, and/or (v) the curative effect of a treatment provided for a target disorder affecting a human subject. As used herein, the term "examination" refers to examination carried out for a human subject in which examination diagnosis or identification by a doctor is not essential, specifically examination with respect to: (i) whether or not the human subject has a target disorder; (ii) a degree of severity of a target disorder affecting the human subject, (iii) the risk of developing a target disorder in the human subject, (iv) the presence or absence of a predisposing factor for a target disorder in the human subject, and/or (v) the curative effect of a treatment provided for a target disorder affecting the human subject. Results obtained via the measurement method and examination of an embodiment of the present invention can be used as data for diagnosis.

In an embodiment of the present invention, the term "treatment" encompasses alleviating or completely curing symptoms of a target disorder, suppressing the worsening of symptoms of a target disorder, and suppressing or delaying the onset of a target disorder. In other words, the term "treatment" encompasses prevention in a case where onset of a target disorder has not occurred in a human subject.

In an embodiment of the present invention, the term "HHV-6" refers to human herpesvirus-6 (HHV: human herpesvirus) and "HHV-6" belongs to subfamily β-herpesvirus. While there exist two variants of HHV-6 (i.e. HHV-6 Variant A (HHV-6A) and HHV-6 Variant B (HHV-6B)), HHV-6 in an embodiment of the present invention is preferably HHV-6B.

In an embodiment of the present invention, the term "antibody" is intended to mean having a configuration that includes (a) an immunoglobulin (IgA, IgD, IgE, IgG, and IgM), and (b) a functional fragment of an antibody and a functional fragment of an antibody mutated within a range allowing the functional fragment to maintain reactivity. The term "functional fragment of the antibody" means a fragment including a partial region of any of the above-described antibodies and having an antigen binding capacity (synonymous with "antigen-binding fragment"). Concrete examples of the functional fragment of the antibody encompass an Fab fragment, an $F(ab')_2$ fragment, and an Fc fragment. In an embodiment of the present invention, examples of the antibody encompass a natural polyclonal antibody and a natural monoclonal antibody. Further, the examples of the antibody also encompass an antibody produced by a genetic recombinant technology and a functional fragment of such an antibody. The natural antibody is not limited to a particular one, and can be derived from any of species of living things such as cows, goats, guinea pigs, hamsters, horses, humans, mice, rabbits, rats, and sheep.

The antibody produced by the genetic recombinant technology is not particularly limited to any type, and can be, for example, (i) a chimeric antibody such as a humanized or primatized antibody obtained as a result of genetic modification of a natural antibody, (ii) a synthesized antibody, (iii) a recombinant antibody, (iv) a mutation-introduced antibody, or (v) a graft-binding antibody (e.g., an antibody to which another protein, a radioisotopic label, and/or the like is/are conjugated or fused). In addition, the antibody produced by the genetic modification technology can also be an antibody obtained as a result of introducing, into an antibody produced by the genetic recombinant technology, the same modification as that introduced into the natural antibody as described above.

Further, the antibody in accordance with an embodiment of the present invention can also be, but is not limited to, for example, a single-chain antibody or an anti-idiotype antibody.

The antibody recognizing the fusion protein in accordance with an embodiment of the present invention is called an "anti-fusion protein antibody". The phrase "antibody recognizing (the fusion protein)" means that the antibody specifically binds to (the fusion protein).

The term "in vivo" as used herein means an experimental system inside an individual organism whereas the term "in vitro" as used herein means a system that is not an experimental system inside an individual organism but a system which makes use of, for example, a cultured tissue, a cultured cell, or an isolated protein.

[1. Fusion Protein]

An embodiment of the present invention provides a fusion protein of a SITH-1 protein and a CAML protein (hereinafter, this fusion protein will be simply referred to as "fusion protein").

The inventors of the present invention found that when SITH-1 is expressed in a cell, SITH-1 binds to CAML present in the cell (Patent Literature 2). The inventors however could not isolate a conjugate of SITH-1 and CAML, since SITH-1 and CAML co-expressed in a cell were insoluble. The inventors of the present invention could successfully isolate a soluble conjugate of SITH-1 and CAML for the first time, by forming a fusion protein of SITH-1 and CAML.

Accordingly, in an aspect of the present invention, there is provided a method for obtaining a soluble conjugate of SITH-1 and CAML, by forming a fusion protein of SITH-1 and CAML by fusion of SITH-1 and CAML.

In an embodiment of the present invention, "SITH-1" is a protein which has an amino acid sequence shown in SEQ ID NO: 1 and which is isolated and identified as a protein that is specifically expressed during latent infection with human herpesvirus-6 (HHV-6). The term "SITH-1" is an abbreviation of a (Small protein encoded by the Intermediate stage Transcript of HHV-6)-1. SITH-1 is a protein consisting of 159 amino acids and having a molecular weight of approximately 17.5 kDa (GenBank under accession numbers HV763913.1 and HV763914.1). Note that the term "wild-type SITH-1" herein means a protein having an amino acid sequence shown in SEQ ID NO: 1. SITH-1 is encoded by a SITH-1 gene. cDNA of the SITH-1 gene has a size of 1795 base pairs (approximately 1.79 kbp) as shown in SEQ ID NO: 3. Further, the 954th to 956th nucleotide sequence represents a start codon (Kozak ATG) of the cDNA of the SITH-1 gene, whereas the 1431st to 1433rd nucleotide sequence represents a stop codon (TAA) of the cDNA of the SITH-1 gene. Therefore, the SITH-gene has, as an open reading frame (ORF) region, a sequence of 954th through 1430th nucleotides of the nucleotide sequence shown in SEQ ID NO: 3. The ORF has a size of 477 base pairs (approximately 0.48 kbp). Of the cDNA of the SITH-1, a nucleotide sequence representing the ORF region is shown in SEQ ID NO: 2. Note that the nucleotide sequence shown in SEQ ID NO: 2 includes the three nucleotides of the stop codon.

The fusion protein of a SITH-1 protein and a CAML protein in accordance with an embodiment of the present invention encompasses the following fusion proteins.

In an embodiment of the present invention, the "SITH-1 protein" is a protein binding to a wild-type CAML and thereby having activity of increasing an intracellular calcium concentration, which protein encompasses not only a wild-type SITH-1 but also all proteins included in the following proteins (1) to (4).

In an embodiment of the present invention, the SITH-1 protein can be, for example, any of the following proteins (1) to (4), which is a protein binding to a wild-type CAML and thereby having activity of increasing an intracellular calcium concentration.

(1) A protein binding to a wild-type CAML and thereby having activity of increasing an intracellular calcium concentration, which protein has an amino acid sequence shown in SEQ ID NO: 1.

(2) A protein binding to a wild-type CAML and thereby having activity of increasing an intracellular calcium concentration, which protein has an amino acid sequence in which 1 to 31 amino acids in the amino acid sequence shown in SEQ ID NO: 1 is/are substituted, deleted, inserted and/or added. Note that the number of amino acids having been substituted, deleted, inserted and/or added is preferably 1 to 23, more preferably 1 to 15, even more preferably 1 to 7, and particularly preferably 1 to 5 or 6. Hereinafter, substitution, deletion, insertion and/or addition of an amino acid(s) may be collectively referred to as amino acid mutation.

(3) A protein binding to a wild-type CAML and thereby having activity of increasing an intracellular calcium concentration, which protein has a sequence identity of 80% or higher with the amino acid sequence shown in SEQ ID NO: 1. Note that the sequence identity is preferably 85% or higher, more preferably 88% or higher, even more preferably 90% or higher, still more preferably 95% or higher, and particularly preferably 96% or higher, 97% or higher, 98% or higher, or 99% or higher.

(4) A protein binding to a wild-type CAML and thereby having activity of increasing an intracellular calcium concentration, which protein is encoded by a polynucleotide which hybridizes, under stringent conditions, with a polynucleotide having a sequence complementary to a polynucleotide that encodes the protein described above in (1) having activity of increasing an intracellular calcium concentration. Note that the stringent conditions will be described later in a section which discusses a polynucleotide in accordance with an embodiment of the present invention.

In an embodiment of the present invention, "CAML" is a calcium-signal modulating cyclophilin ligand having an amino acid sequence shown in SEQ ID NO: 4. The "CAML" is also a protein consisting of 296 amino acids and having a molecular weight of approximately 38 kDa. Note that in an embodiment of the present invention, the term "wild-type CAML" means a protein having an amino acid sequence shown in SEQ ID NO: 4. cDNA of the CAML gene has a size of 1350 base pairs (approximately 1.35 kbp) as shown in SEQ ID NO: 5. The nucleotide sequence that represents an ORF of that CAML gene is shown in SEQ ID NO: 22.

The CAML is originally isolated as an endoplasmic reticulum membrane protein that regulates T cell receptor signaling. The CAML is subsequently found to function as a TRC40 receptor in an endoplasmic reticulum membrane (Non-Patent Literature 4). Further, the CAML is known to be strongly expressed in lymphocytes and in a brain, and has a function to increase an intracellular calcium concentration when strongly bound to SITH-1 in a cell (Patent Literature 2).

In an embodiment of the present invention, the "CAML protein" is a protein binding to a wild-type SITH-1 and thereby having activity of increasing an intracellular calcium concentration, which protein encompasses not only a wild-type CAML but also all proteins included in the following proteins (5) to (8).

The "CAML protein" in accordance with an embodiment of the present invention can be any of the following proteins (5) to (8), which is a protein binding to a wild-type SITH-1 and thereby having activity of increasing an intracellular calcium concentration.

(5) A protein binding to a wild-type SITH-1 and thereby having activity of increasing an intracellular calcium concentration, which protein has an amino acid sequence shown in SEQ ID NO: 4.

(6) A protein binding to a wild-type SITH-1 and thereby having activity of increasing an intracellular calcium concentration, which protein has an amino acid sequence in which 1 to 59 amino acids in the amino acid sequence shown in SEQ ID NO: 4 is/are substituted, deleted, inserted and/or added. Note that the number of amino acids having been substituted, deleted, inserted and/or added is preferably 1 to 44, more preferably 1 to 29, even more preferably 1 to 23, still more preferably 1 to 14, and particularly preferably 1 to 5 or 6.

(7) A protein binding to a wild-type SITH-1 and thereby having activity of increasing an intracellular calcium concentration, which protein has a sequence identity of 80% or higher with the amino acid sequence shown in SEQ ID NO: 4. Note that the sequence identity is preferably 85% or higher, more preferably 88% or higher, even more preferably 90% or higher, still more preferably 95% or higher, and particularly preferably 96% or higher, 97% or higher, 98% or higher, or 99% or higher.

(8) A protein binding to a SITH-1 and thereby having activity of increasing an intracellular calcium concentration, which protein is encoded by a polynucleotide which hybridizes, under stringent conditions, with a polynucleotide having a sequence complementary to a polynucleotide that encodes a protein, described above in (1), which binds to a wild-type SITH-1 and thereby has activity of increasing an intracellular calcium concentration. Note that the stringent conditions will be described later in a section which discusses a polynucleotide in accordance with an embodiment of the present invention.

How the SITH-1 protein and the CAML protein are derived is not limited. For example, the SITH-1 protein and the CAML protein may be synthesized chemically or produced by a gene recombination technique. More specifically, the SITH-1 protein and the CAML protein can encompass in its scope an isolated and purified polypeptide, a chemically synthesized polypeptide, and a polypeptide produced from a host cell via a gene recombination technique. The host cell will be described in detail later in a section which discusses "transformed cell".

One example of the SITH-1 protein is a wild-type SITH-1 protein represented by an amino acid sequence shown in SEQ ID NO: 1. One example of the CAML protein is a wild-type CAML protein represented by an amino acid sequence shown in SEQ ID NO: 4.

The proteins described in the above (2) to (4) can be each taken as a mutant based on a protein described in the above (1). Meanwhile, the proteins described in the above (6) to (8) can be each taken as a mutant based on a protein described in the above (5). The proteins described in the above (2) to (4) can be each obtained, for example, by expressing a mutant in which a mutation is artificially introduced, by site-directed mutagenesis, in a polynucleotide encoding the protein described in the above (1). The proteins described in the above (6) to (8) can be each obtained, for example, by expressing a polynucleotide in which a mutation is artificially introduced, by site-directed mutagenesis, in a polynucleotide encoding the protein described in the above (5).

In the fusion protein of an embodiment of the present invention, the SITH-1 protein and the CAML protein may be bound in any order. The fusion protein of the SITH-1 protein and the CAML protein of an embodiment of the present invention is preferably a fusion protein in which an N-terminal side of the CAML protein is bound to a C-terminal side of the SITH-1 protein (hereinafter, referred to as "S-C protein") or a fusion protein in which a C-terminal side of the CAML protein is bound to an N-terminal side of the SITH-1 protein (hereinafter, referred to as "C-S protein").

Further, the fusion protein may have a structure containing at least either (i) two or more SITH-1 proteins described above or (ii) two or more CAML proteins described above. The S-C protein preferably has activity of increasing an intracellular calcium concentration.

A method for preparing the fusion protein is not limited to a particular one. The fusion protein may be expressed by using, for example, a conventionally-known genetic engineering procedure. For example, the fusion protein can be obtained by expressing a gene encoding the fusion protein, with use of an expression system such as *Escherichia coli*.

In the fusion protein, the SITH-1 protein and the CAML protein may be directly bound to each other or alternatively may be bound to each other via a linker (spacer).

The linker can be a linker made of a polypeptide including a plurality of amino acids. The length of the above polypeptide linker is not limited, and may be 300 or less amino acids. The length is preferably 200 or less amino acids, 170 or less amino acids, 150 or less amino acids, 140 or less amino acids, 130 or less amino acids, 120 or less amino acids, 110 or less amino acids, 100 or less amino acids, 90 or less amino acids, 80 or less amino acids, 70 or less amino acids, 60 or less amino acids, or 50 or less amino acids, or more preferably 40 or less amino acids. Further, the length of the above polypeptide linker may be 5 or more amino acids and is preferably 10 or more amino acids. The linker can be, for example, a linker having an amino acid sequence shown in SEQ ID NO: 6, but the linker is not limited to such a linker.

Further, an embodiment of the present invention encompasses in its scope a fusion protein in which another polypeptide is bound in addition to the above. For example, to the C-terminus of the fusion protein, a tag for subsequent purification and/or detection may be added. Examples of such a tag encompass, but are not limited to, a c-myc epitope tag (Munro and Pelham (1986) Cell 46: 291-300), a histidine tag (Hochuli et al (1988) BiosurasshuTechnol 6: 1321-1325, Smith et al. (1988) J Biol Chem 263: 7211-7215), and the like.

Note that the fusion protein may be expressed in another conventionally-known expression system such as an insect cell expression system, a plant cell expression system, a mammal cell expression system, a yeast cell expression system, or a cell-free expression system. For example, cells and expression methods described below in the section entitled [4. Transformed cell] are suitably used.

Examples of the fusion protein in accordance with an embodiment of the present invention encompass an S-C protein having an amino acid sequence shown in, for example, SEQ ID NO: 17 and a C-S protein having an amino acid sequence shown in, for example, SEQ ID NO: 18.

In addition, an antibody recognizing the fusion protein in accordance with an embodiment of the present invention is also an aspect of the present invention.

[2. Polynucleotide Encoding Fusion Protein According to Embodiment of Present Invention]

The polynucleotide in accordance with an embodiment of the present invention encodes any of fusion proteins described in the above [1. Fusion protein]. Concretely, such a polynucleotide can be, for example, any of polynucleotides described in the following (1) to (4).

(1) A polynucleotide encoding a polypeptide having an amino acid sequence shown in SEQ ID NO: 17 or 18.

(2) A polynucleotide encoding a protein having an amino acid sequence in which 1 to 96 amino acids are substituted, deleted, inserted and/or added in the amino acid sequence shown in SEQ ID NO: 17 or 18. Note that the number of amino acids having been substituted, deleted, inserted and/or added is preferably 1 to 72, more preferably 1 to 48, more preferably 1 to 24, more preferably 1 to 19, more preferably 1 to 14, even more preferably 1 to 9, and particularly preferably 1 to 4, 5 or 6.

(3) A polynucleotide encoding a protein having an amino acid sequence whose sequence identity is 80% or higher with respect to the amino acid sequence shown in SEQ ID NO: 17 or 18. Note that the sequence identity of the amino acid sequence is preferably 90% or higher, more preferably 95% or higher, and particularly preferably 96% or higher, 97% or higher, 98% or higher, or 99% or higher.

(4) A polynucleotide encoding any of the above proteins described in (1) to (3) above, which polynucleotide hybridizes, under stringent conditions, with a polynucleotide having a sequence complementary to the polynucleotide described in the above (1). Note that the "stringent conditions" can be for example, conditions described in the reference document [Molecular cloning—a Laboratory manual 2nd edition (Sambrook et al., 1989)]. Examples of the "stringent conditions" encompass conditions where polynucleotides are incubated in a hybridization solution (containing 50% formamide, 5×SSC (150 mM NaCl, 15 mM trisodium citrate), 50 mM sodium phosphate (pH 7.6), 5× Denhart's solution, 10% dextran sulfate, and 20 µg/ml of sheared denatured salmon sperm DNA) overnight at 42° C., and then a filter is washed with 0.1×SSC at approximately 65° C. Further, the above hybridization can be performed by a conventionally-known method and is not limited to a particular one. Typically, a higher temperature and/or a lower salt concentration, increases stringency (hybridization becomes more difficult).

The polynucleotide in accordance with an embodiment of the present invention may be present in the form of RNA (e.g., mRNA) or in the form of DNA (e.g., cDNA). The DNA may be double-stranded DNA or single-stranded DNA. The polynucleotide in accordance with an embodiment of the present invention may include an additional sequence such as a sequence of an untranslated region (UTR).

A method for obtaining (isolating) the polynucleotide in accordance with an embodiment of the present invention is not limited to a particular one. The polynucleotide in accordance with an embodiment of the present invention may be synthesized by a nucleic acid synthesis method such as a phosphoramidite method.

Further, the method for obtaining the polynucleotide in accordance with an embodiment of the present invention can be a method using an amplification means such as PCR. For example, primers are prepared respectively based on sequences at the 5' end and the 3' end (or their complementary sequences) of cDNA of the polynucleotide. Then, PCR or the like is performed with use of the primers and a genomic DNA (or cDNA) or the like as a template, so as to amplify a DNA region between the primers. This makes it possible to obtain a great amount of DNA fragments containing the polynucleotide in accordance with an embodiment of the present invention.

Examples of the polynucleotide in accordance with an embodiment of the present invention can encompass polynucleotides represented by nucleotide sequences shown in SEQ ID NOs: 19 and 20, respectively, and the like.

Further, the polynucleotide in accordance with an embodiment of the present invention may be a polynucleotide in which a polynucleotide encoding the linker is inserted between a polynucleotide encoding the SITH-1 protein and a polynucleotide encoding the CAML protein.

[3. Support to which Fusion Protein is Immobilized]

An embodiment of the present invention provides a support to which the fusion protein in accordance with an embodiment of the present invention is immobilized. Such a support is not limited to a particular one, provided that the support is made of a solid material or an insoluble material (e.g. material which can be separated from a reaction mixture by filtering, precipitation, magnetic separation, or the like). The solid support is not particularly limited in shape and can have a plate shape (i.e., a substrate form or a sheet form), a spherical shape, or the like. Concrete examples of the shape of the solid support encompass, but are not limited to, shapes of beads, magnetic beads, thin films, fine tubes, filters, plates, microplates, carbon nanotubes, and sensor chips. In a case where the solid support is a flat support such as a thin film or a plate, the solid support can be provided with a pit, a groove, a filter bottom, or the like as known in the technical field to which the present invention pertains. A person skilled in the art can use as appropriate a conventionally-known method, as a method for immobilizing the fusion protein to the support, in accordance with a property of the support and/or in accordance with a purpose.

Further, in regard to a method for providing and immobilizing the polypeptide in accordance with an embodiment of the present invention onto a base substrate, the method should be appropriately selected depending on a material of the base substrate. Concrete examples of the method encompass, but are not limited to, a biotin-avidin method, an antigen-antibody method, and an affinity tag method using a His-tag or the like.

Further, the support in accordance with an embodiment of the present invention further encompass a cell (host cell) into which a gene encoding the fusion protein is introduced so that the fusion protein will be expressed. This aspect is preferred particularly in a case where measurement is carried out by an (indirect) fluorescent antibody method. Note that a person skilled in the art can appropriately select the cell according to a conventionally-known technique. Preferable examples of the cell encompass a human-derived cell, a monkey-derived cell, and an insect cell. A human-derived cell is most preferable. Note that the details of the host cell will be discussed in the section entitled [9. Recombinant expression vector].

[4. Antibody Detection Instrument]

An "antibody detection instrument" in an embodiment of the present invention is an instrument which uses, as a probe, the fusion protein of an embodiment of the present invention. That is, the "antibody detection instrument" can be, for example, an instrument obtained by immobilizing, onto a support, the probe that specifically binds to an anti-fusion protein antibody. The support encompasses those described above in the section entitled [3. Support to which fusion protein is immobilized].

[5. Method for Measuring Level of Anti-Fusion Protein Antibody]

The inventors of the present invention have found that (a) it is possible to diagnose whether or not a human subject has a mood disorder by measurement of an antibody recognizing SITH-1 in a biological sample obtained from the human subject and (b) SITH-1 strongly binds to CAML in an astrocyte and thereby increases an intracellular calcium concentration (Patent Literature 2).

Subsequently, the inventors of the present invention have found a mechanism of pathogenesis of a mood disorder as below (Patent Literature 3). That is, when SITH-1 is expressed due to infection of olfactory epithelium with HHV-6, an olfactory system is impaired. This causes apoptosis of olfactory bulb cells. Such dysfunction of the olfactory system causes a strong false signal to be transmitted to the hypothalamus, and consequently causes "stress vulnerability" which is a state in which an improper stress response can easily occur. Then, in a case where the "stress vulnerability" occurs, a hypersensitive response is made to even a mild stress in an environment. This results in development of a mood disorder. In a case where olfactory epithelium cells are frequently infected with HHV-6, symptoms of the mood disorder become severer. Note that the olfactory epithelium cells herein refer to cells of olfactory epithelium, which cells encompass olfactory ensheathing cells. The olfactory epithelium cells are preferably glial cells of olfactory epithelium.

The inventors of the present invention further advanced their diligent studies. As a result, the inventors have found that measurement of a level of an antibody recognizing a fusion protein of SITH-1 and CAML makes it possible not only to determine whether or not a human subject has a mood disorder but also to assess/evaluate the following (i) to (vi): (i) whether or not a human subject is in a depressive state in which onset of a mood disorder has not occurred; (ii) the risk (degree of risk) of developing a mood disorder in a human subject; (iii) the risk (degree of risk) that a human subject may show a depressive state; (iv) whether or not a human subject has a predisposing factor for a mood disorder; (v) a degree of severity of a mood disorder; and/or (vi) an effect of treatment of a mood disorder on a human subject suffering a mood disorder. Further, it has become clear that the above measurement method of an embodiment of the present invention can have a significantly improved detection sensitivity as compared to a conventional method, and also that it is possible to identify a cause of a mood disorder. The following will discuss the details of the measurement method.

An embodiment of the present invention provides a method of measuring, by using a fusion protein in accordance with an embodiment of the present invention, a level of an antibody recognizing the fusion protein in a target for measurement of a level of an anti-fusion protein antibody.

In one embodiment, the method of measuring an antibody level in accordance with an embodiment of the present invention includes: 1) a contact step in which the fusion protein in accordance with an embodiment of the present invention is put in contact with a target for measurement of a level of an anti-fusion protein antibody; and 2) a measurement step in which the level of the anti-fusion protein antibody is measured by detection of the anti-fusion protein antibody after the contact step.

In an aspect of the present invention, there is provided a method of measuring, by using the fusion protein in accordance with an embodiment of the present invention, a level of an antibody recognizing the fusion protein in a biological sample isolated from a subject.

The term "subject" herein means humans and non-human mammals, but preferably the "subject" is a human.

In one embodiment, the method of measuring an antibody level in accordance with an embodiment of the present invention includes: 1) a contact step in which the fusion protein in accordance with an embodiment of the present invention is put in contact with a biological sample isolated from a subject; and 2) a measurement step in which the antibody level is measured by detection of the anti-fusion protein antibody after the contact step.

(Contact Step)

The target for detection of the antibody level is not particularly limited in type, provided that the target is an object of interest with regard to whether or not the object contains an antibody and an amount of the antibody contained in the object. Examples of the target encompass a biological sample and a non-biological sample. The target is preferably a biological sample isolated from a subject.

The "biological sample" in an embodiment of the present invention is not limited to a particular one, provided that the biological sample is a sample which is derived from a living organism and which allows for measurement of amount of antibody and antibody titer. The biological sample is preferably one or more selected from the group consisting of blood, serum, plasma, cerebrospinal fluid, saliva, nasal discharge, sweat, lymph, and breast milk, and more preferably blood, serum, plasma or cerebrospinal fluid. In view of a low degree of invasion of a subject, peripheral blood is preferable among types of blood samples. Meanwhile, in a case where an IgA antibody level is to be detected, saliva or nasal discharge is preferable.

Note that an example of the non-biological sample encompasses an anti-fusion protein antibody standard sample containing an anti-fusion protein antibody at a predetermined concentration.

(Measurement Step)

The measurement step is performed after the contact step. In the measurement step, the anti-fusion protein antibody is detected, so that a level of this anti-fusion protein antibody is measured.

According to an embodiment of the present invention, the term "antibody level (level of antibody)" means an amount or titer of the anti-fusion protein antibody contained in a biological sample. The amount or titer of the antibody can each be measured by use of a conventionally-known method. Examples of the conventionally-known method for measurement of such an antibody level encompass, but are not limited to, assays which use in vitro immunohistological methods such as a (indirect) fluorescent antibody method (herein, the indirect fluorescent antibody method may also be referred to as "IFA"), dot blot assay, Western blotting, enzyme-linked immunosorbent assay (ELISA (including sandwich ELISA, direct ELISA, and competitive ELISA)), radioimmunoassay (RIA), and immunodiffusion assay. Alternatively, the antibody can be measured by in vivo image analysis or the like.

The amount of an antibody present in a biological sample may be easily calculated, for example, by comparison with an amount of the antibody present in a standard preparation (e.g., a standard sample from a healthy subject or a standard sample from a typical patient of a mood disorder), with use of a linear regression computer algorithm. Such an assay for detection of an antibody is disclosed in, for example, Iacobellira, Breast Cancer Research and Treatment 11: 19-30 (1988) in regard to ELISA.

Suitable enzyme labels may be exemplified by those derived from a class of oxidases which catalyze the generation of hydrogen peroxide through reaction with the substrate. Glucose oxidase is particularly preferable, since it has satisfactory stability and its substrate (glucose) can be easily obtained. Activity of the oxidase label can be assayed by measuring a concentration of hydrogen peroxide formed by an enzyme-labeled antibody/substrate reaction. In addition to enzymes, other suitable labels include radioisotopes (e.g., iodine ($^{125}$I and $^{121}$I), carbon ($^{14}$C), sulfur ($^{35}$S), tritium ($^{3}$H), indium ($^{112}$In), and technetium ($^{99m}$Tc)), as well as fluorescent labels (e.g., fluorescein and rhodamin) and biotin.

The following lists concrete examples of a label available for an embodiment of the present invention. Examples of suitable enzyme labels include malate dehydrogenase, staphylococcus nuclease, yeast alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotope labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd. Indium 111 ($^{111}$In) is a preferred isotope in the case where in vivo imaging is employed, since this avoids a problem of dehalogenation of a monoclonal antibody labeled with $^{125}$I or $^{131}$I, which dehalogenation is caused by a liver. Further, this radionuclide has a favorable gamma release energy for imaging (Perkins et al., Eur. J. Nucl. Med. 10: 296-301 (1985); Carasquillo et al., J. Nucl. Med. 28: 281-287 (1987)). For example, indium 111 ($^{111}$In) coupled to a monoclonal antibody with use of 1-(P-benzyl isothiocyanate)-DPTA has shown little uptake in non-tumorous tissues, particularly a liver, and therefore enhances specificity of tumor localization (Esteban et al., J. Nucl. Med. 28: 861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include $^{152}$Eu label, fluorescein label, isothiocyanate label, rhodamin label, phycoerythrin label, phycocyanin label, allophycocyanin label, o-phthalaldehyde label, and fluorescamine label.

Examples of suitable marker toxins include diphtheria toxin, ricin, and cholera toxin.

Examples of chemiluminescent labels include luminal label, isoluminal label, aromatic acridinium ester label, imidazole label, acridinium salt label, oxalate ester label, luciferin label, luciferase label, and aequorin label.

Examples of contrast agents for nuclear magnetic resonance include heavy metal atomic nuclei such as Gd, Mn, and Fe.

Representative techniques for binding the above-mentioned labels to antibodies are provided by Kennedy et al. (Clin. Chim. Acta 70: 1-31 (1976)) and Schurs et al. (Clin. Chim. Acta 81: 1-40 (1977)). Coupling techniques described in the latter include a glutaraldehyde method, a periodate method, a dimaleimide method, and a m-maleimidebenzyl-N-hydroxy-succinimide ester method. All of these methods are incorporated herein by reference.

In the above measurement step, for measurement of an antibody which recognizes and binds to an S-C protein (hereinafter, referred to as "anti-S-C antibody"), the S-C protein can be favorably used. Meanwhile, for measurement of an antibody which recognizes and binds to a C-S protein (hereinafter, referred to as "anti-C-S antibody"), the C-S protein can be favorably used.

Respective levels of the anti-S-C antibody and the anti-C-S antibody may be measured either simultaneously or in turn.

In the method of measuring an antibody in accordance with an embodiment of the present invention, in a case where measurement is performed by an immunohistological method and preferably by the IFA, both a biological sample and a labeled anti-CAML antibody are reacted with fusion protein expressing cells. This makes it possible to, for example, confirm (i) transfection efficiency, (ii) a protein expression level, and/or (iii) a measurement site at the time when a fluorescent intensity is to be measured. The anti-CAML antibody is not limited to any type, and it is possible to suitably use a monoclonal antibody derived from a cow, a goat, a guinea pig, a hamster, a horse, a human, a mouse, a rabbit, a rat, or sheep, which monoclonal antibody is prepared by a conventionally-known method. Such double staining makes it possible to easily perform automatic measurement by use of an image analyzer or the like. For example, in the case of double staining shown in FIG. 13 of Examples which will be discussed later, in IFA fluorescent intensity measurement of serum of a patient having a mood disorder, automatic measurement by use of an image analyzer is easily performed by measurement of a green light emission intensity at a portion stained red with a mouse anti-CAML antibody. Further, measurement of a red light emission intensity of the mouse anti-CAML antibody allows for correction of a protein expression level in each measurement.

Further, the method of measuring an antibody level may further include, in the measurement step, measuring a level of the anti-CAML antibody in a target of detection of the antibody level, for example, in a biological sample isolated from a subject. Such measurement of the level of the anti-CAML antibody may be performed simultaneously with measurement of the level of the anti-fusion protein antibody in the measurement step. Alternatively, the level of the anti-CAML antibody and the level of the anti-fusion protein antibody may be sequentially measured in the measurement step. In this case, the anti-CAML antibody and the anti-fusion protein antibody can be measured in any order. Examples of a protein for use in the measurement of the level of the anti-CAML antibody encompass CAML proteins having amino acid sequences shown in SEQ ID NOs: 4 and 21, respectively.

A concrete example of the measurement method including measuring the level of the anti-CAML antibody encompasses a method in which the level of the anti-CAML antibody is measured by reacting, with cells in which a CAML protein is expressed, serum identical to serum for use in the measurement of the anti-fusion protein antibody. It has become clear that in a case where the IFA fluorescent intensity of a serum antibody against the fusion protein is corrected by the IFA fluorescent intensity of a serum antibody against CAML, performance of diagnosis of depression or performance of diagnosis of a depressive state is improved (see Example 3).

(Examination Step)

The method of measuring an antibody level in accordance with an embodiment of the present invention may further include, as necessary, an examination step in which any of the following (i) to (viii) is examined on the basis of a result of measurement in the above measurement step: (i) whether or not a subject has a mood disorder; (ii) the risk of developing a mood disorder; (iii) a risk that a human subject (e.g., healthy subject) may show a depressive state; (iv) whether or not a human subject is in a depressive state that does not satisfy the diagnostic criteria for a mood disorder; (v) the presence or absence of a predisposing factor for developing a mood disorder; (vi) a cause of a depressive state; (vii) a degree of severity of a mood disorder; and (viii) an effect of treatment of a mood disorder on a human subject suffering a mood disorder.

Such an examination is intended to be performed by any examiner, and does not include diagnosis by a doctor or the like. The examination step is similar to a diagnosis step according to the following diagnosis method. Details of the examination step will be discussed in the following [6. Diagnosis method for mood disorder].

[6. Diagnosis Method for Mood Disorder]

An embodiment of the present invention provides a diagnosis method for a mood disorder in a human subject, which diagnosis method includes the step of measuring a level of an anti-fusion protein antibody in accordance with an embodiment of the present invention in a biological sample isolated from a human subject.

The term "human subject" herein means a target human. There is no particular limitation in age, sex, etc. to the human subject.

In one example, the anti-fusion protein antibody may be an anti-S-C antibody or an anti-C-S antibody.

For example, the diagnosis method for a mood disorder in a human subject in accordance with an embodiment of the present invention includes: a measurement step in which a level of the anti-fusion protein antibody in accordance with an embodiment of the present invention is measured in a biological sample isolated from a human subject; and a diagnosis step in which one or more of the following (i) to (viii) is/are diagnosed on the basis of a result of measurement in the measurement step: (i) whether or not the human subject has a mood disorder; (ii) whether or not the human subject is in a depressive state that does not satisfy the diagnostic criteria for a mood disorder; (iii) the risk of developing a mood disorder; (iv) the risk that the human subject (e.g., healthy subject) may show a depressive state; (v) the presence or absence of a predisposing factor for developing a mood disorder; (vi) a cause of a depressive state; (vii) a degree of severity of a mood disorder; and (viii) an effect of treatment of a mood disorder on the human subject suffering a mood disorder. The measurement step in the diagnosis method in accordance with an embodiment of the present invention is the same as that discussed above in the (Measurement step) of [5. Method for measuring level of anti-fusion protein antibody].

(Diagnosis Step)

The diagnosis step includes assessment/evaluation of one or more of the following (i) to (vii): (i) whether or not a human subject has a mood disorder; (ii) whether or not a human subject is in a depressive state in which onset of a mood disorder has not occurred; (iii) the risk (degree of risk) of developing a mood disorder in a human subject; (iv) the risk (degree of risk) that a human subject (e.g., healthy subject) may show a depressive state; (v) whether or not a human subject has a predisposing factor for developing a mood disorder; (vi) a degree of severity of a mood disorder; and (vii) an effect of treatment of a mood disorder on a human subject suffering a mood disorder. The term "mood disorder and the phrase depressive state that does not satisfy the diagnostic criteria for a mood disorder" preferably does not include a temporary depressive state caused by a stressor.

In another embodiment of the present invention, in a case where a human subject shows a depressive state, the diagnosis method may include the step of determining whether or not the depressive state is a temporary depressive state caused by a stressor. If the result of diagnosis by this method is positive, it is determined that a depressive state occurs by the above-described mechanism of pathogenesis, which mechanism has been found by the inventors of the present invention. Note that the diagnosis method in accordance with an embodiment of the present invention can be understood to assess/evaluate a predisposing factor related to a mood disorder in a human subject.

In the diagnosis step, it is possible to diagnose not only whether or not a human subject has a mood disorder but also the human subject is in a depressive state that does not satisfy the diagnostic criteria for a mood disorder, by measuring a level of the anti-S-C antibody in a biological sample isolated from the human subject. In other words, the diagnosis step allows for nothing less than assessment of the risk of developing a mood disorder in the human subject. Further, in a case where the human subject shows a depressive state, it is possible to determine whether or not the depressive state is a temporary depressive state caused by a stressor, that is, it is possible to determine a cause of the depressive state. Further, it is possible to assess the risk that the human subject may be in a depressive state in the future even in a case where the human subject is currently a healthy subject who does not show any depressive state.

Further, it is possible to distinguish, between (i) a healthy state and (ii) a mood disorder which has been developed or a depressive state that does not satisfy the diagnostic criteria for a mood disorder, by measuring a level of the anti-C-S antibody in a biological sample isolated from a human subject. This makes it possible to assess the risk of developing a mood disorder in the human subject. Further, in a case where the human subject shows a depressive state, it is possible to determine whether or not the depressive state is a temporary depressive state caused by a stressor, that is, it is possible to determine a cause of the depressive state.

On the basis of (i) a result of measurement of the above antibody level, the presence or absence of a symptom of a mood disorder in each human subject group, and a degree of severity of the mood disorder (see Examples 2 and 3), (ii) a fact that SITH-1 binds to CAML and thereby increases an intracellular calcium concentration, and (iii) the mechanism of pathogenesis of a mood disorder (the mechanism will be discussed later), the inventors of the present invention have found that: a larger number of times of SITH-1 expression in olfactory epithelium cells results in (a) an increased risk of developing a mood disorder, (b) an increased predisposing factor for a mood disorder, and (c) an increased degree of severity of a mood disorder and (d) accordingly an increased level of the anti-fusion protein antibody.

The mechanism has been clarified as below from the result of the above studies, but the mechanism is not limited to the following. That is, the following is considered to be the mechanism. Originally, an autoimmune reaction to CAML occurs in humans. When infection of olfactory epithelium with HHV-6 causes expression of SITH-1 and then CAML binds to this SITH-1, immunity to CAML shifts to immunity to a conjugate of CAML and SITH-1. Subsequently, as a result of frequent infection with HHV-6, a major epitope transfers from an anti-C-S antibody recognition site to an anti-S-C antibody recognition site, and further to an anti-SITH-1 antibody recognition site. This mechanism is also supported by the fact that a level of an anti-CAML antibody in an anti-SITH-1 antibody-positive patient suffering from depression is significantly lower than that of a healthy subject (see FIG. 9). Further, enhancement of an immune reaction by autoimmunity to CAML can provide an explanation about a reason why SITH-1 is detected as a serum antibody with a high sensitivity though SITH-1 is produced only a little in an astrocyte present in a brain, olfactory epithelium, and the like.

Further, in view of the above mechanism, it is clear that by measurement of the level of the anti-S-C antibody, the level of the anti-C-S antibody, and/or a level of the anti-SITH-1 antibody in a biological sample isolated from a human subject, it is possible to (i) assess a degree of progression of a mood disorder and/or a depressive state that does not satisfy the diagnostic criteria for a mood disorder and/or (ii) estimate prognosis of the mood disorder and/or the depressed state.

The following will discuss in more detail the diagnosis step.

A person skilled in the art can properly set a threshold of the "antibody level", in view of (i) a quantitative value (normal value) of a healthy subject, (ii) a quantitative value (disease value) of a typical mood disorder patient, or (iii) a quantitative value (disease value) of a mild mood disorder patient, a moderate mood disorder patient, or a severe mood disorder patient. That is, in general, a threshold (i.e. cutoff value) for a diagnostic drug is properly set according to a purpose of the diagnostic drug by a person skilled in the art on the basis of many measured values obtained from healthy subjects and patients in clinical tests. (For example, in a case where, as with a screening examination, a definite diagnosis is to be made in a secondary examination or subsequent examinations and the highest priority is put on prevention of overlooking a disease group, sensitivity is prioritized over specificity, so that the cutoff value is set low. In contrast, in a case where a degree of a symptom of a mood disorder is to be determined, the threshold is set high in view of respective quantitative values of mild mood disorder patients, moderate mood disorder patient, and severe mood disorder patient.) Based on the disclosure herein, a person skilled in the art can easily decide a threshold for diagnosis. It is possible to directly use a numeric value of a sample from a healthy subject or an individual mood disorder patient, as a numeric value of a control for use in diagnosis, or alternatively to use an average value obtained from numeric values of samples of a certain number of healthy subjects or mood disorder patients as a population.

That is, for example, it can be determined that "the antibody level is high", depending on whether a measured antibody level is above the threshold (e.g., an antibody level of a healthy subject). In contrast, it can be determined that "the antibody level is low", depending on whether a measured antibody level is below the threshold.

In other words, for example, one or more of the following (i) to (viii) can be diagnosed (assessed/evaluated) by, for example, a comparison, with regard to the antibody level obtained in the above-described measurement step, between (a) a numeric value of a sample isolated from a human subject and (b) the normal value serving as the above-described control and/or the patient's value or the threshold (cutoff value): (i) whether or not a mood disorder has been developed; (ii) the risk of developing a mood disorder; (iii) the risk that a human subject (e.g., healthy subject) may show a depressive state; (iv) whether or not a human subject is in a depressive state that does not satisfy the diagnostic criteria for a mood disorder; (v) a cause of a depressive state; (vi) the presence or absence of a predisposing factor for developing a mood disorder; (vii) a degree of severity of a mood disorder; and (viii) an effect of treatment of a mood disorder on a human subject suffering a mood disorder. In one diagnosis example, if an antibody level in a biological sample isolated from a human subject is significantly higher than that of a control, the human subject is determined as follows: (i) a mood disorder is developed in the human subject; (ii) the human subject has the risk of developing a mood disorder; (iii) the depressive state of the human subject is not a temporary depressive state caused by a stressor; (iv) the human subject has a predisposing factor for developing a mood disorder; and/or (v) an effect of treatment of the mood disorder on the human subject suffering the mood disorder is not sufficient. Note that the antibody level may be determined to be significantly high as a result of quantitative measurement or as a result of qualitative measurement. In other words, the diagnosis method may include not only comparison of concrete numeric values but also relative comparison of amounts (actual calculation of an amount is not necessary, and whether an amount is higher or lower than a certain reference is determined). A control sample can be measured as above simultaneously with or separately from the sample of the human subject. In other words, a numeric value of a control sample for comparison with a numeric value of the human subject may be obtained in measurement that is performed at a different time from measurement of the numeric value of the human subject. Further, a person who measures the human subject does not need to measure the control sample. For example, the above threshold can be, for example, a measured value of the control sample which measured value has been obtained in advance and accumulated in a database or the like.

The above-described diagnosis methods each may further include the step of measuring a level of the anti-CAML antibody. The inventors of the present invention have found that the anti-CAML antibody is present in human serum (see Example 2). Note that since CAML is a human protein, the anti-CAML antibody is considered to be an autoantibody resulting from an autoimmune reaction. It is possible to further improve accuracy of diagnosis by correcting, by the level of the anti-CAML antibody of each specimen, the antibody level of each specimen obtained by the diagnosis method for a mood disorder with use of the above fusion protein (see Example 3). Such a correction can be preferably, but is not limited to, a correction performed by dividing, by the level of the anti-CAML antibody of each specimen, the level of each specimen obtained by the diagnosis method for a mood disorder with use of the above fusion protein.

Further, this diagnosis accuracy-improving effect can be also applied to a "method for diagnosing whether or not a human subject has a mood disorder, by measuring an anti-SITH-1 antibody in a biological sample isolated from the human subject" (Patent Literature 2, hereinafter, referred to as "conventional method"), which method has been developed by the inventors of the present invention (see FIGS. 6 and 10).

Therefore, in an aspect of the present invention, there is provided a diagnosis method for a mood disorder which diagnosis method includes measuring a level of an anti-SITH-1 antibody in a biological sample isolated from a human subject, the diagnosis method including the step of measuring a level of an anti-CAML antibody in the biological sample isolated from the human subject.

Note that an aspect of the present invention also encompasses a measurement method including the steps of: 1)

measuring a level of an anti-SITH-1 antibody in a biological sample isolated from a subject; and 2) measuring a level of an anti-CAML antibody in the biological sample isolated from the subject. Such measurement of the level of the anti-CAML antibody may be performed simultaneously with measurement of the level of the anti-SITH-1 antibody. Alternatively, the level of the anti-CAML antibody and the level of the anti-SITH-1 antibody may be sequentially measured. In this case, the anti-CAML antibody and the anti-fusion protein antibody can be measured in any order.

(Other Steps)

The diagnosis method in accordance with an embodiment of the present invention can be combined as appropriate with at least one of conventional diagnosis methods such as a method employing a medical interview and a method employing a questionnaire such as the Beck Depression Inventory.

Note that a method of obtaining data for making a diagnosis in accordance with an embodiment of the present invention is also an aspect of the present invention. That is, an embodiment of the present invention encompasses a method of obtaining data for making a diagnosis, which method includes each step of the above-mentioned diagnosis method. For example, an embodiment of the present invention encompasses a method of obtaining data for making a diagnosis of a mood disorder, which method includes the step of obtaining data of the level of the anti-fusion protein antibody in a biological sample isolated from a human subject, for the purpose of using the data for the diagnosis method including each step described above. The method of obtaining data in accordance with an embodiment of the present invention more preferably includes the step of obtaining data of the level of the anti-CAML antibody.

As described in Examples, it has become clear that as compared to conventional methods, the diagnosis method of an embodiment of the present invention has an improved detection sensitivity. The diagnosis method in accordance with an embodiment of the present invention is preferably a diagnosis method of an embodiment of the present invention including the step of measuring a level of an anti-S-C antibody, or a diagnosis method of an embodiment of the present invention including the step of correcting a level of an anti-fusion protein antibody by a level of an anti-CAML antibody. The above diagnosis method of an embodiment of the present invention makes it possible to not only reduce a technical difficulty of diagnosis but also reduce the influence of non-specific binding. Further, use of an anti-CAML antibody prepared from a non-human animal such as a mouse can make it easier to introduce an automated means such as an image analyzer (see Example 4).

(Diagnosis of Mood Disorder Caused by Other Disease)

Each of the above-described diagnosis methods in accordance with an embodiment of the present invention can also be applied to diagnosis of a mood disorder associated with an inflammatory bowel disease and/or a chronic respiratory illness. It is known that an inflammatory bowel disease and a chronic respiratory illness are each highly-frequently associated with a mood disorder. Patients suffering from such a disease/illness have a higher anti-SITH-1 antibody titer than healthy subjects. A mechanism of pathogenesis of such a mood disorder is considered to be, but is not limited to, a mechanism in which (i) SITH-1 is expressed in association with reactivation of HHV-6 that infects an astrocyte-like cell present in a bowel or lungs and (ii) this SITH-1 binds to CAML and thereby influences a central nerve. The mood disorder associated with an inflammatory bowel disease and/or a chronic respiratory illness is known to influence treatment and recovery of a primary disease. Accordingly, appropriately diagnosing and thereby treating such a mood disorder is also effective in treating the primary disease. In an aspect of the present invention, there is provided a diagnosis method for a mood disorder associated with an inflammatory bowel disease and/or a chronic respiratory illness in a human subject, which diagnosis method including the step of measuring a level of an anti-fusion protein antibody in a biological sample isolated from the human subject. A concrete aspect of the present invention may be a diagnosis method for a mood disorder, which diagnosis method including the step of measuring a level of an anti-fusion protein antibody in a biological sample isolated from a subject patient who has been diagnosed as having an inflammatory bowel disease and/or a chronic respiratory illness. Note that the inflammatory bowel disease is preferably Crohn's disease.

(Use of Diagnosis Result Obtained by Diagnosis Method for Mood Disorder)

It is possible to use, as one information material for diagnosis of a mood disorder, a diagnosis result obtained by carrying out the above-described diagnosis method. That is, it is possible to determine whether or not a treatment is necessary on the basis of the diagnosis result obtained by carrying out the above-described diagnosis method, and to provide a treatment if necessary. A treatment method can be a treatment method described in the following [8. Treatment method for mood disorder].

[7. Diagnosis Kit for Diagnosis of Mood Disorder]

An embodiment of the present invention provides a diagnosis kit for diagnosis of a mood disorder. The term "kit" in an embodiment of the present invention is not particularly limited in concrete configuration, material, instrument and others, provided that the kit is designed for carrying out the measurement method, the method of obtaining data, or the diagnosis method.

In one aspect of the present invention, there is provided a diagnosis kit for carrying out the above diagnosis method, which kit includes at least one and preferably two or more of substances selected from an S-C protein, a C-S protein, and a CAML protein.

The diagnosis kit in accordance with an embodiment of the present invention may be, but is not limited to, a diagnosis kit for carrying out the above diagnosis method, which kit includes at least one and preferably two or more of supports selected from a support to which an S-C protein is immobilized, a support to which a C-S protein is immobilized, and a support to which a CAML protein is immobilized, and more preferably, at least a support to which the S-C protein is immobilized and a support to which the CAML protein is immobilized. By use of such supports, for example, so-called "multiplex assay" can be suitably performed, in which "multiplex assay" a plurality of antibodies are detected at a time from one biological specimen. Further, in one aspect of the present invention, there is provided a diagnosis kit for carrying out the above diagnosis method, which kit includes a support to which at least one or preferably two or more of substances selected from an S-C protein, a C-S protein, and a CAML protein, and to which more preferably, at least the S-C protein and the CAML protein are immobilized.

The diagnosis kit in accordance with an embodiment of the present invention further include, as needed, at least one of: various reagents and instruments (buffer solution, pipette, etc.) for use in detection of an anti-fusion protein antibody; various reagents and instruments (test tube, buffer solution, etc.) for preparation of a sample (target for measurement); a manual of a detection kit; a control sample for use in measurement; and data for comparison for use in analysis of detection results. The control sample can be, for example, a sample obtained by appropriately adjusting, in accordance with the purpose of diagnosis, the level of the anti-S-C antibody, the level of the anti-C-S antibody, and/or the level of the anti-SITH-1 antibody. These antibody levels are adjusted in view of (i) a quantitative value (normal value) of a healthy subject, (ii) a quantitative value (disease value) of a typical mood disorder patient, or (iii) a quantitative value (disease value) of a mild mood disorder patient, a moderate mood disorder patient, or a severe mood disorder patient. Such a sample can be prepared by processing a biological sample of serum, plasma, nasal discharge, saliva, or the like of a healthy subject or a mood disorder patient, though preparation of the sample is not limited to such preparation. The sample itself prepared as above is also one aspect of the present invention. The manual of the detection kit includes the contents of the measurement method in accordance with an embodiment of the present invention as discussed above in the section entitled [5. Method for measuring level of anti-fusion protein antibody].

[8. Treatment Method for Mood Disorder]

An embodiment of the present invention further provides a treatment method for a mood disorder. This treatment method includes administering an HHV-6 infection inhibitor and/or an HHV-6 inhibitor.

An embodiment of the present invention provides a treatment method for a mood disorder, which method includes administering an HHV-6 infection inhibitor and/or an HHV-6 inhibitor to a human subject who has been diagnosed to be in need of treatment, as a result of measurement of a level of an anti-fusion protein antibody in accordance with an embodiment of the present invention in a biological sample isolated from a human subject. In one embodiment, measurement of an antibody level and diagnosis are performed by the measurement method and the diagnosis method in accordance with embodiments of the present invention. In one example, there is provided a treatment method for a mood disorder, which method is arranged such that an HHV-6 infection inhibitor and/or HHV-6 inhibitor is administered to a human subject who has been diagnosed to be in need of treatment since the antibody level obtained in the above measurement step is higher than a specified value (e.g., a cutoff value calculated from a control).

Further, in another embodiment, the treatment method in accordance with an embodiment of the present invention includes the step of administering the HHV-6 infection inhibitor to olfactory epithelium cells of a human subject. Such administration of the HHV-6 infection inhibitor to olfactory epithelium cells makes it possible to inhibit HHV-6 infection of the olfactory epithelium cells.

The inventors of the present invention have found the above-described mechanism of pathogenesis of the mood disorder (Patent Literature 3). This mechanism of pathogenesis is supported by the knowledge as below which has been obtained by the inventors of the present invention. Note that the present invention is not limited to this mechanism of pathogenesis.

When the inventors of the present invention expressed SITH-1 genes in olfactory epithelium cells (which refer to cells in olfactory epithelium including olfactory ensheathing cells in the present specification) of mice, the mice (hereinafter referred to as "SITH-1-expressing mice") experienced impairment of olfactory cells and further experienced stress vulnerability, and consequently developed a mood disorder.

Examples of the impairment of the olfactory cells encompass apoptosis of olfactory bulb cells. Olfactory bulbs of the SITH-1-expressing mice exhibited larger increases of expression of apoptosis-related genes than those of the control mice (see Example 7). In addition, in observation of tissue of the olfactory bulbs by TUNEL staining, a larger number of apoptotic cells were detected in the SITH-1-expressing mice (see Example 7).

In addition, abnormal production of CRH (corticotropin-releasing hormone) and urocortin was observed in the whole brains of the SITH-1-expressing mice (see Example 7). Since CRH and urocortin are biomarkers of hypothalamus, abnormal production thereof strongly suggested that some kind of abnormalities occurred in the hypothalami. Furthermore, increases in expression level of REDD1, which is a stress response factor in a brain, were also observed (see Example 7).

Then, when the SITH-1-expressing mice were subjected to mild stress, the SITH-1-expressing mice exhibited symptoms of a mood disorder (see Example 7). This suggested that the SITH-1-expressing mice exhibited stress vulnerability. Note that stress vulnerability refers to a state in which a proper response cannot be made to a low level of stressor.

It was further found as a result of behavioral abnormality tests (tail suspension tests) that the SITH-1-expressing mice had a prolonged period of immobility time, and were therefore in a depressive state (see Example 7). These behavioral abnormalities were improved by administration of selective serotonin reuptake inhibitor (SSRI) (see Example 7).

Based on a set of these results, the inventors of the present invention have found the above mechanism of pathogenesis for development of a mood disorder caused by HHV-6.

The inventors of the present invention thus found that the infection of olfactory epithelium cells with HHV-6 causes expression of SITH-1, and this consequently causes a variety of impairment. Note that "impairment" herein refers to impairment of olfactory cells, an abnormality of hypothalamus, abnormal expression of a stress response factor in a brain, stress vulnerability, and a mood disorder.

Examples of the impairment of the olfactory cells encompass, but are not limited to, an increase in apoptosis of the olfactory cells. Examples of the abnormality of the hypothalamus encompass, but are not limited to, abnormal production of CRH and/or urocortin. Examples of the stress response factor in the brain which are abnormally expressed encompass, but are not limited to, REDD1.

(Target of Treatment Method)

A target of the treatment method in accordance with an embodiment of the present invention is a human subject who have been determined, according to the diagnosis method for a mood disorder in accordance with an embodiment of the present invention, (i) to have a mood disorder, (ii) to be in a depressive state that does not satisfy the diagnostic criteria of a mood disorder, (iii) to have the risk of showing a depressive state in the future or the risk of developing a mood disorder in the future, (iv) to have a predisposing factor for a mood disorder, and/or (v) to have been provided with an insufficient effect of treatment given for a mood disorder. The mood disorder here preferably does not include a temporary depressive state caused by a stressor. In a human subject having a high level of an anti-fusion protein antibody, it is highly likely that a mood disorder has been developed via the above mechanism. The treatment method in accordance with an embodiment of the present invention makes it possible to prevent olfactory epithelium cells of such a human subject from being frequently infected with HHV-6 and to thereby reduce deterioration of a symptom.

Further, the target of the treatment method in accordance with an embodiment of the present invention may encompass (i) human subjects who have been determined to be in a depressive state that does not satisfy the diagnostic criteria for a mood disorder and/or to have a high risk of developing a mood disorder, by the diagnosis method for a mood disorder including measurement of a level of an anti-S-C antibody in accordance with an embodiment of the present invention, and (ii) human subjects who have been determined to be not in a healthy state in terms of a mood disorder and/or to have a high risk of developing a mood disorder, by the diagnosis method for a mood disorder including measurement of a level of an anti-C-S protein antibody in accordance with an embodiment of the present invention. The above human subjects have a high risk of developing a mood disorder via the above mechanism in the future. Therefore, if such a human subject is treated by the treatment method in accordance with an embodiment of the present invention, development of the mood disorder can be prevented in the human subject.

Further, the target of the treatment method in accordance with an embodiment of the present invention may be a patient who has been diagnosed as having a mood disorder caused by an inflammatory bowel disease and/or a chronic respiratory illness. The treatment in accordance with an embodiment of the present invention to such a patient is considered to not only improve the mood disorder but also lead to improvement of a primary disease.

(Treatment Agent and Administration Method)

In the treatment method in accordance with an embodiment of the present invention, an HHV-6 infection inhibitor and/or an HHV-6 inhibitor can be used as a treatment agent.

The HHV-6 infection inhibitor in accordance with an embodiment of the present invention can be any inhibitor, provided that the inhibitor can inhibit infection of cells with HHV-6. Preferable examples of the HHV-6 infection inhibitor encompass anti-HHV-6 antibodies, heparan sulfates, heparins, HHV-6 vaccines, sugar hydrolase (glycosidase) inhibitors, protease inhibitors, peptides, sugar chain-polypeptides, and sugar derivatives. More preferable examples of the HHV-6 infection inhibitor encompass heparan sulfates, heparins, and HHV-6 vaccines. These HHV-6 infection inhibitors can be combined as appropriate. Preferable examples of the anti-HHV-6 antibody encompass neutralizing antibodies.

Such an HHV-6 infection inhibitor can be administered in any form that can inhibit infection of olfactory epithelium cells with HHV-6. Preferably, the HHV-6 infection inhibitor is administered to olfactory epithelium. In actual treatment, any of these HHV-6 infection inhibitors can be administered to the olfactory epithelium by, for example, spraying a proper amount of the HHV-6 infection inhibitor into the nasal cavity.

The HHV-6 vaccine used in an embodiment of the present invention is preferably an inactivated vaccine or an attenuated vaccine, and more preferably an inactivated vaccine. An inactivated HHV-6 vaccine can be prepared by causing a virus to lose its replication capacity through a conventionally-known virus inactivation treatment, examples of which encompass (i) a chemical treatment with use of formalin and (ii) physical treatments such as those with use of heat and radiation. It is preferable to add an adjuvant to the HHV-6 vaccine as needed. A person skilled in the art can use a conventionally-known adjuvant selected as appropriate. Preferable examples of the adjuvant encompass, but are not limited to, aluminum salt adjuvants (such as aluminum hydroxide and aluminum phosphate), emulsifier adjuvants (such as CFA, IFA, squalene, and MF59), polymer fine particle adjuvants (such as liposome and biopolymer), Toll-like receptors (such as dsRNA, CpG-oligo DNA, LPS, and β-glucan), and inositol pentaphosphate.

Note that an adjuvant such as inositol pentaphosphate can be sprayed by itself into the nasal cavity without a vaccine. This causes immunity to be activated, and therefore causes an anti-HHV-6 antibody existing in the nasal cavity to be produced by a greater amount. This makes it possible to inhibit infection with HHV-6.

Alternatively, the adjuvant can be a vaccine of another virus or bacteria or an antigen of another virus or bacteria. The form can be, for example, a form in which an HHV-6 antigen is mixed with an influenza vaccine.

The vaccine used in an embodiment of the present invention is not limited to a particular one, and preferably a nasal vaccine. In a case where the HHV-6 vaccine is sprayed into a nasal mucosa so that mainly an anti-HHV-6 IgA antibody is produced in a nasal discharge, it is possible to inhibit invasion of HHV-6 from the nasal cavity into the brain. In a case where the nasal vaccine is used, it is possible to use as needed a substance for increasing adherence of the vaccine in the nasal cavity, such as a gelatinizer and/or a thickener.

A herpesvirus may go through stages of infection of a cell, latent infection, multiplication, and reactivation. It is then considered that when a human is stressed, HHV-6 causing latent infection multiplies and becomes reactivated in salivary gland, and part of HHV-6s reach olfactory epithelium cells. Accordingly, it is considered effective as treatment of a mood disorder to inhibit multiplication and reactivation of HHV-6 in salivary gland by using an HHV-6 inhibitor, though the treatment of a mood disorder is not limited thereto.

Such an HHV-6 inhibitor is preferably an anti-human herpesvirus-6 drug (anti-HHV-6 drug) or a virus reactivation inhibitor.

An action mechanism of the anti-HHV-6 drug is not limited to a particular one. Examples of the anti-HHV-6 drug encompass a virus DNA polymerase inhibitor, a protease inhibitor, a terminal transferase inhibitor, and a helicase inhibitor.

The anti-HHV-6 drug is preferably selected from the group consisting of aciclovir (GlaxoSmithKline), ganciclovir (Syntex), valganciclovir (F. Hoffmann-La Roche), foscarnet (AstraZeneca), famciclovir (Novartis) and idoxuridine (IDU) (The Journal of Immunology, 1964, 92: 550-554. Effects of 5-Idoo-2-Desoxyuridine (IDU) on Herpesvirus Synthesis and Survival in Infected Cells, Kendall O. Smith and C. Dean Dukes), but is not limited thereto.

More preferably, the anti-HHV-6 drug is preferably ganciclovir or valganciclovir. All the above anti-HHV-6 drugs are conventionally-known compounds and can be easily obtained or easily produced by a person skilled in the art.

Examples of inhibition by the virus reactivation inhibitor encompass not only direct inhibition of viral particle formation and/or virus replication but also inhibition in a preparation stage of the viral particle formation and/or the virus replication, for example, inhibition of gene expression in an intermediate stage. The virus reactivation inhibitor is selected from the group consisting of D-ribose, vitamin C and an active hexose correlated compound (Amino Up Chemical (AHCC)), though not limited thereto.

Further, substances having an antioxidant effect and/or an anti-fatigue effect often inhibit virus reactivation. Such substances therefore can be preferably used as the virus reactivation inhibitor.

Though the effects of such substances are mild, the substances have no strong side effects. Accordingly, the substances can be easily used for continuous dosing. Therefore, such substances can be preferably used for prevention of symptoms of a mood disorder of a target with no symptom of a mood disorder.

The above agents can be administered preferably together with one or more pharmaceutically acceptable carriers. Examples of such a pharmaceutically acceptable carrier encompass a diluent, a filler, an adjuvant, an excipient, and a vehicle, which are pharmaceutically acceptable depending on a route of administration, and an aqueous or oil suspension which is formulated with use of any of suitable one(s) of a dispersant, a wetter, and a suspension agent.

The pharmaceutically acceptable carrier is in general aseptic and apyrogenic, and may contain one or more of water, oil, solvent, salt, sugar and other hydrocarbon(s), emulsifier, buffer, an antibacterial agent, and a chelating agent. A specific pharmaceutically acceptable carrier and a ratio of an active compound to the carrier are determined in accordance with a solubility of a composition, a chemical property of the composition, an administration method, and standard pharmaceutical practice.

The HHV-6 inhibitor is administered to a patient by a suitable method depending on a type of the HHV-6 inhibitor to be used. For example, administration of the HHV-6 inhibitor can be salivary gland administration, intravenous administration, percutaneous administration, intracutaneous administration, intraperitoneal administration, intramuscular administration, nasal administration, epidural administration, oral administration, local administration, subcutaneous administration or any other suitable technique. In a preferred administration method, the HHV-6 inhibitor is intravenously or intraperitoneally administered and then transferred to salivary gland. A person skilled in the art can easily decide an optimum drug prescription in accordance with an intended route of administration, a delivery system and a desirable dosage amount.

The amount of the HHV-6 inhibitor to be administered depends on age, conditions subject to treatment, weight, a desirable period of treatment, an administration method and other parameter(s). An effective dosage is decided routinely by a doctor or other qualified medical expert. Preferably, the HHV-6 inhibitor is used in a normal administration amount of the HHV-6 inhibitor.

[9. Recombinant Expression Vector]

An embodiment of the present invention further provides a recombinant expression vector including a gene encoding a fusion protein. A type of the vector can be, for example, (i) a vector (e.g., plasmid) that autonomously replicates or (ii) a vector that, when the vector is introduced into a host cell, is incorporated into a genome of the host cell and replicated together with a chromosome into which the vector has been incorporated.

The recombinant expression vector can be prepared by using, for example, a plasmid, a phage, a cosmid, or the like, but the recombinant expression vector is not limited thereto. Further, the recombinant expression vector may be prepared by using a conventionally-known preparation method. The recombinant expression vector is not limited to any specific type, and a vector which can be expressed in a host cell can be selected as appropriate. That is, the recombinant expression vector may be one prepared by (i) appropriately selecting a promoter sequence depending on a kind of a host cell so that a gene will be expressed without fail and (ii) incorporating the promoter sequence and a gene encoding the fusion protein in a plasmid of various kinds. Examples of the recombinant expression vector encompass: phage vectors; plasmid vectors; virus vectors; chromosome vectors; episome vectors; and virus-derived vectors and viruses (e.g., baculoviruses, papovaviruses, vaccinia viruses, adenoviruses, adeno-associated viruses, avipoxviruses, pseudorabies viruses, herpesviruses, lentiviruses, and retroviruses), and vectors derived from combinations thereof (e.g., cosmids and phagemids).

Generally, introduction of the plasmid vector is performed in sediments such as calcium phosphate sediments or in a complex with charged lipids. In a case where the vector is a virus, the vector can be packaged in vitro using an appropriate packaging cell line, and can subsequently be introduced into a host cell. A retrovirus vector may be replicable or replication-defective. In the latter case, multiplication of the virus generally occurs only in a complementary host cell.

Further, vectors each including a cis-acting regulating region for a target gene are preferable. An appropriate trans-acting factor may be supplied by a host, by a complementary vector, or by the vector itself during introduction of the vector into the host. In a preferable embodiment in this regard, vectors each providing specific expression which may be inducible and/or cell-type specific are preferable. Particularly preferred among such vectors are those inducible by environmental factors that are easy to manipulate, such as temperature and nutritional additives.

Examples of a preferable bacteria vector to be used encompass: pQE70, pQE60, and pQE-9 (available from Qiagen); pBS vector, Phagescript vector, Bluescript vector, pNH8A, pNH16a, pNH18A, pNH46A (available from Stratagene); and ptrc99a, pKK223-3, pKK233-3, pDR540, pRIT5 (available from Phrmacia). Further, examples of a preferable eukaryote vector encompass pWLNEO, pSV2CAT, pOG44, pXT1, and pSG (available from Stratagene); and pSVK3, pBPV, pMSG, and pSVL (available from Phrmacia).

Various kinds of markers may be used to confirm whether or not the gene of an embodiment of the present invention has been transferred into the host cell, and to confirm whether or not the gene is expressed in the host cell without fail. That is, the expression vector preferably includes at least one selection marker. Examples of such a selection marker encompass: a dihydrofolic acid reductase gene or neomycin resistance gene for eukaryote cell culture; and drug resistance genes such as a tetracycline-resistant gene and an ampicillin-resistance gene for culture of *E. coli* and other bacteria. Another example uses, as a marker, a gene deleted in a host cell, and introduces, as an expression vector, a plasmid or the like including the marker and the gene of an embodiment of the present invention into the host cell. From expression of the marker gene, it is possible to confirm that the gene of an embodiment of the present invention has been transferred. Alternatively, the protein of an embodiment of the present invention may be expressed as a fusion protein. For example, with Green Fluorescent Protein (GFP) derived from *Aequorea victoria* used as a marker, the protein of an embodiment of the present invention may be expressed as a GFP fusion protein. Further, the gene of an embodiment of the present invention may be bound to a vector including a selection marker for multiplication in the host cell.

Further, it is preferable that a DNA insert is operably linked to an appropriate promoter (e.g., phage APL promoter, *E. coli* lac promoter, trp promoter, tac promoter, SV40 early promoter and late promoter, and a promoter of retrovirus LTR). As another appropriate promoter, any one conventionally known to a person skilled in the art can be used.

In an embodiment of the present invention, conventionally-known bacteria promoters which are suitably used encompass *E. coli* lad and lacZ promoters, T3 promoter and T7 promoter, gpt promoter, λPR promoter and APL promoter, and trp promoter. Suitable eukaryote promoters encompass CMV immediate-early promoter, HSV thymidine kinase promoter, early SV40 promoter and late SV40 promoter, a promoter of retrovirus LTR (e.g., a promoter of Rous sarcoma virus (RSV)), and metallothionein promoter (e.g., mouse metallothionein I promoter).

Further, in an embodiment of the present invention, examples of conventionally-known promoters suitably used for mammal cells encompass a promoter including a cytomegalovirus enhancer and a chicken β-actine promoter, EF-1α promoter, and Tet-on or Tet-off promoter.

It is preferable that the recombinant expression vector further includes: sites for transcription start and transcription termination; and a transcription region containing a ribosome-binding site for translation. A matured transcript expressed by a vector construct includes a coding region containing (i) transcription start AUG at the start of a polypeptide to be translated and (ii) a stop codon which is properly positioned at the end of the polypeptide.

Transcription of DNA by a higher eukaryote may be enhanced by insertion of an enhancer sequence into a vector. The enhancer is a DNA cis-acting element (generally, approximately 10 bp to 300 bp) which works for enhancing transcriptional activity of a promoter of a predetermined host cell type. Examples of the enhancer encompass: SV40 enhancer (positioned at 100 bp to 270 bp on the late side of a replication origin); an early promoter enhancer of a cytomegalovirus; a polyoma enhancer on the late side of a replication origin; and an adenovirus enhancer.

The above host cell is not limited to any specific one, and a conventionally-known cell of various kinds may suitably be used. Typical examples of an appropriate host encompass: bacterial cells (e.g., *E. coli* cells, *Streptomyces* cells, and *Salmonella typhimurium* cells); fungus cells (e.g., yeast cells); insect cells (e.g., *Drosophila* S2 cells and *Spodoptera* Sf9 cells); animal cells (e.g., human-derived cells, monkey-derived cells, HEK293T cells, HO cells, COS cells, and Bowes melanoma cells); and plant cells. Note that the human-derived cells may be cells that can be infected by HHV-6 (glial cells, macrophages, etc.) or cells that cannot be infected by HHV-6. More concrete examples of the appropriate host encompass not only mammal cells such as human cells and mouse cells but also cells derived from *Bombys mori*, insects such as *Drosophia melanogaster*, bacteria such as *E. coli* (*Escherichia coli*), yeasts (*Saccharomyces cerevisiae* and *Schizosaccharomyces pombe*), and *Caenorhabditis elegans*, and oocytes of *Xenopus laevis*. However, the appropriate host is not limited to these. A culture medium and conditions suitable for each of the above host cells may be ones conventionally-known in the art.

A method for introducing the expression vector into the host cell, i.e., a method for transformation is also not limited to any specific one, and a conventionally-known method may suitably be used. Examples of such a conventionally-known method encompass electroporation, a calcium phosphate method, a liposome method, a DEAE dextran method, microinjection, cationic lipid-mediated transfection, electroporation, transduction, infection or a method using cardiolipin. These methods are described in many standard laboratory manuals, for example, Davis et al., Basic Methods In Molecular Biology (1986).

[10. Transformed Cell]

Further, an embodiment of the present invention provides a transformed cell in which a fusion protein is produced. The transformed cell can be prepared by introducing a gene encoding the fusion protein into a host cell. Specifically, the transformed cell can be prepared by introducing, into the above-described host cell, the polynucleotide in accordance with an embodiment of the present invention or the recombinant expression vector in accordance with an embodiment of the present invention (collectively referred to as a nucleic-acid construct of an embodiment of the present invention).

Cells are Preferably Human Cells.

The gene encoding the fusion protein is introduced into the host cell by a method as described above in the section entitled [9. Recombinant expression vector]. The method is appropriately selected depending on each cell kind.

The transformed cell above can be cultured in an appropriate culture medium under conditions that allows for expression of a nucleic-acid construct having been introduced. It is possible to subsequently isolate and purify, as needed, the fusion protein in accordance with an embodiment of the present invention from a culture product of the transformed cell.

Further, an embodiment of the present invention provides a mood disorder model animal in which the fusion protein is produced in olfactory epithelium cells. According to the above mechanism of pathogenesis of a mood disorder, a mood disorder is developed in animals in which the fusion protein is produced in the olfactory epithelium cells. Such a mood disorder model animal can be prepared by introduction of the gene encoding the fusion protein into the olfactory epithelium cells of the animal with use of the vector of an embodiment of the present invention. The fusion protein is preferably an S-C protein. An animal into which the fusion protein is to be introduced is not limited to any particular one, provided that the animal can be used as a laboratory animal. The animal is preferably a mammal. Examples of the animal encompass mice, rats, and monkeys. A model animal in accordance with an embodiment of the present invention can be suitably used for, for example, (i) studies of mood disorder treatment methods, (ii) studies and determination of effects of drugs, and (iii) assessment of treatment methods (e.g. thermotherapy) for a mood disorder other than methods in which drugs are used.

[11. Exemplification of Concrete Aspects of Present Invention]

The present invention may encompass the following invention group.

(1) A fusion protein including a SITH-1 protein and a CAML protein.

(2) The fusion protein as set forth in (1), wherein: an N-terminal side of the CAML protein is bound to a C-terminal side of the SITH-1 protein.

(3) The fusion protein as set forth in (1), wherein: a C-terminal side of the CAML protein is bound to an N-terminal side of the SITH-1 protein.

(4) A support to which a fusion protein described above in any one of (1) to (3) is immobilized.

(5) An antibody detection instrument using, as a probe, a fusion protein described above in (2) or (3) or fusion proteins described above in (2) and (3).

(6) A measurement method including the step of: measuring, by using a fusion protein described above in (1), a level of the anti-fusion protein antibody in a biological sample isolated from a subject.

(7) The measurement method as set forth in (6), further including the step of: reacting a labeled anti-CAML antibody with a cell in which the fusion protein described above in (1) is expressed.

(8) A diagnosis method for a mood disorder in a human subject, including the step of: measuring an antibody level in a biological sample isolated from the human subject, the antibody level being a level of an antibody (anti-fusion protein antibody) recognizing a fusion protein described above in (1).

(9) The diagnosis method as set forth in (8), further including the step of: measuring a level of an antibody (anti-fusion protein antibody) recognizing a fusion protein described above in (2).

(10) The diagnosis method as set forth in (9), using the fusion protein described above in (2).

(11) The diagnosis method as set forth in (8), further including the step of: measuring a level of an antibody (anti-fusion protein antibody) recognizing a fusion protein described above in (3).

(12) The diagnosis method as set forth in (11), using the fusion protein as described above in (3).

(13) The diagnosis method as set forth in (8), further including the step of: measuring a level of an anti-CAML antibody in the biological sample isolated from the human subject.

(14) Use of a fusion protein described above in (1), for diagnosis of a mood disorder.

(15) A diagnosis kit for carrying out a diagnosis method described above in (8), including an antibody detection instrument described above in (15).

(16) A diagnosis kit for a mood disorder, including at least two selected from:
  (i) a fusion protein described above in (2);
  (ii) a fusion protein described above in (3); and
  (iii) a CAML protein.

(17) A nucleic acid encoding a fusion protein described above in (2) or (3).

(18) A recombinant expression vector including a nucleic acid described above in (17).

(19) A transformed cell into which a nucleic acid described above in (17) is introduced.

(20) A treatment method for a mood disorder, including the step of: administering either or both of an HHV-6 infection inhibitor and an HHV-6 inhibitor to a human subject having a high antibody level, the high antibody level being a result of measurement of an antibody level in a biological sample isolated from the human subject, the antibody level being a level of an antibody (anti-fusion protein antibody) recognizing a fusion protein described above in (1).

(21) The treatment method as set forth in (20), wherein: the HHV-6 infection inhibitor is administered to olfactory epithelium cells of the human subject.

(22) A method for producing a soluble conjugate of a SITH-1 protein and a CAML protein, the method including the step of obtaining a soluble fusion protein by fusion of the SITH-1 protein and the CAML protein.

(23) A diagnosis method for a mood disorder, including the steps of: measuring an anti-SITH-1 antibody level in a biological sample isolated from a human subject; and measuring an anti-CAML antibody level in the biological sample.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments. The following description will discuss an embodiment of the present invention in more detail with reference to Examples. Note, however, that the present invention is not limited to only these Examples.

EXAMPLES

Example 1: Signal Enhancement by Use of Fusion Protein (1.1 Observation by Indirect Fluorescent Antibody Method (IFA))

Figure 1:
FIG. 1 is a diagram illustrating structures of fusion proteins in accordance with Example 1 of the present invention.
Figure 1:
Figure 1:
Figure 1:
Figure 1:
Figure 1:

Plasma, obtained from a patient who was anti-SITH-antibody positive and diagnosed as having a mood disorder, was diluted by a factor of 40 with PBS/2% BSA 0.05% Tween 20 and then stained by use of an indirect fluorescent antibody method (IFA). Used as secondary antibodies were Alexa Fluor 488 goat anti-human secondary antibodies (Molecular Probes) diluted by a factor of 200 with PBS/2% BSA 0.05% Tween 20. Used as expression plasmids for antigens were plasmids each obtained by inserting a respective one of CAML, SITH-1, SITH-CAML, and CAML-SITH, constructed as shown in FIG. 1, between a CMV promoter and a FLAG tag of pCMV-FLAG-5a. LITMUS28i was used as a control. Each plasmid was transfected, by use of Lipofectamine LTX (Invitrogen), into HEK293T cells that were cultured on Lab-Tek chamber slides (Nuns). The transfected cells were then cultured for hours, fixed by drying, subsequently fixed for 5 minutes at −20° C. with 5% methanol-added acetone. Then, the preparations thus processed were then used as IFA antigens. Upon observing these antigens via indirect fluorescent antibody method (IFA) with use of a fluorescence microscope, it was found that the anti-SITH-1 antibody signal was enhanced when SITH-CAML and CAML-SITH were used as an antigen (see FIG. 2).

FIG. 1 is a diagram illustrating structures of fusion proteins (S: spacer, His: histidine tag).

Figure 2:
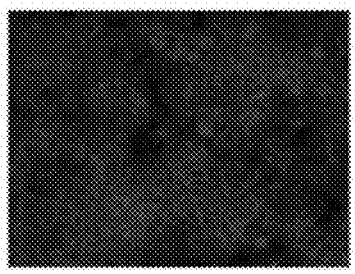
FIG. 2 shows results of observation with use of a fluorescence microscope, which results indicate enhancement of an anti-SITH-1 signal by use of fusion proteins in accordance with Example 1 of the present invention.
Figure 2:
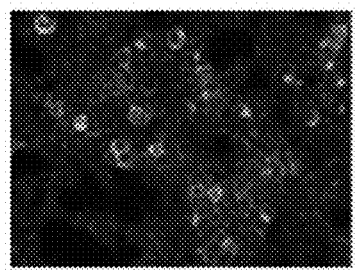
Figure 2:
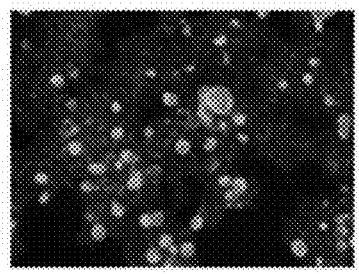
Figure 2:
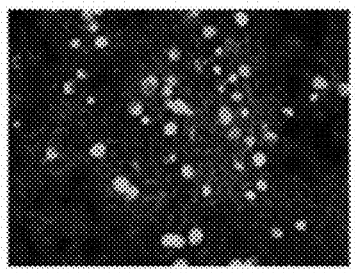
Figure 2:
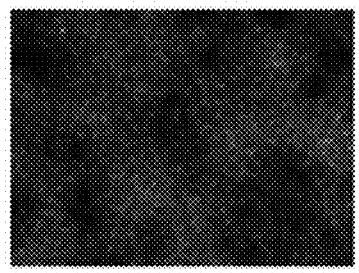

FIG. 2 shows results of observation with use of a fluorescence microscope, which results indicate enhancement of an anti-SITH-1 signal by use of the fusion proteins.

After IFA staining was carried out via the methods described above in "(1.1 Observation by indirect fluorescent antibody method (IFA))", the image analysis software ImageJ was used to quantify the intensity of fluorescence of IFA stained cells (five cells per specimen) of sera from depression patients (22 patients) who were positive for anti-SITH-1 antibody. In each quantification, a background value (i.e., the numeric value for the entire visual field under fluorescence microscope of cells transfected with the LITMUS28i cloning plasmid) was subtracted from a mean value of fluorescence intensity values, and a resulting value was expressed as a ratio with respect to the background. After confirming via a Shapiro-Wilk test that distribution was non-normal, a significant difference test was carried out via a t test (Welch's correction).

Figure 3:
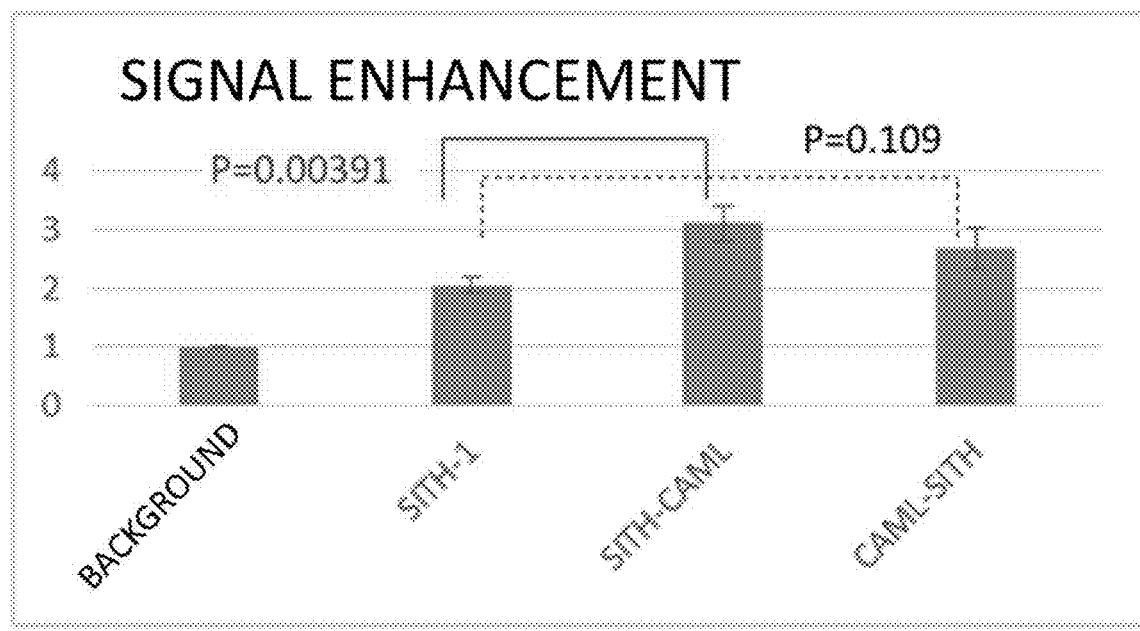
FIG. 3 illustrates enhancement of an anti-SITH-1 signal by use of fusion proteins in accordance with Example 1 of the present invention.

As a result thereof, it was found that in depression patients, signal is significantly enhanced particularly in an S-C protein (see FIG. 3).

FIG. 3 illustrates enhancement of the anti-SITH-1 signal by use of fusion proteins.

Example 2: Relationship Between (i) Conditions of Depression Patients and Persons in Depressive State and (ii) Antibodies Against Fusion Proteins In order to study the relationship between mood disorders and levels of antibodies against fusion proteins, titers of antibodies against CAML, SITH-1, and each of the fusion proteins, which antibodies were in sera, were evaluated for the following groups. Group A: anti-SITH-1 antibody positive depression patients [SITH-1(+)] (22 patients); Group B: 13 persons, who (i) did not satisfy diagnostic criteria for a mood disorder, but (ii) had a depression self-evaluation score (Beck Depression Inventory, BDI) (11 or more), for which they would be diagnosed as being in a depressive state, excluding human subjects who were determined, from supplementary information, to be in a temporary depressive state due to a stressor; and Group C: 18 persons having a BDI score of 10 or less who were presumably not in a depressive state. Evaluation of antibody titers was carried out via the IFA method described in Example 1. Quantification of the antibody titers was carried out using ImageJ, via the same method as in Example 1, and resultant values each were expressed as a ratio with respect to a background value.

Figure 4:
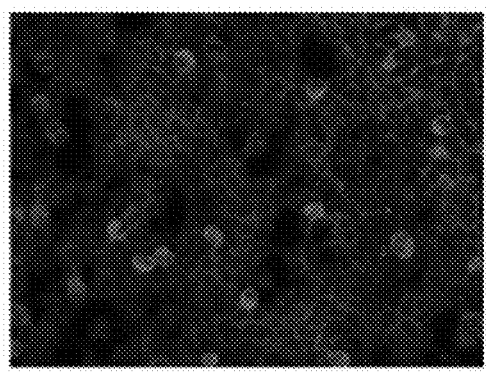
FIG. 4 illustrates the presence, in humans, of an anti-CAML antibody in accordance with Example 2 of the present invention.
Figure 4:
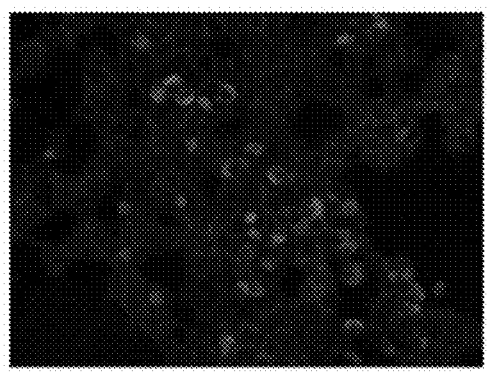

Upon studying an antibody against CAML, it was found that an anti-CAML antibody existed in all subjects. CAML is a human autoantigen, and therefore the anti-CAML antibody was presumably an autoantibody caused by an autoimmune reaction. FIG. 4 shows representative examples of results of IFA with respect to CAML.

In order to study the positive rate of anti-CAML antibody, IFA (visual inspection) and analysis of IFA by use of ImageJ were carried out. It was confirmed, via the visual inspection of IFA, that the anti-CAML antibody existed in all specimens examined. Quantification of fluorescence intensity by use of ImageJ also showed that in all subjects, fluorescence intensities with regards to CAML in subjects' sera each were higher than a background value (see FIG. 5), and that humans have the anti-CAML antibody.

Figure 6:
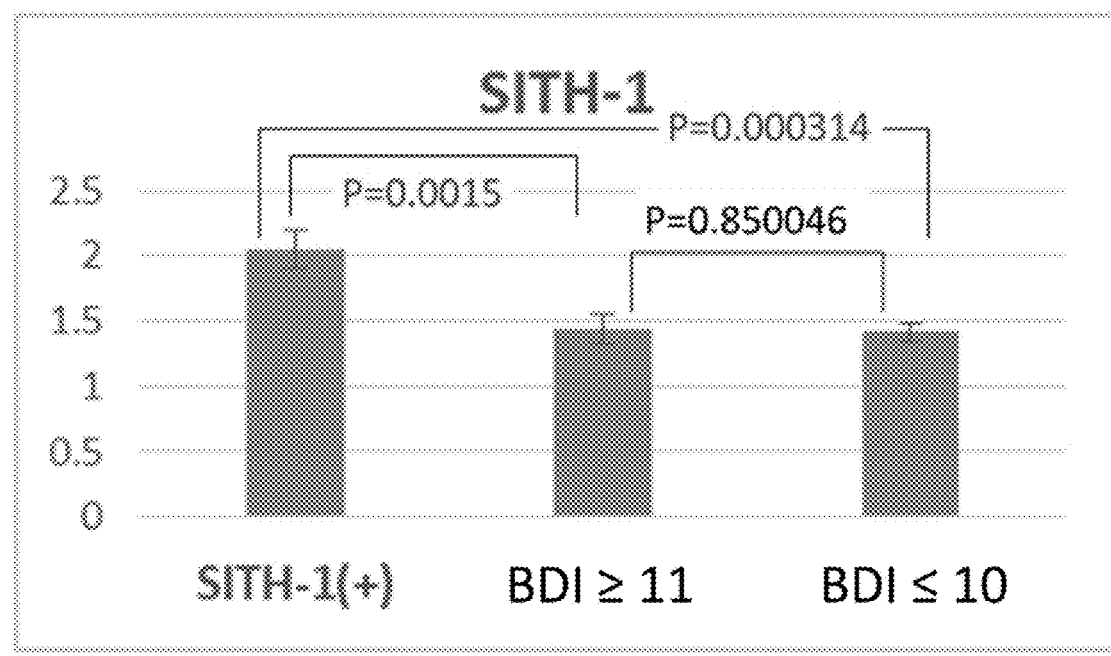
FIG. 6 shows IFA fluorescence intensities with respect to SITH-1 in sera of subjects at various stages of depression, in accordance with Example 2 of the present invention.

In the results of ImageJ analysis with regards to SITH-1, a significant difference was found between Group A and Group B (see FIG. 6). This reconfirmed the results detailed in the prior patent (Patent Literature 2), i.e., that an anti-SITH-1 antibody is useful in diagnosing depression.

Figure 7:
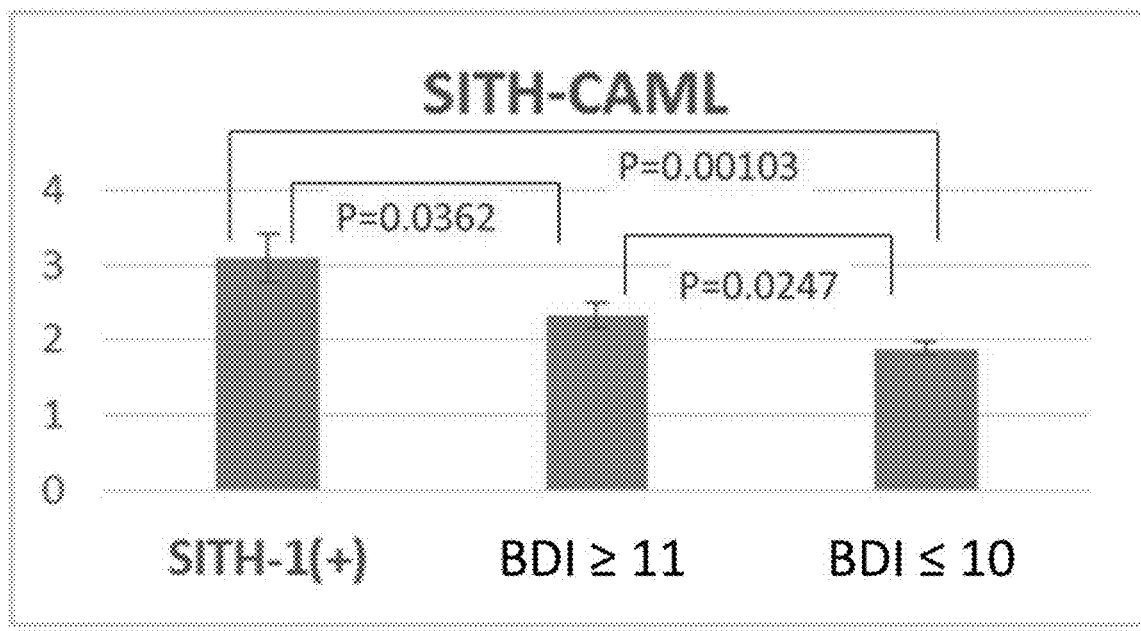
FIG. 7 shows IFA fluorescence intensities with respect to SITH-CAML in sera of subjects at various stages of depression, in accordance with Example 2 of the present invention.

In the results of ImageJ analysis with regards to the S-C protein, a significant difference was found between the depression patients (Group A) and the human subjects in a depressive state (Group B), as well as between the human subjects in a depressive state (Group B) and the healthy subjects (Group C) (see FIG. 7). This indicates that the use of the S-C protein makes it possible to detect not only a depression patient, but also a depressive state prior to onset of depression.

Figure 8:
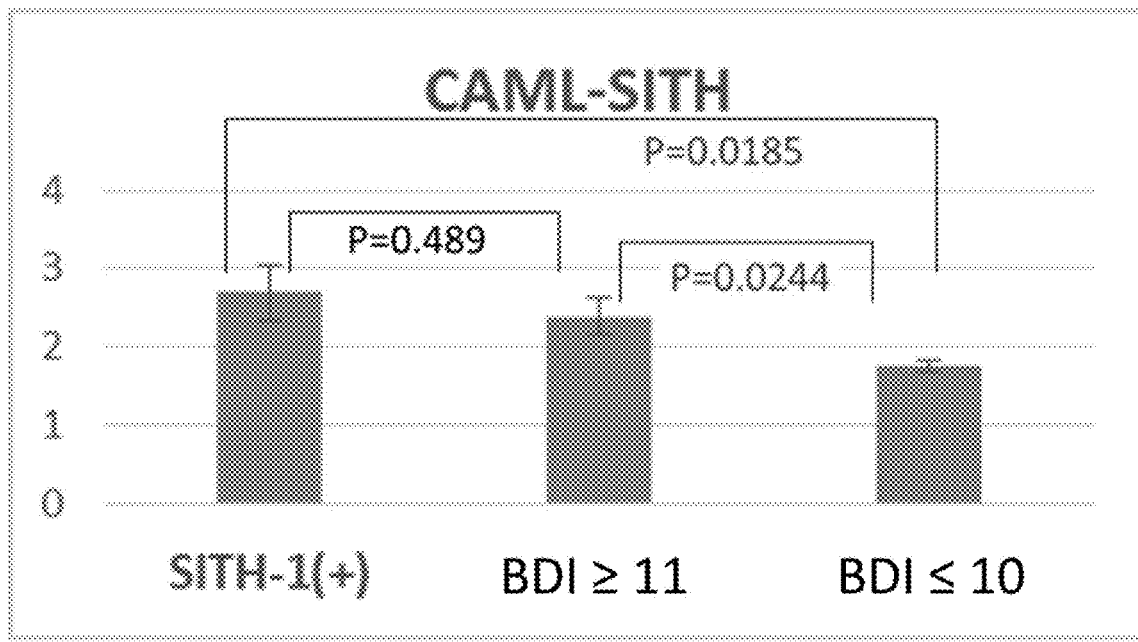
FIG. 8 shows IFA fluorescence intensities with respect to CAML-SITH in sera of subjects at various stages of depression, in accordance with Example 2 of the present invention.

Furthermore, it was surprisingly found, from the results of ImageJ analysis of cases where the C-S protein was used as an antigen, that while no significant difference was found between the depression patients (Group A) and the human subjects in a depressive state (Group B), there was a significant difference between the human subjects in a depressive state (Group B) and the healthy subjects (Group C) (see FIG. 8). These results demonstrated that testing with use of the C-S protein as an antigen makes it possible to detect a healthy subject who does not satisfy diagnostic criteria for a mood disorder but who is at a stage prior to onset of a mood disorder and who shows a depressive state.

Figure 9:
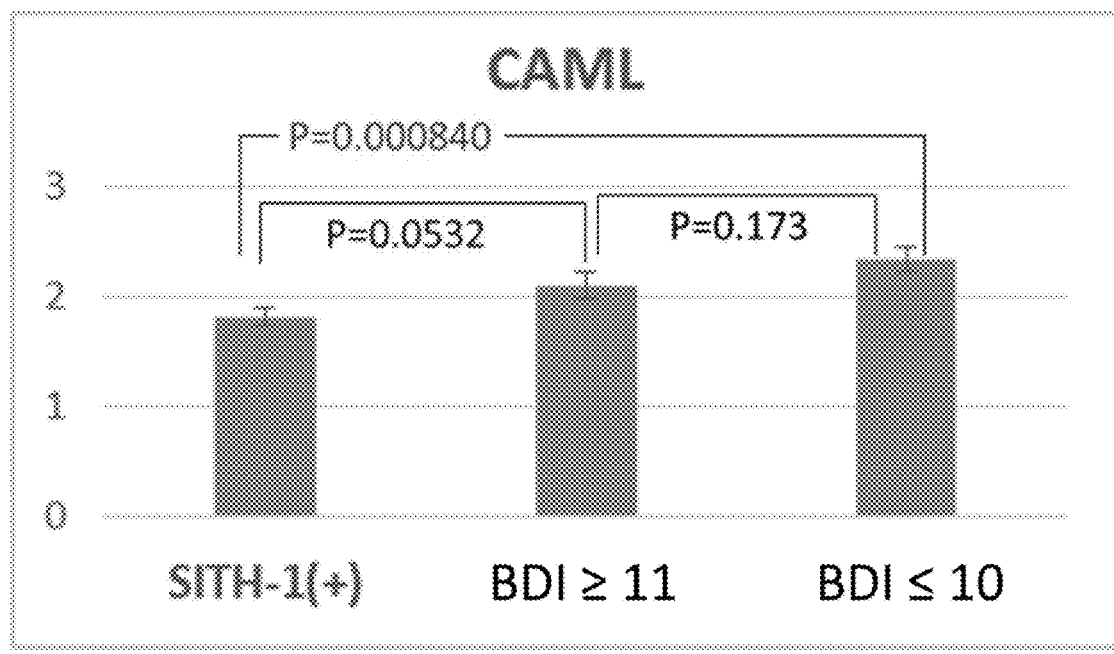
FIG. 9 shows IFA fluorescence intensities with respect to CAML in sera of subjects at various stages of depression, in accordance with Example 2 of the present invention.

Furthermore, in the results of ImageJ analysis with regards to CAML, it was observed that the depression patients (Group A) had a significantly decreased level of the anti-CAML antibody in comparison to the healthy subjects (Group C) (see FIG. 9).

The above-described results thus indicate that measuring the anti-SITH-1 antibody with use of a fusion protein does not only bring about the quantitative effect of merely increasing sensitivity in diagnosis, but also brings about the qualitative change of allowing for determination of a characteristic of a patient in diagnosis.

FIG. 4 illustrates the presence of the anti-CAML antibody in humans.

It was found, via IFA, that humans have the anti-CAML antibody, which is an autoantibody. FIG. 4 shows representative examples of IFA results.

Figure 5:
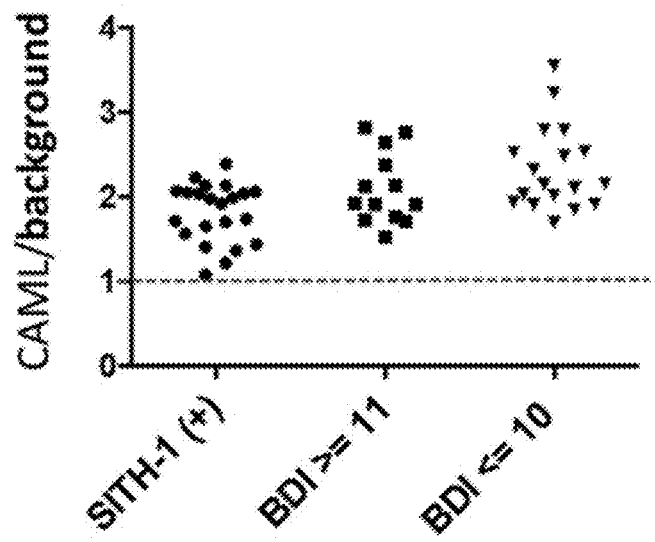
FIG. 5 shows analysis of an anti-CAML antibody with use of ImageJ, in accordance with Example 2 of the present invention.

FIG. 5 shows analysis of the anti-CAML antibody with use of ImageJ.

FIG. 5 shows ratios of (i) fluorescence intensities with respect to CAML and (ii) respectively corresponding background fluorescence intensities. In all populations, the ratios exceeded 1.

FIG. 6 shows IFA fluorescence intensities with respect to SITH-1 in sera of subjects at various stages of depression. FIG. 6 shows ratios with respect to respective background values. For subjects other than the depression patients, no signal was detected with respect to SITH-1. As such, for convenience, the background value of cells transfected with SITH-1 was used as the value for SITH-1. After confirming via a Shapiro-Wilk test that distribution was non-normal, a significant difference test was carried out via a t test (Welch's correction).

FIG. 7 shows IFA fluorescence intensities with respect to SITH-CAML in sera of subjects at various stages of depression. FIG. 7 shows ratios with respect to respective backgrounds. After confirming via a Shapiro-Wilk test that distribution was non-normal, a significant difference test was carried out via a t test (Welch's correction).

FIG. 8 shows IFA fluorescence intensities with respect to CAML-SITH in sera of subjects at various stages of depression. FIG. 8 shows ratios with respect to respective background values. After confirming via a Shapiro-Wilk test that distribution was non-normal, a significant difference test was carried out via a t test (Welch's correction).

FIG. 9 shows IFA fluorescence intensities with respect to CAML in sera of subjects at various stages of depression. FIG. 9 shows ratios with respect to respective background values. After confirming via a Shapiro-Wilk test that distribution was non-normal, a significant difference test was carried out via a t test (Welch's correction).

Example 3: Improvement of Depression Diagnosis Performance by Combination of SITH-1 with CAML or Combination of Fusion Protein with CAML In Example 3, it was studied whether diagnosis performance could be further improved by combining the use of CAML with a measurement method using SITH-1 or a fusion protein.

Specifically, in Example 3, fluorescence intensity with respect to CAML was used instead of background in the method described in Example 2. Diagnosis performance was then examined for cases where a ratio was calculated between this fluorescence intensity with respect to CAML and each of the respective fluorescence intensities with respect to SITH-1, the S-C protein, and the C-S protein.

Figure 10:
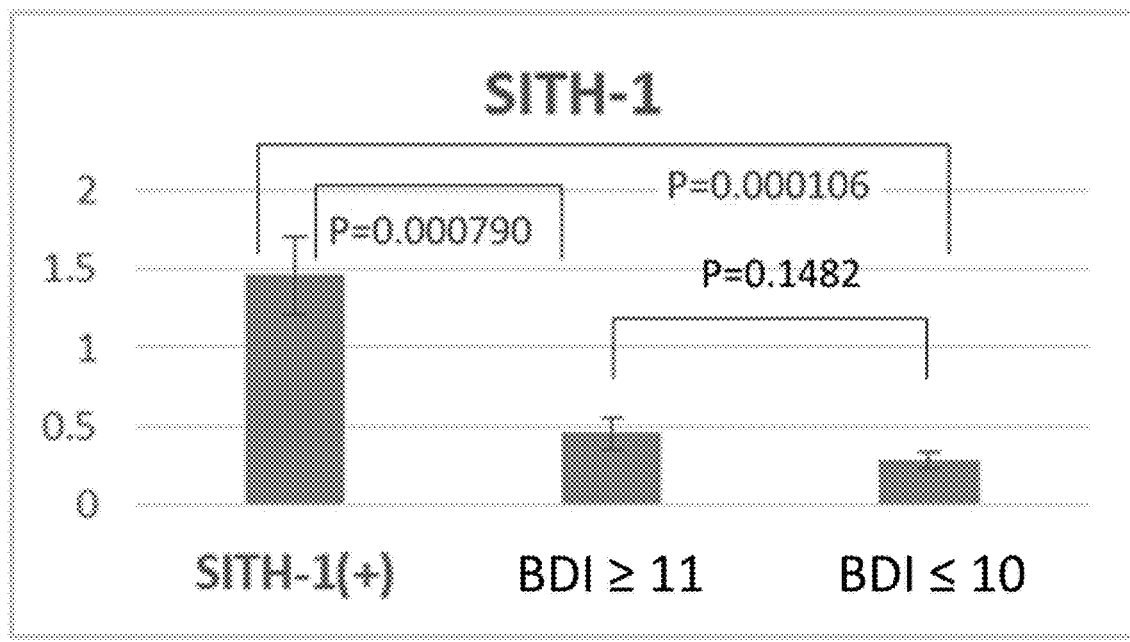
FIG. 10 shows IFA fluorescence intensities with respect to SITH-1 in sera of subjects at various stages of depression, in accordance with Example 3 of the present invention.

FIG. 10 shows a relationship between (i) the ratio between IFA fluorescence intensities of SITH-1 and CAML and (ii) depression or a depressive state. In FIG. 10, the P value of the significant difference test between SITH-1 positive depression patients and subjects in a depressive state (BDI 11) was decreased with respect to the P value seen in FIG. 6.

Figure 11:
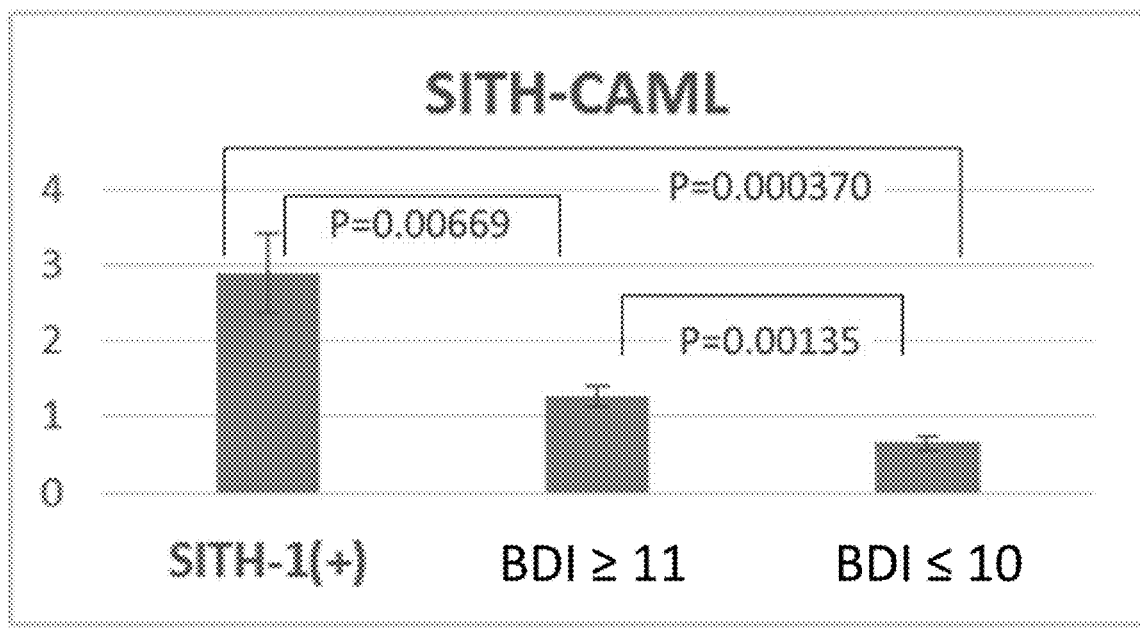
FIG. 11 shows IFA fluorescence intensities with respect to SITH-CAML in sera of subjects at various stages of depression, in accordance with Example 3 of the present invention.

FIG. 11 shows the results of a similar study regarding the S-C protein. In FIG. 11, the P value of the significant difference test between Group A and Group B, and the P value of the significant difference test between Group B and Group C were both markedly less than the P values seen in FIG. 7. This confirmed that a combination of the S-C protein and CAML greatly improved diagnostic ability.

Figure 12:
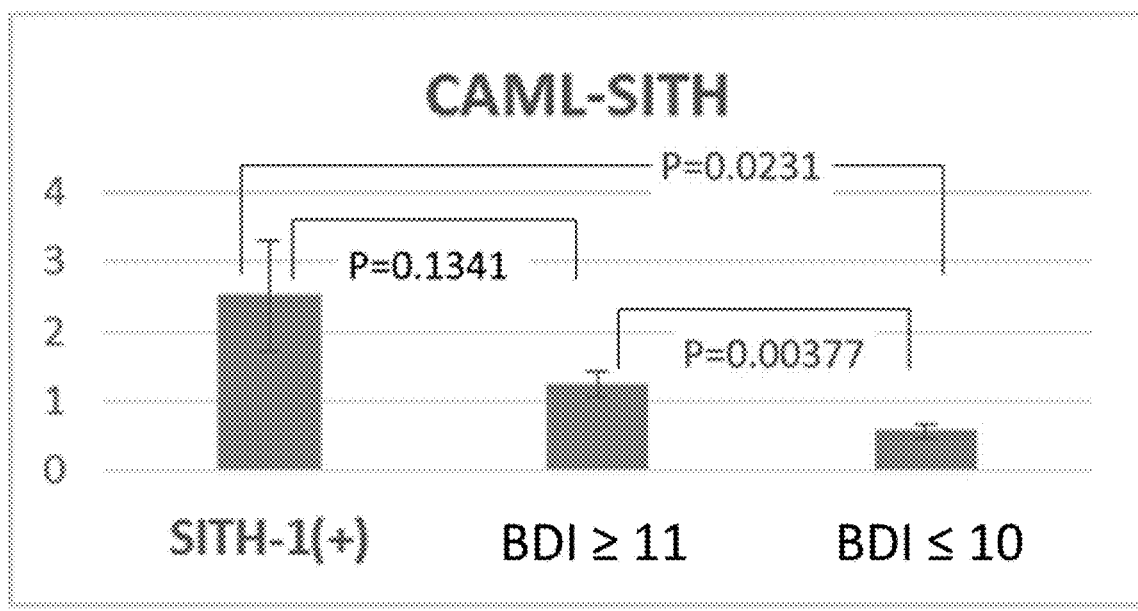
FIG. 12 shows IFA fluorescence intensities with respect to CAML-SITH in sera of subjects at various stages of depression, in accordance with Example 3 of the present invention.

FIG. 12 shows the results of a similar study regarding the C-S protein. In FIG. 12, the P value of the significant difference test between Group B and Group C was markedly less than the P value seen in FIG. 8. As such, it was found that there was a great improvement in the ability to distinguish between a depressive state and a healthy state. At the same time, there was no significant difference in the P value for the significant difference test between Group A and Group B. As such, the property of the C-S protein test having specificity toward distinguishing between a healthy state and a depressive state remained unchanged.

The inventors have shown, in a separate pending patent application (Patent Literature 3), that it is possible to prevent or treat depression or a mood disorder caused by SITH-1 by use of an HHV-6 inhibitor or by preventing olfactory epithelium cells from being infected with HHV-6 in saliva. An antibody against the C-S protein appears at the earliest stage of a depressive state or depression relating to SITH-1, or when symptoms are the mildest. As such, it is thought that a test for the antibody against the C-S protein is extremely important as an index for prevention and early treatment of disorders relating to SITH-1, such as depression, a depressive state, a mood disorder, and a mood disorder caused by Crohn's disease.

FIG. 10 shows IFA fluorescence intensities with respect to SITH-1 in sera of subjects at various stages of depression. FIG. 10 shows ratios with respect to CAML. For subjects other than depression patients, no signal was detected with respect to SITH-1. As such, for convenience, a background value of cells transfected with SITH-1 was used as the value for SITH-1. After confirming via a Shapiro-Wilk test that distribution was non-normal, a significant difference test was carried out via a t test (Welch's correction).

FIG. 11 shows IFA fluorescence intensities with respect to SITH-CAML in sera of subjects at various stages of depression. FIG. 11 shows ratios with respect to CAML. After confirming via a Shapiro-Wilk test that distribution was non-normal, a significant difference test was carried out via a t test (Welch's correction).

FIG. 12 shows IFA fluorescence intensities with respect to CAML-SITH in sera of subjects at various stages of depression. FIG. 12 shows ratios with respect to CAML. After confirming via a Shapiro-Wilk test that distribution was non-normal, a significant difference test was carried out via a t test (Welch's correction).

Example 4: Standardizing and Improving Efficiency of Depression Examination Using Fusion Protein and CAML As described above, it was clearly found that correcting the IFA fluorescence intensity of an antibody against a fusion protein by use of the IFA fluorescence intensity of a serum antibody against CAML improved the performance of diagnosis of depression and a depressive state. Double staining of the S-C protein and the C-S protein with use of an anti-CAML antibody produced in a rabbit or the like and an antibody against a fusion protein in combination makes it possible to, for example, confirm (i) transfection efficiency, (ii) a protein expression level, and/or (iii) a measurement site at the time when a fluorescence intensity is to be measured. For example, in the case of double staining shown in FIG. 13, in IFA fluorescence intensity measurement of sera of a patient with regards to CAML, the C-S protein, and the S-C protein, automatic measurement by use of an image analyzer is easily performed by measurement of a green light emission intensity at a portion stained red with a mouse anti-CAML antibody. Further, measurement of a red light emission intensity of the mouse anti-CAML antibody allows for correction of a protein expression level in each measurement.

Patient plasma diluted by a factor of 40 with PBS/2% BSA 0.05% Tween 20 was mixed with rabbit anti-CAMLG antibodies (Abcam) diluted by a factor of 1000. The mixture was then reacted for 1 hour at 37° C. with indirect fluorescent antibody method (IFA) antigens. The IFA antigens used in Example 4 were the same as those used in Example 1. Used as the secondary antibodies was a mixture of (i) Alexa Fluor 488 goat anti-human secondary antibodies (Molecular Probes) diluted by a factor of 200 with PBS/2% BSA 0.05% Tween 20 and (ii) Alexa Fluor 594 goat anti-rabbit secondary antibodies (Molecular Probes) diluted by a factor of 500 with PBS/2% BSA 0.05% Tween 20, which mixture was reacted for 30 minutes at 37° C.

Figure 13:
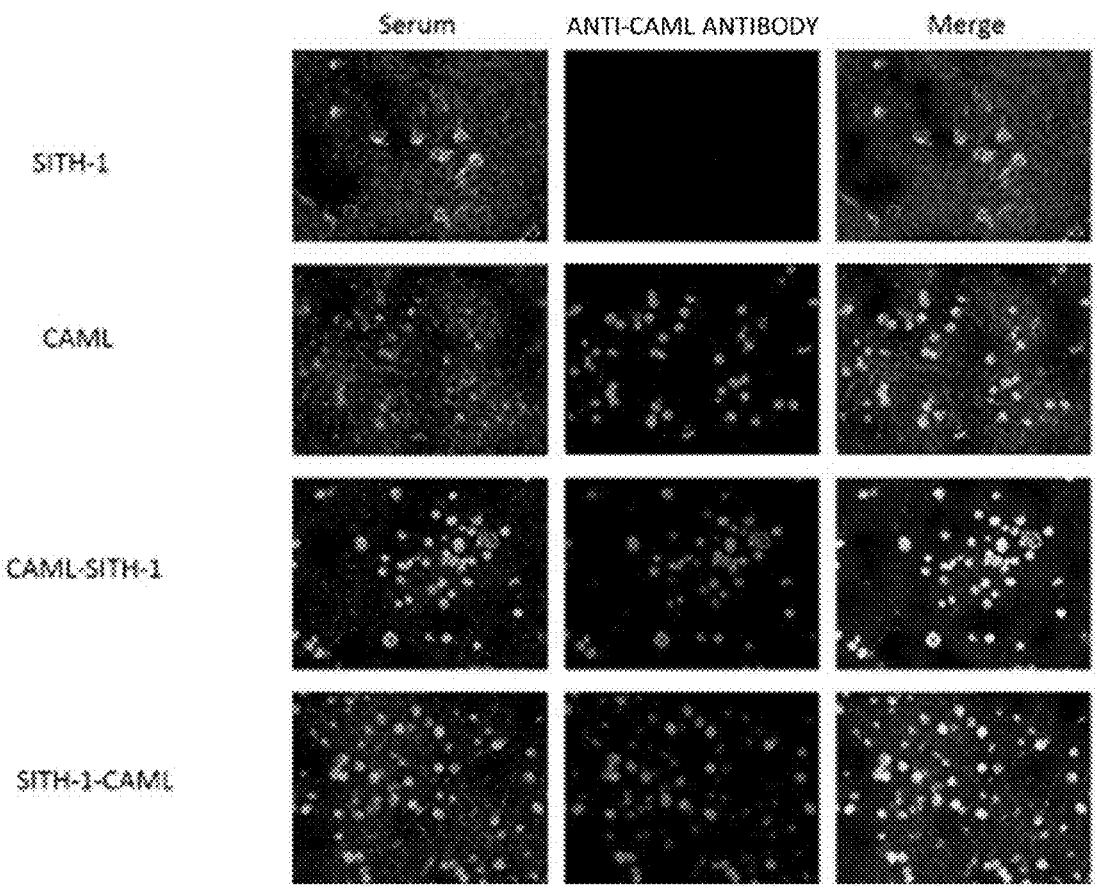
FIG. 13 illustrates reactions between (i) each type of protein and (ii) depression patient sera and an anti-CAML antibody with respect to, in accordance with Example 4 of the present invention.

FIG. 13 illustrates reactions between (i) each type of protein and (ii) depression patient sera and an anti-CAML antibody. Double staining was carried out with respect to each protein shown in FIG. 13, with the depression patient sera being stained green and the mouse anti-CAML antibody being stained red.

Example 5: Distinguishing Between (i) Depressive State which is Stage Prior to Onset of Mood Disorder and (ii) Temporarily Occurring Depressive State Caused by a Stressor Depressive states are known to include temporarily occurring depressive states caused by a stressor. Such stressors are also known as "life events", with examples including the death of an immediate family member, divorce, change of job, loss of job, change of residence, and loss of a pet.

In Example 5, it was studied whether or not it was possible, in a diagnosis method using a fusion protein, to distinguish between (i) a depressive state which is a stage prior to onset of a mood disorder and (ii) a temporarily occurring depressive state caused by a stressor.

The groups subjected to measurement were: Group B (13 persons who have a BDI score (11 or more) for which they would be diagnosed as being in a depressive state, excluding human subjects who were determined, from supplementary information, to be in a temporary depressive state due to a stressor); and Group D (human subjects who (i) have a BDI score (11 or more) for which they would be diagnosed as being in a depressive state, but (ii) were determined, from supplementary information, to be in a temporary depressive state due to a stressor.

Figure 14:
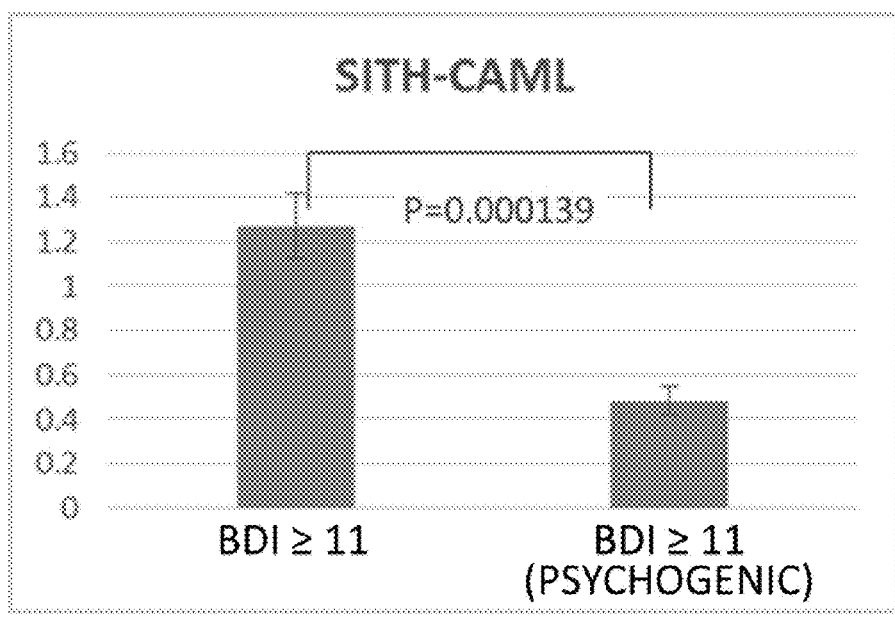
FIG. 14 shows IFA fluorescence intensities with respect to SITH-CAML in sera of subjects in depressive states having different causes, in accordance with Example 5 of the present invention.
Figure 15:
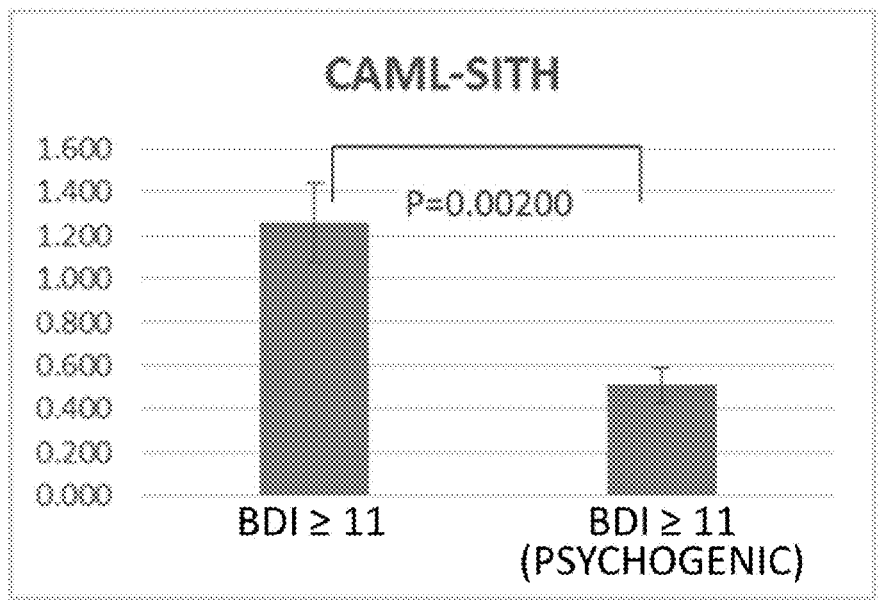
FIG. 15 shows IFA fluorescence intensities with respect to CAML-SITH in sera of subjects in depressive states having different causes, in accordance with Example 5 of the present invention.

Results are shown in FIGS. 14 and 15. For both the S-C protein and the C-S protein, there was a significant difference between Group B and Group D, with a very small P value.

This indicated that a depression test using the S-C protein or the C-S protein makes it possible to distinguish between (i) a depressive state which is a stage prior to onset of a mood disorder and (ii) a temporarily occurring depressive state caused by a stressor.

FIG. 14 shows IFA fluorescence intensities with respect to SITH-CAML in sera of subjects in depressive states having different causes. FIG. 14 shows ratios with respect to CAML. After confirming via a Shapiro-Wilk test that distribution was non-normal, a significant difference test was carried out via a t test (Welch's correction). Note that a temporarily occurring depressive state caused by a stressor is indicated here as "psychogenic".

FIG. 15 shows IFA fluorescence intensities with respect to CAML-SITH in sera of subjects in depressive states having different causes. FIG. 15 shows ratios with respect to CAML. After confirming via a Shapiro-Wilk test that distribution was non-normal, a significant difference test was carried out via a t test (Welch's correction). Note that a temporarily occurring depressive state caused by a stressor is indicated here as "psychogenic".

Example 6: Depression Diagnosis Via ELISA Using Fusion Protein

In Example 6, it was studied whether or not a depression diagnosis method using a fusion protein could be carried out via ELISA as well. SITH-1, the S-C protein, and the C-S protein were measured via ELISA in patients who tested weakly positive ("SITH-1 (±)"), positive ("SITH-1 (+)"), or strongly positive ("SITH-1 (2+)") for anti-SITH-1 antibody via IFA, as well as in healthy individuals who tested negative for anti-SITH-1 antibody via IFA.

Used as the expression plasmids for antigens were plasmids each obtained by inserting a respective one of SITH-1-His, SITH-CAML-His, and CAML-SITH-Hiswo (i.e., structures obtained by adding a His tag to the 3' end of SITH-1, SITH-CAML, and CAML-SITH as illustrated in FIG. 1) between a CMV promoter and a FLAG tag of pCMV-FLAG-5a. Each plasmid was transfected, by use of Lipofectamine LTX (Invitrogen), into HEK293T cells which had been cultured in 6 well plates. The transfected cells were then cultured for 48 hours and subsequently dissolved in a RIPA buffer (50 mmol/l Tris-HCl (pH 8.0), 150 mmol/l sodium chloride, 0.5 w/v % sodium deoxycholate, 0.1 w/v % sodium dodecyl sulfate, 1.0 w/v % NP-40).

HEK293T cells dissolved in a RIPA buffer were used as a control. For the fusion protein, the antigen liquid was directly fixed to a HisGrab (trademark) Nickel Coated S-well strip and washed with PBS(−) 0.1% Tween-20, and blocking was carried out with StartingBlock (trademark) Blocking Buffer with Tween-20. Human serum was diluted by a factor of 3,200 with StartingBlock (trademark) Blocking Buffer with Tween-20 and reacted with the fusion protein for 1 hour at 37° C., which was followed by washing with PBS(−) 0.1% Tween-20.

The secondary antibodies were prepared by adding, into 5 ml of PBS(−), (i) 50 μl of normal goat serum and (ii) 25 μl of biotinylated goat anti-human IgG, each included in a VECTASTAIN (registered trademark) Elite ABC Human IgG Kit. Reaction of the secondary antibodies was carried out for 30 minutes at 37° C., and washing with PBS(−) 0.1% Tween-20 was performed thereafter. Furthermore, the secondary antibodies were reacted with VECTASTAIN (registered trademark) ABC Reagent, included in the same kit, for 30 minutes at room temperature, and then conjugated with horseradish peroxidase (HRP). For detection of an ELISA reaction, after color reaction by use of 1-Step (trademark) Ultra TMB-ELISA, 2 M sulfuric acid was added, and measurements at 450 nm were carried out by use of an absorption spectrometer.

Figure 16:
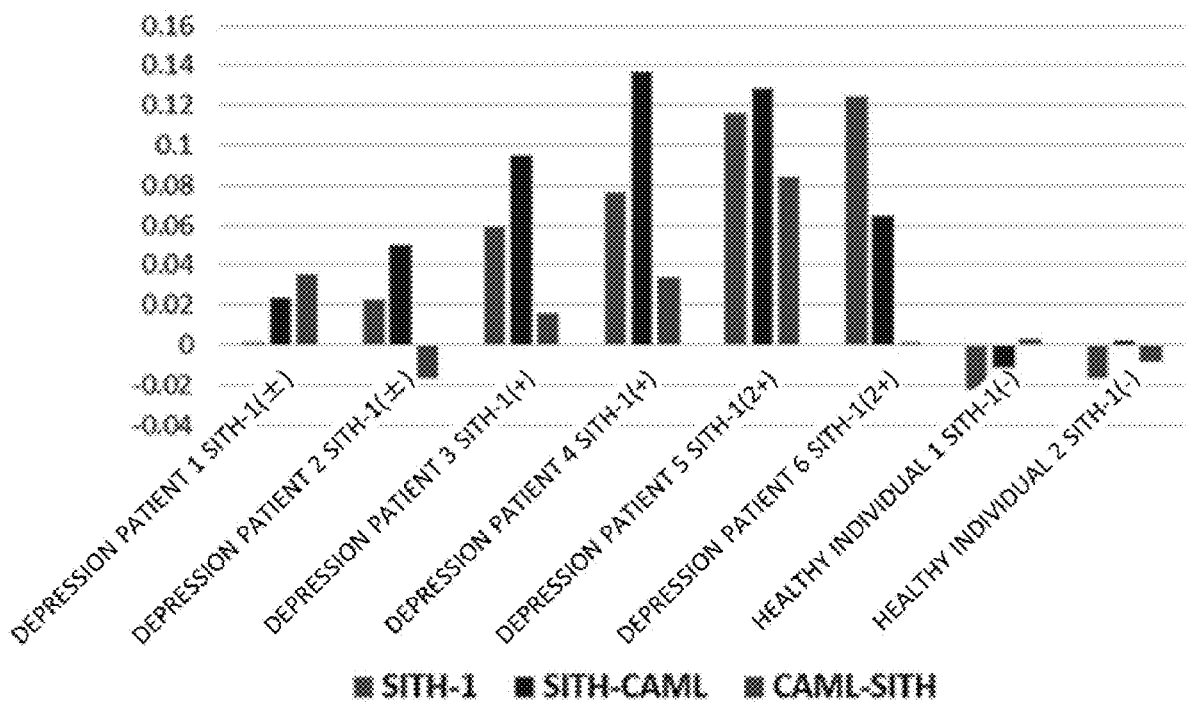
FIG. 16 shows results of ELISA using fusion proteins, in accordance with Example 6 of the present invention.

As a result, as illustrated in FIG. 16, it was found that with regards to the ELISA value for SITH-1, signal strength was enhanced by use of the S-C protein and the C-S protein, as was the case with IFA. Furthermore, the difference in signal strength among molecule types suggested that epitope transfer was associated with increased severity of a mood disorder.

FIG. 16 shows results of ELISA using fusion proteins.

Example 7

(1) Preparation of SITH-1-Expressing Adenovirus

A recombinant adenovirus was constructed as a virus that infects a model animal and expresses a SITH-1. The recombinant adenovirus was constructed in accordance with the standard protocol of an Adenovirus Expression Vector Kit (Takara bio).

A pGfa2Lac plasmid containing a glial fibrillary acidic protein (GFAP) promoter was provided by Dr. Kazuyoshi Ikuta (originally produced by Dr. Michael Brenner).

A GFAP promoter obtained from the pGfa2Lac plasmid and the SITH-1 gene amplified by PCR were cloned into an adenovirus cosmid vector by use of a standard method (Ad-GFAP-SITH-1). HEK293 cells were transfected with (i) the Ad-GFAP-SITH-1 cosmid vector or (ii) a cosmid vector (pAxcwit) which serves as a control and into which the target gene was not inserted.

The HEK293 cells were cultured in Dulbecco's modified Eagle's medium (DMEM) containing 10% fetal bovine serum. The recombinant adenovirus was prepared in 293 cells and purified with use of Adeno-X Virus Purification Kits (Clontech). The titer of the virus thus purified was determined by use of an Adeno-X rapid titer kits (Clontech).

(2) Mice to which SITH-1-Expressing Adenovirus was Nasally Administered

For the purpose of analyzing behaviors and gene expression level changes when SITH-1 is expressed in olfactory epithelium cells, the SITH-1-expressing adenovirus (SITH-1/Adv) was administered into nasal cavities of mice. Cosmid vector-derived adenovirus (empty/Adv) into which no SITH-1 gene was inserted was used as a control.

(2.1) Nasal Administration of SITH-1-Expressing Adenovirus 8-week-old C57BL/6NCrS1c mice were raised at a room temperature of 24±1° C. and with lights on for 12 hours and off for 12 hours. After each of the mice was anesthetized with use of isoflurane, SITH-1/Adv or empty/Adv in an amount equivalent to $2.5 \times 10^7$ ifu was dropped into the nasal cavity, and was then sucked by the mice along with breathing. Then, the mice were returned to raising cages.

(2.2) Tail Suspension Test of Mice to which SITH-1-Expressing Adenovirus was Nasally Administered 7 days after the nasal administration of SITH-1/Adv or empty/Adv, a tail suspension test was carried out for 10 minutes. A period of immobility time was measured with use of TailSuspScanTopScan (CleverSys, Inc.). The tail suspension test was carried out by suspending each mouse by taping the tail 1 cm from the end. The mouse was considered immobile if it was passive and did not move at all during suspension. In the experiment, 30 mice were used in each group.

Figure 17:
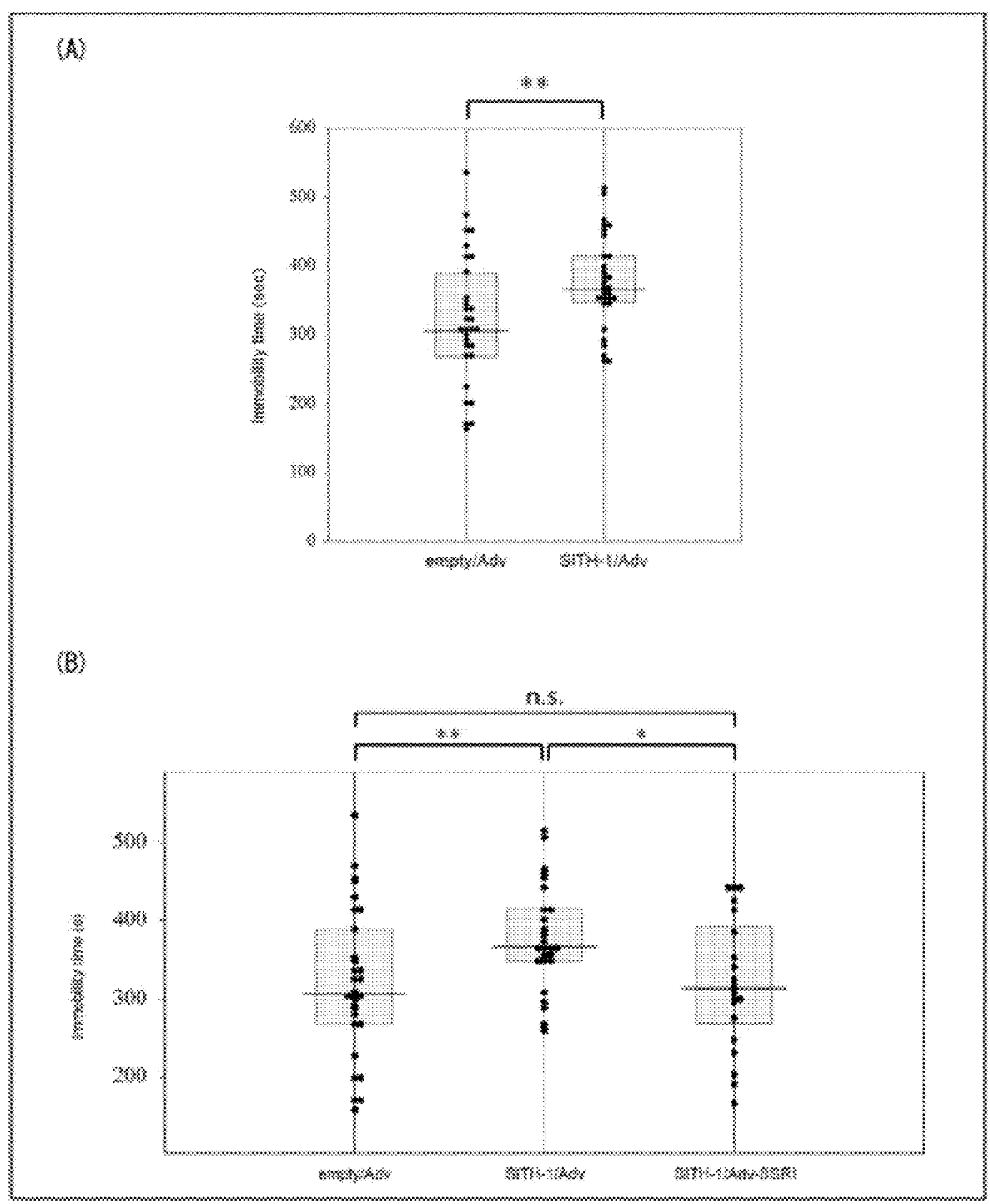
FIG. 17 shows the results of immobility time in a tail suspension test, in accordance with Example 7 of the present invention. (A) of FIG. 17 is a view showing the results of carrying out tail suspension tests of 30 empty/Adv nasal administration mice and 30 SITH-1/Adv nasal administration mice for 10 minutes, and then comparing respective periods of immobility time. (B) of FIG. 17 is a view showing the results of carrying out, for 10 minutes, a tail suspension test of 21 mice to which an SSRI had been administered since 2 weeks before nasal administration of SITH-1/Adv and then comparing periods of immobility time (SITH-1/Adv-SSRI).

FIG. 17 shows the results of immobility time in the tail suspension test.

(A) of FIG. 17 shows the results of comparison between (i) periods of immobility time of the mice into which empty/Adv was nasally administered (hereinafter referred to as "empty/Adv nasal administration mice") and (ii) periods of immobility time of the mice into which SITH-1/Adv was nasally administered (hereinafter referred to as "SITH-1/Adv nasal administration mice"). Statistical significance (* indicates P<0.05,  indicates P<0.01, and * indicates P<0.001) was calculated by use of the Mann-Whitney U-test.

(A) of FIG. 17 shows that the periods of immobility time of the SITH-1/Adv nasal administration mice were significantly increased in comparison with those of the empty/Adv nasal administration mice. This clearly demonstrated that the SITH-1/Adv nasal administration mice exhibited depression-like behaviors.

Then, it was studied whether or not an SSRI (selective serotonin reuptake inhibitor), which is an antidepressant, would suppress an increase in immobility time, the increase being caused by the nasal administration of the SITH-1/Adv. 80 mg/L of Fluoxetine solution as drinking water was given to 6-week-old mice, and then the mice were raised for 2 weeks. Then, SITH-1/Adv was nasally administered. 7 days after the nasal administration, a tail suspension test was carried out for 10 minutes. After the nasal administration of the SITH-1/Adv, the mice were raised in such a manner as to continue to receive 80 mg/L of Fluoxetine solution. In the experiment, 21 mice were used as an SSRI administered group. (B) of FIG. 17 shows the effect of the SSRI administration on the immobility time.

Statistical significance (* indicates P<0.05, indicates P<0.01, and *** indicates P<0.001) was calculated by use of the Mann-Whitney U-test.

(B) of FIG. 17 shows that immobility time increases observed among the SITH-1/Adv nasal administration mice were suppressed as a result of SSRI administration, and that a depression-like behavior caused by nasal administration of SITH-1/Adv can be therefore improved by administration of SSRI. Note that in view of the fact that Fluoxetine promotes Bcl-2 expression, the results above confirm that a mood disorder treatment agent which promotes Bcl-2 expression can be used as an agent for treating a mood disorder caused by SITH-1 expression.

(2.3) Analysis of Gene Expression of Mice to which SITH-1-Expressing Adenovirus was Nasally Administered For the purpose of studying whether or not nasal administration of SITH-1/Adv would cause a change in gene expression, olfactory bulbs and brains of the empty/Adv nasal administration mice and the SITH-1/Adv nasal administration mice were collected 24 hours after the tail suspension test. RNA of the olfactory bulbs and the brains were purified, and then amounts of mRNA of depression-related factors and apoptosis-related factors were quantified by use of real-time RT-PCR. A β-actin gene was used as a reference gene.

Figure 18:
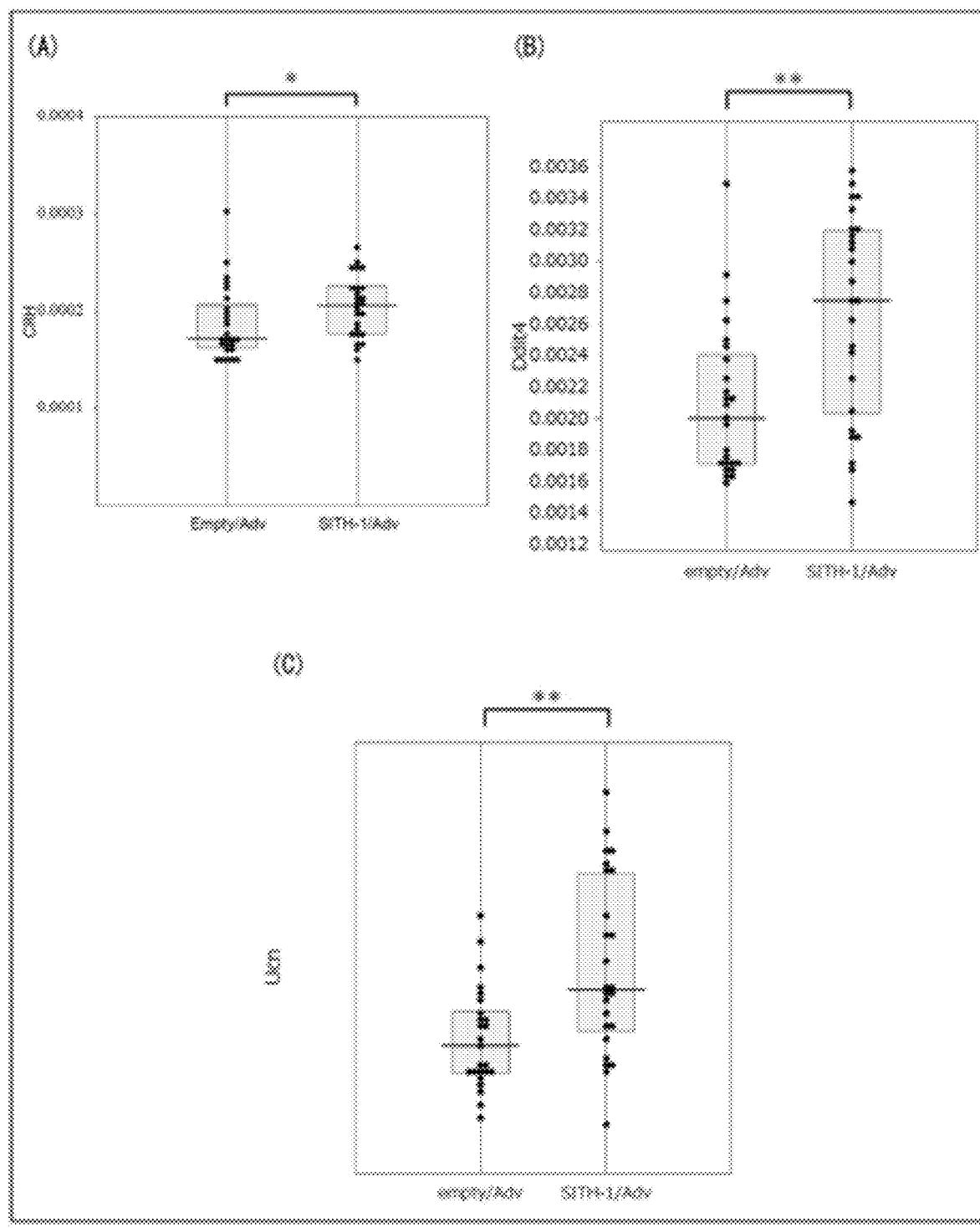
FIG. 18 shows the results of gene expression of depression-related factors in the brain, in accordance with Example 7 of the present invention. (A) of FIG. 18 is a view showing the results of CRH genes. (B) of FIG. 18 is a view showing the results of REDD1 genes. (C) of FIG. 18 is a view showing the results of Urocortin genes.
Figure 19:
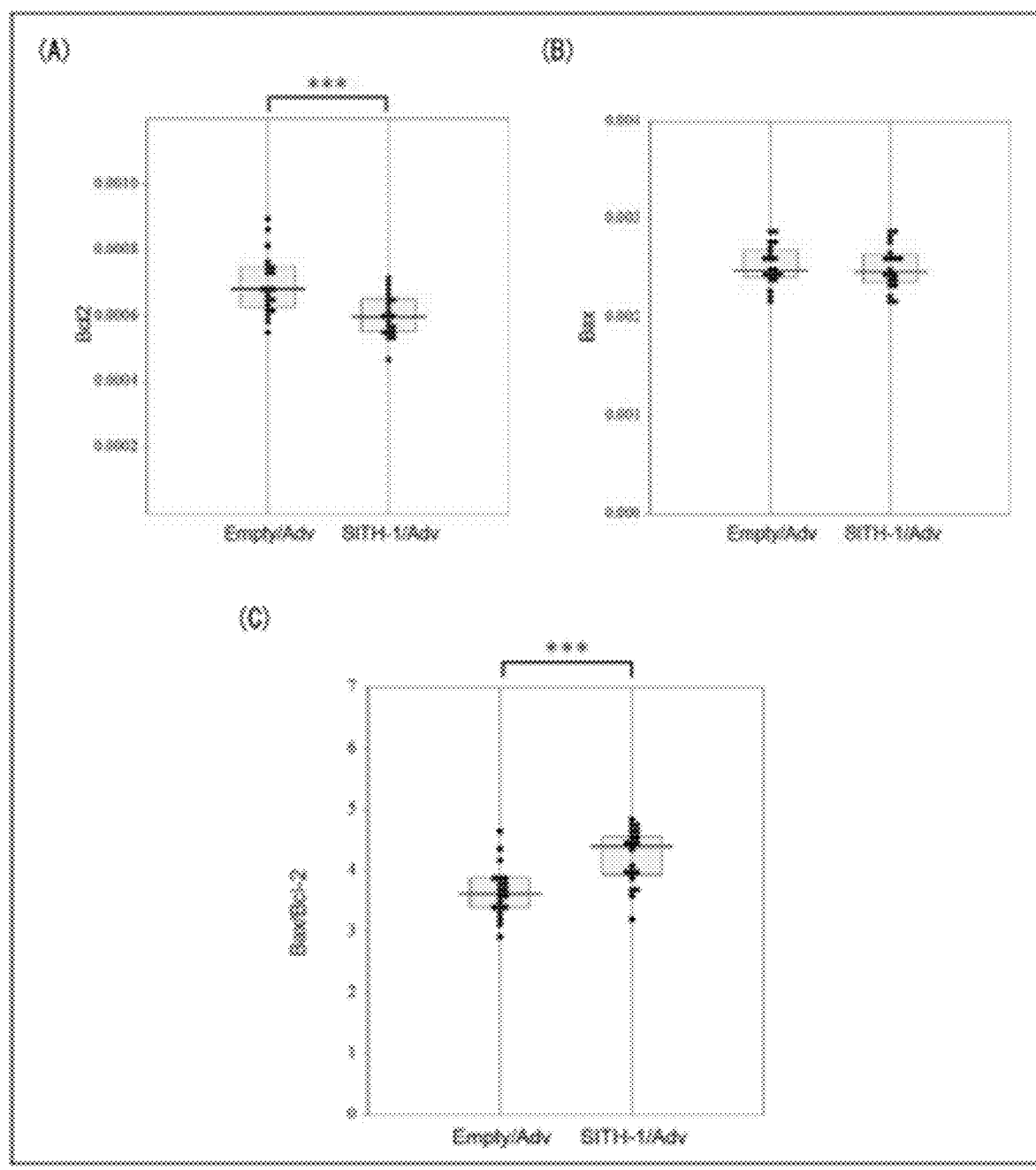
FIG. 19 shows the results of gene expression of apoptosis-related factors in olfactory bulbs, in accordance with Example 7 of the present invention. (A) of FIG. 19 is a view showing the results of gene expression of apoptosis inhibiting factors Bcl-2. (B) of FIG. 19 is a view showing the results of gene expression of apoptosis promoting factors Bax. (C) of FIG. 19 is a view showing apoptosis index Bax-to-Bcl-2 ratios.

FIG. 18 shows, as depression-related factors, expression levels of CRH, REDD1, and Urocortin genes of the whole brains excluding the olfactory bulbs. (A) of FIG. 18 is a view showing the results of CRH genes. (B) of FIG. 18 is a view showing the results of REDD1 genes. (C) of FIG. 18 is a view showing the results of Urocortin genes. Note that "Ddit4" in (B) of FIG. 18 is another name for REDD1. FIG. 19 shows (i) expression levels of Bcl-2 of olfactory bulbs, (ii) expression levels of Bax genes of the olfactory bulbs, and (iii) the ratio between the expression levels of the Bcl-2 and of the Bax gene (Bax/Bcl-2). Statistical significance (* indicates P<0.05,  indicates P<0.01, and * indicates P<0.001) was calculated by use of the Mann-Whitney U-test. (A) of FIG. 19 is a view showing the results of gene expression of apoptosis inhibiting factors Bcl-2. (B) of FIG. 19 is a view showing the results of gene expression of apoptosis promoting factors Bax. (C) of FIG. 19 is a view showing apoptosis index Bax-to-Bcl-2 ratios.

In regard to the depression-related factors, a comparison was made between (i) the expression levels of the genes of the whole brains (excluding the olfactory bulbs) of 25 empty/Adv nasal administration mice and (ii) the expression levels of the genes of the whole brains (excluding the olfactory bulbs) of 25 SITH-1/Adv nasal administration mice. Meanwhile, in regard to the apoptosis-related factors, a comparison was made between (i) the expression levels of apoptosis-related genes of the olfactory bulbs of 20 empty/Adv nasal administration mice and (ii) the expression levels of apoptosis-related genes of the olfactory bulbs of 20 SITH-1/Adv nasal administration mice.

FIG. 18 shows that the expression levels of CRH, REDD1, and Urocortin genes in the whole brains of the SITH-1/Adv nasal administration mice were significantly increased in comparison with those of the empty/Adv nasal administration mice. This clearly demonstrated that, as are the cases of depression patients, the SITH-1/Adv nasal administration mice exhibit increases in expression of CRH, REDD1, and Urocortin.

FIG. 19 also shows that the expression levels of Bcl-2, which is an apoptosis inhibiting factor, were significantly decreased in the olfactory bulbs of the SITH-1/Adv nasal administration mice in comparison with the empty/Adv nasal administration mice (see (A) of FIG. 19). Meanwhile, there was no significant difference in expression levels of Bax which is an apoptosis promoting factor (see (B) of FIG. 19). Calculation of a Bax-to-Bcl-2 ratio, which serves as an apoptosis index, indicated a significant increase in Bax-to-Bcl-2 ratios in the olfactory bulbs of the SITH-1/Adv nasal administration mice (see (C) of FIG. 19).

Therefore, it is considered that apoptosis is induced in the olfactory bulbs of the SITH-1/Adv nasal administration mice, and that this fact is associated with atrophy of olfactory bulbs of depression patients observed.

(2.4) Immunohistological Staining of Mice to which SITH-1-Expressing Adenovirus was Nasally Administered 24 hours after the tail suspension test, the empty/Adv nasal administration mice and the SITH-1/Adv nasal administration mice were each fixed in a 10% neutral buffered formalin solution, and then a paraffin section of a maxillary part of the cranial bone was prepared.

(2.4.1) TUNEL Staining of Paraffin Section of Maxillary Part of Cranial Bone of Mice TUNEL staining of paraffin section slides were carried out in accordance with the standard protocol of an In situ Apoptosis Detection Kit (TaKaRa Bio). For counter staining of nuclei, a mounting agent containing PI, VECTASHIELD Mounting Medium with PI (VECTOR Laboratories), was used. FIG. 20 shows the results of TUNEL staining of olfactory bulbs. (A) of FIG. 20 is a view showing TUNEL stained images of olfactory bulbs of empty/Adv nasal administration mice and SITH-1/Adv nasal administration mice, as observed with use of a fluorescence microscope. (B) of FIG. 20 is a view showing the results of counting the number of cells, in olfactory bulbs, which were positive for TUNEL staining. As shown in (A) of FIG. 20, genomes fragmented by apoptosis were stained green by TUNEL staining, and the nuclei of the cells were stained red by PI. In (B) of FIG. 20, statistical significance (* indicates P<0.05,  indicates P<0.01, and * indicates P<0.001) was calculated by use of the Mann-Whitney U-test. In comparison with the empty/Adv nasal administration mice, a large number of cells stained by TUNEL staining were observed in the olfactory bulbs of the SITH-1/Adv nasal administration mice. This is consistent with the results of the gene expression analysis, and therefore demonstrated that nasal administration of SITH-1/Adv induces apoptosis in an olfactory bulb.

(2.4.2) SITH-1 Expression in Olfactory Epithelium Cells of Mice

For the purpose of confirming SITH-1 protein expression in olfactory epithelium cells as a result of nasal administration of SITH-1/Adv, immunohistological staining of paraffin sections were carried out. After the paraffin section slides were deparaffinized, the paraffin section slides were immersed in a Tris-EDTA Buffer (100 mM Tris, 10 mM EDTA, 0.5% Tween 20, pH 9.0) at 98° C. for 20 minutes so that antigens were activated. Then, an Image-iT (trademark) FX Signal Enhancer (Life technologies) was dropped on each of the activated slides. Then, the slides were allowed to stand still at room temperature for 30 minutes so that blocking reactions were made.

A solution was obtained by 100-fold dilution of a rabbit anti-SITH-1 antibody and a mouse anti-GFAP antibody (Abcam) with use of a Can Get Signal immunostain Solution A (TOYOBO). Then, the solution was dropped on the slides. Then, the slides were allowed to stand still overnight at 4° C. After reactions, the glass slides were washed 3 times with use of a 0.2% Tween 20/PBS solution.

Solutions were obtained by 250-fold dilution and 400-fold dilution of Alexa Fluor 488 goat anti-rabbit IgG(H+L) (invitrogen) and of Alexa Fluor 594 goat anti-mice IgG(H+L) (invitrogen), respectively, with use of a Can Get Signal immunostain Solution A. Then, the solutions were dropped on the slides. Then, the slides were allowed to stand still at 37° C. for 1 hour.

After reactions, the glass slides were washed 3 times with use of a 0.2% Tween 20/PBS solution, and were then dried. Then, a cover glass was fixed with use of a mounting agent, ProLong Gold Antifade Reagent with DAPI (Life technologies). FIG. 21 shows the results of immunohistological staining of olfactory epithelia by the anti-SITH-1 antibody, as observed with a fluorescence microscope. FIG. 21 shows immunohistologically stained images of olfactory epithelium cells of empty/Adv nasal administration mice and SITH-1/Adv nasal administration mice.

In FIG. 21, the cells indicated by arrows are astrocytes in which SITH-1 protein expression was observed. In FIG. 21, cells stained by both the anti-SITH-1 antibody and the anti-GFAP antibody were observed only in olfactory epithelium cells of the SITH-1/Adv nasal administration mice. This confirmed that the nasal administration of SITH-1/Adv causes SITH-1 protein expression in the cells in the olfactory epithelium cells of the mice.

(2.5) Stress Vulnerability Test of Mice to which SITH-1-Expressing Adenovirus was Nasally Administered For the purpose of studying a possibility that nasal administration of SITH-1/Adv causes mice to be hypersensitive and more vulnerable to stress, stress vulnerability was studied.

8-week-old mice were each raised in isolation. Then, from 3 days before administration of SITH-1/Adv, the mice were given water and a 1% sucrose solution each as drinking water such that the two kinds of drinks were equilibrated in terms of ratio. 3 days later, SITH-1/Adv was nasally administered. Then, half of the mice were each raised in a cage that was slanted by 20 degrees. The amount of drinks consumed by the mice was recorded every 24 hours. FIG. 22 shows the results of a stress vulnerability test of SITH-1/Adv nasal administration mice.

FIG. 22 shows percentages of 1% sucrose solution drunk (amount of 1% sucrose solution drunk/amount of all drinks (amount of water drunk+amount of 1% sucrose solution drunk)) by the mice raised in isolated horizontal raising cages (normal: n=20) and by the mice raised in the isolated cages slanted by 20 degrees (slant: n=20) 7 days after the nasal administration of SITH-1/Adv. Statistical significance (* indicates P<0.05,  indicates P<0.01, and * indicates P<0.001) was calculated by use of the Mann-Whitney U-test.

FIG. 22 shows that applying a mild level of stress by slanting a cage caused the SITH-1/Adv nasal administration mice to have less preference for sucrose. It is therefore considered that the SITH-1/Adv nasal administration mice became hypersensitive to mild stress and therefore caused the SITH-1/Adv nasal administration mice to exhibit a "loss of pleasure" behavior which is observed among depression patients. This indicates that SITH-1 protein expression in the olfactory epithelium astrocytes induces stress vulnerability.

(3) Suppression of SITH-1 Expression by HHV-6 Infection Inhibitor

It was examined whether or not an HHV-6 infection inhibitor would suppress SITH-1 expression in HHV-6 host cells.

(3.1) Suppression of SITH-1 Expression by HHV-6 Neutralizing Antibody

An experiment was conducted by use of an HHV-6 neutralizing antibody serving as an HHV-6 infection inhibitor. As a neutralizing antibody, an anti-HHV-6B p98 (gH) monoclonal antibody was used. Since serum of a healthy individual also contains an anti-HHV-6 antibody, a 10-fold dilution series was prepared and used in the experiment.

Serum of healthy individuals was allowed to stand still at 56° C. for 30 minutes (inactivation). The following mixtures were prepared in equal amounts: (i) mixtures of HHV-6 HST strain virus fluid ($2.9 \times 10^6$ ffu/ml) and inactivated serum of healthy individuals (no dilution, 10-fold dilution in a medium (10% FBS-containing DMEM), and 100-fold dilution in a medium (10% FBS-containing DMEM)), (ii) mixtures of HHV-6 HST strain virus fluid ($2.9 \times 10^6$ ffu/ml) and anti-HHV-6B p98 (gH) monoclonal antibody (Clone: OHV-3) (10-fold dilution in a medium), and (iii) mixtures, serving as controls, of HHV-6 HST strain virus fluid ($2.9 \times 10^6$ ffu/ml) and a medium by itself. These mixtures were reacted at 37° C. for 1 hour.

Then, the virus fluid thus processed was used to infect, by centrifugation, U373 astrocytoma cells at a multiplicity of infection (MOI) (which is the number of viruses per cell) of 3. Then, the infected cells were cultured at 37° C. for 48 hours in a $CO_2$ incubator. From the resultant infected cells, RNA was purified by use of an RNeasy Mini Kit (Qiagen) in accordance with the standard protocol. Then, cDNA was synthesized by use of a PrimeScript RT Reagent Kit (Takara Bio).

Finally, expression levels of SITH-1 and GAPDH mRNA were measured by use of an Applied Biosystems 7300 Real-Time PCR system (Life Technologies). The measurement was carried out twice under the following conditions. Conditions of real-time PCR: 12.5 µl of Premix Ex Taq (Perfect Real Time) (Takara Bio Inc.); 0.225 µl of PCR forward primer (100 µM); 0.225 µl of PCR reverse primer (100 µM); 0.625 µl of TaqMan probe (10 µM); 0.5 µl of Rox reference dye; 2 µl of cDNA; and 8.925 µl of PCR-grade water. A total amount of 25 µl was thus used. The initial step was carried out at 95° C. for 30 seconds. Then the next step was carried out at 95° C. for 5 seconds and then at 60° C. for 31 seconds and was repeated for 45 cycles.

The sequences of the probe and the primer were as follows:

SITH-1 forward primer: SEQ ID NO: 8,
SITH-1 reverse primer: SEQ ID NO: 9,
SITH-1 probe: SEQ ID NO: 10 (FAM sequence and TAMRA sequences were added to the 5' end and 3' end, respectively),
GAPDH forward primer: SEQ ID NO: 11,
GAPDH reverse primer: SEQ ID NO: 12, and
GAPDH probe: SEQ ID NO: 13 (FAM sequence and TAMRA sequence were added to the 5' end and 3' end, respectively).

Note that the data was analyzed with use of a Sequence Detection Software version 1.4 (Applied Biosystems). FIG. 23 shows the results obtained. FIG. 23 shows the results of SITH-1 expression of HHV-6-infected U373.

The results show that a greater degree of dilution of serum of healthy individuals led to a greater level of SITH-1 expression (see A of FIG. 23). It is therefore considered that anti-HHV-6 antibodies contained in serum of the healthy individuals prevented infection with HHV-6, and that SITH-1 expression was therefore suppressed. In addition, SITH-1 expression in U373 cells were suppressed as a result of reacting HHV-6 with an HHV-6B p98 (gH) monoclonal antibody before infection with the HHV-6 (see B of FIG. 23).

These results demonstrated that an increase in anti-HHV-6 antibody causes SITH-1 expression to be suppressed.

(3.2) Suppression of SITH-1 Expression by Heparin and Anti-Heparan Sulfate Peptide An experiment was conducted by use of heparin and anti-heparan sulfate peptides serving as HHV-6 infection inhibitors.

U373 astrocytoma cells were removed with use of trypsin-EDTA, and then a medium (10% FBS-containing DMEM) was added, so that the resultant cells were at $1\times10^5$ cell/mL. Then, the U373 cells were reacted with 10 unit/mL of Novo-Heparin (Mochida Pharmaceutical Co., Ltd.) or 0.1 mM of anti-3-OS Heparan sulfate (HS) peptide trifluoroacetate salt (Sigma-Aldrich) at 4° C. for 1 hour. The U373 cells were also reacted only with a medium as a control at 4° C. for 1 hour. The resultant cells were washed 3 times with a medium. Then, the U373 cells thus washed were infected with a HHV-6 HST strain virus fluid ($2.9\times10^6$ ffu/ml) at a MOI of 3 by centrifugation. Then, the infected cells were cultured at 37° C. for 48 hours in a $CO_2$ incubator.

From the resultant infected cells, RNA was purified by use of an RNeasy Mini Kit (Qiagen) in accordance with the standard protocol. Then, cDNA was synthesized by use of a PrimeScript RT Reagent Kit (Takara Bio). Finally, expression levels of SITH-1 and GAPDH mRNA were measured by a method similar to that used in the above (3.1). FIG. 24 shows the results obtained. FIG. 24 shows the results of SITH-1 expression of HHV-6-infected U373.

In any of the case where heparin was used and the case where anti-heparan sulfate peptide was used, reacting the heparin or the anti-heparan sulfate peptide with the U373 cells before infection with HHV-6 caused SITH-1 expression in the U373 cells to be suppressed (see A and B of FIG. 24).

Example 8: SITH-1 Expression in Presence of Ganciclovir

In the presence of ganciclovir, human glial cell lines (U373) were infected with HHV-6, and SITH-1 expression levels in the infected cells was detected by use of Real-time PCR.

The U373 cells were cultured overnight in the presence of ganciclovir at concentrations indicated in the graph. Thereafter, the U373 cells were infected with HHV-6 variant B HST strain, and after one day had passed after this infection, the SITH-1 expression levels in the cells were detected by use of Real-time PCR.

With regards to an effective concentration of ganciclovir against HHV-6 variant B, IC50 was presumed to be approximately 10 µM. As such, three concentration levels obtained by 3-fold dilution were used, with 10 µM being a median amount.

For a primer and a TaqMan probe, the following sequences were used.

```
PCR primer forward:
                                  (SEQ ID NO: 14)
5'-CGTACCACTACTGATCTCGAAGC-3'

PCR primer reverse:
                                  (SEQ ID NO: 15)
5'-CTGTGGTCCAGGAACATGTAATG-3'

TaqMan probe:
                                  (SEQ ID NO: 16)
5'-CTTCTGTACATACCGATTCTGTGACGAGCC-3'
```

Results are shown in FIG. 25. FIG. 25 illustrates suppression of SITH-1 expression by ganciclovir. The vertical axis of FIG. 25 represents SITH-1 mRNA expression level as a ratio, where 1 is the ratio for ganciclovir(−). It was found that ganciclovir suppressed SITH-1 expression in glial cell lines (U373) infected with HHV-6. When ganciclovir was used in an amount of 3 µM, 10 µM, and 30 µM, SITH-1 mRNA expression levels were reduced by approximately 20%, 40%, and 80% or more, respectively.

Example 9: Effect of Fusion Protein on Intracellular Calcium Concentration

The inventors of the present invention discovered that when SITH-1 is expressed intracellularly, SITH-1 binds to CAML in the cell and thereby increases an intracellular calcium concentration (Patent Literature 2). Based on this knowledge, the inventors studied what sort of effect would be had on intracellular calcium concentration in a case where a fusion protein was expressed intracellularly.

In order to express SITH-1, the S-C protein, and the C-S protein intracellularly, pFLAG-CMV-5b (SIGMA-ALDRICH), which is an expression vector for mammals, was used to construct SITH-1/pFLAG-CMV-5b, SITH-CAML/pFLAG-CMV-5b, and CAML-SITH/pFLAG-CMV-5b. In each of the fusion proteins, the spacer (SEQ ID NO: 6) shown in FIG. 1 was inserted between SITH-1 and CAML. pFLAG-CMV-5b was used as a control. Each vector was transfected into HEK293 cells by use of a CalPhos (trademark) Mammalian Transfection Kit (Takara Bio), such that each protein was temporarily overexpressed intracellularly.

A Calcium Kit II-Fluo 4 (Dojindo) was used to cause cells to take up Fluo 4-AM, 24 hours after transfection. Thereafter, an ArrayScan XTI System (ThermoFisher Scientific) was used to measure fluorescence intensities ($\lambda ex=485$ nm, $\lambda em=518$) in cells expressing the various proteins (700 to 1300 cells per protein type).

FIG. 26 shows the results obtained. FIG. 26 indicates the effects of SITH-1 expression, S-C protein expression, and C-S protein expression on intracellular calcium concentration. Median, maximum, and minimum values are indicated as a box-and-whisker plot. Statistical significance (' indicates P<0.01) was determined via a multiple comparison test using Scheffe's method.

The results shown in FIG. 26 confirm that, in a SITH-1-expressing cell, the intracellular calcium concentration is increased in comparison to that in a control. This supports the findings to date. Furthermore, in a S-C protein-expressing cell, the intracellular calcium concentration is greatly increased in comparison to that in the SITH-1-expressing cell, whereas in a C-S protein-expressing cell, the intracellular calcium concentration is decreased in comparison to that in the control. These results suggested that when SITH-1 is expressed intracellularly and conjugated to CAML, the three-dimensional structure of a conjugate of the SITH-1 and the CAML is similar to the structure of the S-C protein.

Example 10: Relationship Between (i) Titer of Antibody Against S-C Protein and (ii) BDI Score in Healthy Subject For each of 83 human subjects determined to be healthy subjects from BDI results (BDI score of 10 or less), a titer of an antibody against the S-C protein in serum was measured by use of the indirect fluorescent antibody method. Thereafter, the correlation between the measured antibody titer and the BDI score was evaluated.

SITH-CAML and CAML were constructed as shown in FIG. 1 and then introduced into pFLAG-CMV-5a (SIGMA-ALDRICH), which is an expression vector for mammals, so as to obtain pCMV-SITH-CAML and pCMV-CAML, each of which is an expression plasmid for an antigen. Each plasmid was transfected, by use of Lipofectamine LTX (Invitrogen), into HEK293T cells that had been cultured on Lab-Tek chamber slides (Nunc). The transfected cells were then cultured for not less than 48 hours, fixed by drying, and subsequently fixed for 5 minutes with 3% methanol-added acetone that had been cooled. Antigens thus obtained were then used as IFA antigens.

Human subject serum was diluted by a factor of 80 with PBS/2% BSA 0.05% Tween 20 and stained by use of the indirect fluorescent antibody method (IFA). Used as secondary antibodies were Alexa Fluor 488 goat anti-human secondary antibodies (Molecular Probes) diluted by a factor of 200 with PBS/2% BSA 0.05% Tween 20.

The above were used to carry out the indirect fluorescent antibody method. Images were obtained by use of a fluorescence microscope having a CCD camera (DP73), and then ImageJ was used to quantify, from the images, fluorescence intensity of IFA stained cells. Based on the results of Example 3, the antibody titer of the anti-S-C antibody was corrected by dividing the IFA fluorescence intensity of the anti-S-C protein antibody by the IFA fluorescence intensity of the anti-CAML antibody.

FIG. 27 shows the results obtained. FIG. 27 illustrates a correlation between the antibody titer of the anti-S-C antibody in healthy subject serum and the BDI score. Spearman's rank correlation coefficient was used to determine the correlation between the antibody titer of the anti-S-C antibody and the BDI score. As a result, a strong positive correlation ($\rho=0.83$ $p=1.39\times10^{-22}$) was observed between the antibody titer and the BDI score. From these results, it was presumed that even in a human subject who is not in a depressive state and who is found to be a healthy subject, an increase in antibody titer of the anti-S-C antibody leads to an increased risk of developing a depressive state and to an increased risk of developing a mood disorder.

The following is a summary of the results of the above Examples.

(1) Diagnosis Method for Mood Disorder Including Step of Measuring Level of Anti-S-C Protein Antibody Levels of anti-S-C antibody were measured in respective sera obtained from the following three groups. Group A: a group of patients who were SITH-1 positive and who were diagnosed as having depression; Group B: a group of subjects who had a BDI score of 11 or greater and who were therefore diagnosed as being in a depressive state (excluding subjects who were determined, from supplementary information, to be in a temporary depressive state due to a stressor); and Group C: a group of healthy subjects having a BDI score of 10 or less. Significant differences were confirmed between Group A and Group B, between Group B and Group C, and between Group A and Group C. Group A had the highest antibody level, followed by Group B, and then Group C (see FIG. 7). It was therefore indicated that the present measurement method of measuring the level of the anti-S-C antibody makes it possible to distinguish between (i) a depressive state which does not satisfy diagnostic criteria for a mood disorder, i.e., a depressive state in which onset of a mood disorder has not occurred, and (ii) a mood disorder which has been developed or a healthy state.

Furthermore, on the basis of (i) a result of measurement of the antibody level, the presence or absence of a symptom of a mood disorder in each of Groups A, B, and C, and a degree of severity of the mood disorder, (ii) a fact that SITH-1 binds to CAML and thereby increases an intracellular calcium concentration, and (iii) the above-described mechanism of pathogenesis of a mood disorder, it is thought that: a larger number of times of SITH-1 expression in olfactory epithelium cells results in (a) an increased risk of developing a mood disorder and (b) an increased degree of severity of a mood disorder and (c) accordingly an increased level of the anti-S-C antibody. It is therefore assumed that Group B is at a high risk of a mood disorder.

Furthermore, in the group of healthy subjects, there was a strong positive correlation between (i) the level of the anti-S-C antibody and (ii) the BDI score (see FIG. 27). From this fact, it is assumed that even in a subject that does not show a depressive state, an increase in the anti-S-C antibody correlates to an increase in risk of developing a depressive state and in risk of developing a mood disorder. This assumption is consistent with the above-described mechanism.

Thus, it was found that measuring the level of anti-S-C antibody in serum makes it possible not only to determine whether or not a human subject has a mood disorder, but also to assess a human subject's risk (degree of risk) of developing a mood disorder or a depressive state.

Furthermore, in a comparison of the levels of the anti-S-C antibody in sera from Group B and Group D (human subjects, excluded from Group B, who had a BDI score of 11 or more but were determined, from supplementary information, to be in a temporary depressive state due to a stressor), the inventors of the present invention observed a significant difference between the two groups (see FIG. 14).

(2) Diagnosis method for mood disorder including step of measuring level of anti-C-S protein antibody Upon measurement of levels of the anti-C-S antibody in respective sera obtained from the above Groups A, B, and C, no significant difference was found between Group A and Group B, but significant differences were confirmed between Group A and Group C, and between Group B and Group C. Group A had the highest antibody level, followed by Group B, and then Group C (see FIG. 8). It was therefore indicated that the present measurement method of measuring the level of the anti-C-S antibody makes it possible to distinguish between (i) a healthy state and (ii) a mood disorder which has been developed or a depressive state in which onset of a mood disorder has not occurred.

Furthermore, on the basis of (i) a result of measurement of the antibody level, the presence or absence of a symptom of a mood disorder in each of Groups A, B, and C, and a degree of severity of the mood disorder, (ii) a fact that SITH-1 binds to CAML and thereby increases an intracellular calcium concentration, and (iii) the above-described mechanism of pathogenesis of a mood disorder, it is thought that: a larger number of times of SITH-1 expression in olfactory epithelium cells results in (a) an increased risk of developing a mood disorder and (b) an increased degree of severity of a mood disorder and (c) accordingly an increased level of the anti-C-S antibody. It is therefore assumed that Group B is at a high risk of a mood disorder.

Thus, it was found that measuring the level of the anti-C-S antibody in serum makes it possible to assess a human subject's risk (degree of risk) of developing a target disorder.

Furthermore, in a comparison of levels of the anti-C-S antibody in respective sera from Group B and Group D, the inventors of the present invention observed a significant difference between the two groups (see FIG. 15).

(3) Diagnosis Method for Mood Disorder Including Step of Measuring Level of Anti-CAML Antibody Upon examining whether an anti-CAML antibody was present in sera obtained from the above Groups A, B, and C, the inventors of the present invention surprisingly discovered that the anti-CAML antibody was present in all subjects. Because CAML is a human protein, the anti-CAML antibody is considered to be an autoantibody resulting from an autoimmune reaction. There had been no prior reports on the anti-CAML antibody as an autoantibody. Furthermore, with regards to levels of the anti-CAML antibody, Group A had the lowest level, Group B had the second lowest level, and Group C had the highest level. The antibody level of Group A was significantly lower than that of Group C (see FIG. 9). Based on these results, the value for the antibody level of each specimen, determined through the mood disorder diagnosis method using the above fusion protein, was corrected by dividing the value by the level of the anti-CAML antibody in that specimen. The use of such correction resulted in a greatly reduced P value in a significant difference test, in comparison to cases where correction was not performed (see FIGS. 7 and 11, and FIGS. 8 and 12). Thus, it was discovered that using results of anti-CAML antibody measurement in combination with the above diagnosis method for a mood disorder increases the accuracy of diagnosis.

Further, the "method for diagnosing whether or not a human subject has a mood disorder, by measuring an anti-SITH-1 antibody in a biological sample isolated from the human subject" (Patent Literature 2, hereinafter, referred to as "conventional method"), which method has been developed by the inventors of the present invention, was carried out with respect to Groups A, B, and C. In the case of the above method as well, it was found that using the results of anti-CAML antibody measurement in the same manner as above greatly increases the accuracy of diagnosis (see FIGS. 6 and 10).

Therefore, in an aspect of the present invention, there is provided a diagnosis method for a mood disorder which diagnosis method includes measuring a level of an anti-SITH-1 antibody in a biological sample isolated from a human subject, the diagnosis method including the step of measuring a level of an anti-CAML antibody in the biological sample isolated from the human subject. Note that a method of obtaining data for making a diagnosis in accordance with an embodiment of the present invention is also an aspect of the present invention. That is, an embodiment of the present invention encompasses a method of obtaining data for making a diagnosis, which method includes each step of the above-mentioned diagnosis method.

The mechanism has been clarified as below from the result of the above studies, but the mechanism is not limited to the following. That is, the following is considered to be the mechanism. Originally, an autoimmune reaction to CAML occurs in humans. When infection of olfactory epithelium with HHV-6 causes expression of SITH-1 and then CAML binds to this SITH-1, immunity to CAML shifts to immunity to a conjugate of CAML and SITH-1. Subsequently, as a result of frequent infection with HHV-6, a major epitope transfers from an anti-C-S antibody recognition site to an anti-S-C antibody recognition site. This mechanism is also supported by the fact that a level of an anti-CAML antibody in an anti-SITH-1 antibody-positive patient suffering from depression is significantly lower than that of a healthy subject (see FIG. 9). Further, enhancement of an immune reaction by autoimmunity to CAML can provide an explanation about a reason why SITH-1 is detected with a high sensitivity as a serum antibody though SITH-1 is produced only a little in an astrocyte present in a brain, olfactory epithelium, and the like. Note that the phenomenon of such epitope transfer is also reported in Dirk. et al., J. Exp. Med, Volume 189, Number 4, Feb. 15, 1999 701-709.

(4) Detection Sensitivity of Diagnosis Method of an Embodiment of the Present Invention The inventors of the present invention studied detection sensitivity of the diagnosis method of an embodiment of the present invention. For the above Group A, the inventors carried out microscopic observation, via IFA, with regards to SITH-1, the S-C protein, and the C-S protein as antigens. It was found that the images of the S-C protein were much more brightly stained than the images of SITH-1 (see FIG. 2). Image analysis software was then used to measure fluorescence intensity for each protein. The S-C protein images had the highest fluorescence intensity, followed by a C-S protein image, and then a SITH-1 image. A significant difference was observed between the S-C protein and SITH-1. These findings indicated that in a mood disorder patient, the use of the S-C protein as an antigen significantly enhances antibody signals (see FIG. 3).

The inventors also confirmed these results in an experimental system in which a fusion protein was isolated. Specifically, antibody signals for the S-C protein and SITH-1 were compared via ELISA, and it was found that, in a depression patient, the signal of an antibody against the S-C protein was stronger than that of an antibody against SITH-1 (see FIG. 16).

INDUSTRIAL APPLICABILITY

A method for diagnosing, treating, or preventing a mood disorder in accordance with an embodiment of the present invention can be used in clinical medicine and also in various fields.

SEQUENCE LISTING

JT15288 Sequence listing

The invention claimed is:

1. A diagnosis and/or examination method for a mood disorder in a human subject, comprising the steps of:
 a) obtaining a biological sample from a human subject;
 b) measuring a level of an antibody recognizing a protein composed of an amino acid sequence shown in SEQ ID NO: 17 in a biological sample isolated from the human subject;
 c) measuring a level of an antibody recognizing a protein composed of an amino acid sequence shown in SEQ ID NO: 4 in the biological sample isolated from the human subject;
 d) correcting the level of the antibody measured in step b) by the level of the antibody measured in step c) to obtain a corrected antibody level; and
 e) if the corrected antibody level obtained in step d) is higher than a set threshold,
 diagnosing and/or examining the human subject as follows: (i) a mood disorder is developed in the human subject; (ii) the human subject has a risk of developing a mood disorder; (iii) a depressive state of the human subject is not a temporary depressive state caused by a non-viral stressor; (iv) the human subject has a predisposing factor for developing a mood disorder; and/or (v) an effect of treatment of a mood disorder on the human subject is not sufficient; wherein
 the level of at least one of said antibodies is measured by using a fusion protein, a labeled protein, or a protein on a support.

2. The diagnosis and/or examination method as set forth in claim 1, wherein
 step b) comprises measuring the level of the antibody recognizing the protein composed of the amino acid sequence shown in SEQ ID NO: 17 with use of a fusion protein,
 the fusion protein being comprised of a first protein having a sequence identity of 98% or higher with an amino acid sequence shown in SEQ ID NO: 1 and a second protein having a sequence identity of 98% or higher with the amino acid sequence shown in SEQ ID NO: 4, a C terminal of the first protein and an N terminal of the second protein being bound to each other via a linker.

3. A diagnosis and/or examination method for a mood disorder in a human subject, comprising: the steps of:
 a) obtaining a biological sample from a human subject;
 b) measuring a level of an antibody recognizing a protein composed of an amino acid sequence shown in SEQ ID NO: 18 in a biological sample isolated from the human subject;
 c) measuring a level of an antibody recognizing a protein composed of an amino acid sequence shown in SEQ ID NO: 4 in the biological sample isolated from the human subject;
 d) correcting the level of the antibody measured in step b) by the level of the antibody measured in step c) to obtain a corrected antibody level; and
 e) if the corrected antibody level obtained in step d) is higher than a set threshold, diagnosing and/or examining that the human subject is as follows: (i) a mood disorder is developed in the human subject; (ii) the human subject has a risk of developing a mood disorder; (iii) a depressive state of the human subject is not a temporary depressive state caused by a non-viral stressor; (iv) the human subject has a predisposing factor for developing a mood disorder; and/or (v) an effect of treatment of a mood disorder on the human subject is not sufficient; wherein
 the level of at least one of said antibodies is measured by using a fusion protein, a labeled protein, or a protein on a support.

4. The diagnosis and/or examination method as set forth in claim 3, wherein
 step b) comprises measuring the level of the antibody recognizing the protein composed of the amino acid sequence shown in SEQ ID NO: 18 with use of a fusion protein, the fusion protein being comprised of a first protein having a sequence identity of 98% or higher with an amino acid sequence shown in SEQ ID NO: 1 and a second protein having a sequence identity of 98% or higher with the amino acid sequence shown in SEQ ID NO: 4, an N terminal of the first protein and a C terminal of the second protein being bound to each other via a linker.

5. A diagnosis kit for diagnosis of a mood disorder in a human subject, comprising:
  a support on which one or both of the following fusion proteins (i) and (ii) is/are immobilized
    (i) a fusion protein comprised of a first protein having a sequence identity of 98% or higher with an amino acid sequence shown in SEQ ID NO: 1 and a second protein having a sequence identity of 98% or higher with an amino acid sequence shown in SEQ ID NO: 4, a C-terminus of the first protein and an N-terminus of the second protein being bound to each other via a linker, and
    (ii) a fusion protein comprised of a third protein having a sequence identity of 98% or higher with the amino acid sequence shown in SEQ ID NO: 1 and a fourth protein having a sequence identity of 98% or higher with the amino acid sequence shown in SEQ ID NO: 4, an N-terminus of the third protein and a C-terminus of the fourth protein being bound to each other via a linker; and
  a support on which a protein having a sequence identity of 98% or higher with the amino acid sequence shown in SEQ ID NO: 4 is immobilized.

6. A method of detecting anti-SITH-1 and anti-CAML antibodies in a human subject suspected of having a mood disorder, comprising the steps of:
  a) obtaining a biological sample from said human subject:
  b) measuring the level of antibodies recognizing a protein comprising SEQ ID NO: 1 in the biological sample isolated from said human subject; and
  c) measuring the level of antibodies recognizing a protein comprising SEQ ID NO: 4 in the biological sample isolated from said human subject
  d) correcting the level of the antibody measured in step b) by the level of the antibody measured in step c) to obtain a corrected antibody level:
  e) determining if the corrected antibody level obtained in step d) is higher than a set threshold: and
  f) diagnosing said subject with a mood disorder if the corrected antibody level obtained in step d) is higher than the set threshold; and
  g) administering a treatment for said mood disorder in said subject if the corrected antibody level is higher than the set threshold.

7. The method of claim 6, wherein the treatment comprises tricyclic antidepressants, selective serotonin reuptake inhibitor (SSRI), and/or serotonin and norepinephrine reuptake inhibitors (SNRI).

8. A method of treatment of a mood disorder in a human subject, comprising the steps of:
  a) obtaining a biological sample from said human subject;
  b) measuring the level of antibodies recognizing a protein comprising an amino acid sequence shown in SEQ ID NO: 1 in the biological sample isolated from said human subject;
  c) measuring the level of antibodies recognizing a protein comprising an amino acid sequence shown in SEQ ID NO: 4 in the biological sample isolated from said human subject:
  d) correcting the level of the antibody measured in step b) by the level of the antibody measured in step c) to obtain a corrected antibody level:
  e) determining if the corrected antibody level obtained in step d) is higher than a set threshold: and
  f) diagnosing said subject with a mood disorder if the corrected antibody level obtained in step d) is higher than the set threshold; and
  g) administering a treatment for said mood disorder to said subject if the corrected antibody level is higher than the set threshold.

9. The method of claim 8, wherein the treatment comprises tricyclic antidepressants, selective serotonin reuptake inhibitor (SSRI), and/or serotonin and norepinephrine reuptake inhibitors (SNRI).

10. A method of diagnosis of a mood disorder in a human subject, comprising the steps of:
  diagnosing that the human subject is in at least one of the following states (i) to (iv) if a corrected antibody level is higher than a set threshold, wherein the corrected antibody level is obtained by:
  a) obtaining a biological sample from said human subject;
  b) measuring the level of antibodies recognizing a protein comprising SEQ ID NO: 4 in the biological sample isolated from said human subject;
  c) measuring the level of antibodies recognizing a protein comprising SEQ ID NO: 17 or 18 in the biological sample isolated from said human subject;
  d) correcting the level of the antibody measured in step b) by the level of the antibody measured in step c) to obtain a corrected antibody level:
  e) determining if the corrected antibody level obtained in step d) is higher than a set threshold: and
  f) diagnosing said subject with a mood disorder if the corrected antibody level obtained in step d) is higher than the set threshold;
  wherein the potential states are:
  (i) the human subject has developed a mood disorder;
  (ii) the human subject is at risk of or has a pre-disposing factor for developing a mood disorder;
  (iii) the human subject is in a depressive state that is not temporary and/or is not caused by a non-viral stressor;
  (iv) an effect of treatment of a mood disorder on the human subject is not sufficient.

* * * * *

```
                         SEQUENCE LISTING

<160> NUMBER OF SEQ ID NOS: 22

<210> SEQ ID NO 1
<211> LENGTH: 159
<212> TYPE: PRT
<213> ORGANISM: Human herpesvirus 6

<400> SEQUENCE: 1

Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ala Ile Thr Met
            20                  25                  30

Leu Thr Leu Glu Ile Ile Ser Asn Gln Lys Arg Thr Thr Thr Asp Leu
        35                  40                  45

Glu Ala Val Thr Val Ala Leu Lys His Val Ser Thr Ser Leu Ala Ser
    50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
            100                 105                 110

Cys Ile Met Met Ile Phe Ile Thr Cys Ser Trp Thr Thr Glu Lys Asp
        115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val
145                 150                 155

<210> SEQ ID NO 2
<211> LENGTH: 480
<212> TYPE: DNA
<213> ORGANISM: Human herpesvirus 6

<400> SEQUENCE: 2
atgggatatg aagaaaaagt gtcagctact ggaaagactc gtttaaagat actggcatgt      60
ctgatcgttt taatactagc tgcggcaata actatgttaa cgctggaaat tatatcgaac     120
caaaaacgta ccactactga tctcgaagct gtgactgtgg cgctgaagca tgtaagcaca     180
tctcttgcca gctgcactga atccactact tctgtacata ccgattctgt gacgagccaa     240
cccacgaaaa acaagaatc gaggaaaaaa attgaaggga atctccaag ttgggttcag       300 gctttaacta cagcatctgg aattatccta ctgttttgta taatgatgat attcattaca     360
tgttcctgga ccacagaaaa agatacagag aagagtgaag tgcaatctta tgcttcttca     420
gtagagactt tagactcttt aaatgaggct attataccga aaactgaaat gaatgtgtaa     480

<210> SEQ ID NO 3
<211> LENGTH: 1795
<212> TYPE: DNA
<213> ORGANISM: Human herpesvirus 6

<400> SEQUENCE: 3
aggctctgct ggaggctctg ctggaggcct tgctgaaggc tctgctggag gccctgctgg      60
```

```
aggtcttgct ggaggctctg ctggaggctc tgctggaggc tctgctggag gctctgctgg      120
aggctctgct ggaggctctg ctggaggctc tgtcagagac ctcggtgaaa gttttactca      180
gaggtttatc agagttttcg ccattagttt ggttagaagt ttcagattta ttttcggtgg      240
aactgcagtt aggtttcatg tcagtacatt catcaccgtt agaagtgcta ttcatggtgc      300
tgttgccact gttggatttg ttaaaagcag taaatgagct aggattggaa tgactccgaa      360
tagctaataa atttgagcat tttcttcgaa tggatcataa tcagagggat agccatctaa      420
tttaaagact tccattttat cactgttgca atcacttcta atggagtatc tggatacatt      480
ttttctacat cttttcatc ccctccaaca tggatctgtg cagcgttaat aagccagcgg      540
agttaattaa atcgtcttcc atgttagaca gttcctgttt catggcagcc ttcactgatg      600
caccaatact ttggatgcaa gtgccaacgg actgagctag gatgtaaaag aagatattct      660
aattttgaat tcttcagatg ctccttcttc cacattactg aataggaca cattcttgga      720 agcgatgtcg ttggaagact ctgggatgaa aagatcacag gcttccagtt ctggaaaaag      780
caggctttca aggacacat cacacttgag actctcttcc aatatttctt tgatggattc      840
ttccaccact ggatcgggat ggtagctata tatactatat aaggagatta ccaccaccac      900
ctctttcttt gcagagatta ttctctgctt gaaaatctgt aacactgatc atgatgggat      960
atgaagaaaa agtgtcagct actggaaaga ctcgtttaaa gatactggca tgtctgatcg     1020
ttttaatact agctgcggca ataactatgt taacgctgga attatatcg aaccaaaaac     1080 gtaccactac tgatctcgaa gctgtgactg tggcgctgaa gcatgtaagc acatctcttg     1140
ccagctgcac tgaatccact acttctgtac ataccgattc tgtgacgagc caacccacga     1200
aaaacaaaga atcgaggaaa aaaattgaag ggaaatctcc aagttgggtt caggctttaa     1260
ctacagcatc tggaattatc ctactgtttt gtataatgat gatattcatt acatgtccct     1320
ggaccacaga aaaagataca gagaagagtg aagtgcaatc ttatgctcct tcagtagaga     1380
ctttagaccc tttaaatgag gctattatac cgaaaactga atgaatgtg taatgtctgt     1440 atttttcttt acagagatgt acggagagtt tatatttggg gaaaatacct gactgttctg     1500
cctatatgcg aatgttaaag tatgtataat ataaattctt acctttaag agtgattcaa     1560 ggtggaggtt tctttggaga ttgattccag gtggtggttt cgggtgcaat caatctttct     1620
tctgggcggg aagaaaatcc agcaatccaa taattgatgg gatgtaatca atgtcacaaa     1680
tctgtaagat taaatgtgaa cagtataaat tctttcgtgc ttatcaaatt acaattatgc     1740
gcatgaaaat atcattaaat tgttttaaac attcttaaaa aaaaaaaaaa aaaaa           1795
```

<210> SEQ ID NO 4
<211> LENGTH: 296
<212> TYPE: PRT
<213> ORGANISM: Homo sapiens

<400> SEQUENCE: 4

Met Glu Ser Met Ala Val Ala Thr Asp Gly Gly Glu Arg Pro Gly Val
1               5                   10                  15

Pro Ala Gly Ser Gly Leu Ser Ala Ser Gln Arg Arg Ala Glu Leu Arg
                20                  25                  30

Arg Arg Lys Leu Leu Met Asn Ser Glu Gln Arg Ile Asn Arg Ile Met
            35                  40                  45

Gly Phe His Arg Pro Gly Ser Gly Ala Glu Glu Glu Ser Gln Thr Lys
        50                  55                  60

Ser Lys Gln Gln Asp Ser Asp Lys Leu Asn Ser Leu Ser Val Pro Ser

```
                65                  70                  75                  80
Val Ser Lys Arg Val Leu Gly Asp Ser Val Ser Thr Gly Thr Thr
                    85                  90                  95

Asp Gln Gln Gly Gly Val Ala Glu Val Lys Gly Thr Gln Leu Gly Asp
                100                 105                 110

Lys Leu Asp Ser Phe Ile Lys Pro Pro Glu Cys Ser Ser Asp Val Asn
            115                 120                 125

Leu Glu Leu Arg Gln Arg Asn Arg Gly Asp Leu Thr Ala Asp Ser Val
    130                 135                 140

Gln Arg Gly Ser Arg His Gly Leu Glu Gln Tyr Leu Ser Arg Phe Glu
145                 150                 155                 160

Glu Ala Met Lys Leu Arg Lys Gln Leu Ile Ser Glu Lys Pro Ser Gln
                165                 170                 175

Glu Asp Gly Asn Thr Thr Glu Glu Phe Asp Ser Phe Arg Ile Phe Arg
            180                 185                 190

Leu Val Gly Cys Ala Leu Leu Ala Leu Gly Val Arg Ala Phe Val Cys
        195                 200                 205

Lys Tyr Leu Ser Ile Phe Ala Pro Phe Leu Thr Leu Gln Leu Ala Tyr
    210                 215                 220

Met Gly Leu Tyr Lys Tyr Phe Pro Lys Ser Glu Lys Lys Ile Lys Thr
225                 230                 235                 240

Thr Val Leu Thr Ala Ala Leu Leu Leu Ser Gly Ile Pro Ala Glu Val
                245                 250                 255

Ile Asn Arg Ser Met Asp Thr Tyr Ser Lys Met Gly Glu Val Phe Thr
            260                 265                 270

Asp Leu Cys Val Tyr Phe Phe Thr Phe Ile Phe Cys His Glu Leu Leu
        275                 280                 285

Asp Tyr Trp Gly Ser Glu Val Pro
    290                 295

<210> SEQ ID NO 5
<211> LENGTH: 1350
<212> TYPE: DNA
<213> ORGANISM: Homo sapiens

<400> SEQUENCE: 5
cgccactgcc accoctccca gactgtggac gggaggatgg agtcgatggc cgtcgctacc        60
gacggcgggg agaggccggg ggtcccagcg ggctcaggtc tgtcggcttc ccagcgtcgg       120
gcggagctgc gtcggagaaa gctgctcatg aactcggaac agcgcatcaa ccggatcatg       180
ggctttcaca ggcccgggag cggcgcggaa gaagaaagtc aaacaaaatc aaagcagcag       240
gacagtgata aactgaactc cctcagcgtt ccttccgttt caaagcgagt agtgctgggt       300
gattcagtca gtacaggaac aactgaccag cagggtggtg tggccgaggt aaaggggacc       360
caactgggag acaaattgga ctcgttcatt aaaccacctg agtgcagtag tgatgtcaac       420
cttgagctcc ggcagcggaa cagagggac ctgacagcgg actcggtcca gaggggttcc       480
cgccatggcc tagagcagta cctttccaga ttcgaagaag caatgaagct aaggaaacag       540
ctgattagtg aaaaacccag tcaagaggat ggaaatacaa cagaagaatt tgactctttt       600
cgaatattta gattggtggg atgtgctctt cttgctcttg gagtcagagc ttttgtttgc       660
aaatacttgt ccatatttgc tccatttctt actttacaac ttgcgtacat gggattatac       720
aaatattttc ccaagagtga aaagaagata aagacaacag tactaacagc tgcacttcta       780
ttgtcgggaa ttcctgccga agtgataaat cgatcaatgg ataccctatag caaaatgggc       840
```

```
gaagtcttca cagatctctg tgtctacttt ttcactttta tcttttgtca tgaactgctt    900
gattattggg gctctgaagt accatgaagc ctgtagaact gagaaggaga agcttacgaa    960
aaaaatcctc ttctatattg cagtgtctct aaaggaggca aattggttta caccttcatg   1020
taattctttt actttagggg ttgtaaagct actttattag atatagaatg gcagattctc   1080
tgatttaaaa gggctgagtt tgtattatta ctgatatgaa gaatagagta ccaatgtcat   1140
taattgattt tcttgttaa tcagaattcc tattctgtac ctttcctcta acttctcaga    1200
tttgtaattc ttcttttcgg gagctgagct agtgctttta ggagaacaga taaatgtggt   1260
ctcagccagc cctagagact gcttcttgtg tttgtgtcat tctgtcctga gaaatgaagt   1320
catctgaaaa ataaaaatgc agaaacccaa                                    1350
```

<210> SEQ ID NO 6
<211> LENGTH: 25
<212> TYPE: PRT
<213> ORGANISM: Artificial polypeptide
<220> FEATURE:
<223> OTHER INFORMATION: spacer sequence

<400> SEQUENCE: 6

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 7
<211> LENGTH: 8
<212> TYPE: PRT
<213> ORGANISM: Artificial polypeptide
<220> FEATURE:
<223> OTHER INFORMATION: His Tag

<400> SEQUENCE: 7

His His His His His His His His
1               5

<210> SEQ ID NO 8
<211> LENGTH: 19
<212> TYPE: DNA
<213> ORGANISM: Artificial Sequence
<220> FEATURE:
<223> OTHER INFORMATION: Primer Sequence

<400> SEQUENCE: 8
ccagctgcac tgaatccac                                                  19

<210> SEQ ID NO 9
<211> LENGTH: 19
<212> TYPE: DNA
<213> ORGANISM: Artificial Sequence
<220> FEATURE:
<223> OTHER INFORMATION: Primer Sequence

<400> SEQUENCE: 9
gcctgaaccc aacttggag                                                  19

<210> SEQ ID NO 10
<211> LENGTH: 30
<212> TYPE: DNA
<213> ORGANISM: Artificial Sequence
<220> FEATURE:
<223> OTHER INFORMATION: Probe Sequence

<400> SEQUENCE: 10
cttctgtaca taccgattct gtgacgagcc                                30

<210> SEQ ID NO 11
<211> LENGTH: 19
<212> TYPE: DNA
<213> ORGANISM: Artificial Sequence
<220> FEATURE:
<223> OTHER INFORMATION: Primer Sequence

<400> SEQUENCE: 11
tgaaggtcgg tgtgaacgg                                            19

<210> SEQ ID NO 12
<211> LENGTH: 24
<212> TYPE: DNA
<213> ORGANISM: Artificial Sequence
<220> FEATURE:
<223> OTHER INFORMATION: Primer Sequence

<400> SEQUENCE: 12
ccatgtagtt gaggtcaatg aagg                                      24

<210> SEQ ID NO 13
<211> LENGTH: 24
<212> TYPE: DNA
<213> ORGANISM: Artificial Sequence
<220> FEATURE:
<223> OTHER INFORMATION: Probe Sequence

<400> SEQUENCE: 13
tggtcaccag ggctgccatt tgca                                      24

<210> SEQ ID NO 14
<211> LENGTH: 23
<212> TYPE: DNA
<213> ORGANISM: Artificial Sequence
<220> FEATURE:
<223> OTHER INFORMATION: Primer Sequence

<400> SEQUENCE: 14
cgtaccacta ctgatctcga agc                                       23

<210> SEQ ID NO 15
<211> LENGTH: 23
<212> TYPE: DNA
<213> ORGANISM: Artificial Sequence
<220> FEATURE:
<223> OTHER INFORMATION: Primer Sequence

<400> SEQUENCE: 15
ctgtggtcca ggaacatgta atg                                       23

<210> SEQ ID NO 16
<211> LENGTH: 30
<212> TYPE: DNA
<213> ORGANISM: Artificial Sequence
<220> FEATURE:
<223> OTHER INFORMATION: Probe Sequence

<400> SEQUENCE: 16
cttctgtaca taccgattct gtgacgagcc                                30

<210> SEQ ID NO 17

<211> LENGTH: 480
<212> TYPE: PRT
<213> ORGANISM: Artificial polypeptide
<220> FEATURE:
<223> OTHER INFORMATION: SITH1-CAML fusion protein

<400> SEQUENCE: 17

```
Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ile Thr Met
            20                  25                  30

Leu Thr Leu Glu Ile Ile Ser Asn Gln Lys Arg Thr Thr Asp Leu
        35                  40                  45

Glu Ala Val Thr Val Ala Leu Lys His Val Ser Thr Ser Leu Ala Ser
    50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
            100                 105                 110

Cys Ile Met Met Ile Phe Ile Thr Cys Ser Trp Thr Thr Glu Lys Asp
            115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val Gly
145                 150                 155                 160

Gly Gly Gly Ser Gly Gly Gly Gly Ser Gly Gly Gly Ser Gly Gly
                165                 170                 175

Gly Gly Ser Gly Gly Gly Ser Met Glu Ser Met Ala Val Ala Thr
            180                 185                 190

Asp Gly Gly Glu Arg Pro Gly Val Pro Ala Gly Ser Gly Leu Ser Ala
        195                 200                 205

Ser Gln Arg Arg Ala Glu Leu Arg Arg Lys Leu Leu Met Asn Ser
210                 215                 220

Glu Gln Arg Ile Asn Arg Ile Met Gly Phe His Arg Pro Gly Ser Gly
225                 230                 235                 240

Ala Glu Glu Glu Ser Gln Thr Lys Ser Lys Gln Gln Asp Ser Asp Lys
                245                 250                 255

Leu Asn Ser Leu Ser Val Pro Ser Val Ser Lys Arg Val Val Leu Gly
            260                 265                 270

Asp Ser Val Ser Thr Gly Thr Thr Asp Gln Gln Gly Gly Val Ala Glu
        275                 280                 285

Val Lys Gly Thr Gln Leu Gly Asp Lys Leu Asp Ser Phe Ile Lys Pro
    290                 295                 300

Pro Glu Cys Ser Ser Asp Val Asn Leu Glu Leu Arg Gln Arg Asn Arg
305                 310                 315                 320

Gly Asp Leu Thr Ala Asp Ser Val Gln Arg Gly Ser Arg His Gly Leu
                325                 330                 335

Glu Gln Tyr Leu Ser Arg Phe Glu Glu Ala Met Lys Leu Arg Lys Gln
            340                 345                 350

Leu Ile Ser Glu Lys Pro Ser Gln Gly Asp Gly Asn Thr Thr Glu Glu
        355                 360                 365

Phe Asp Ser Phe Arg Ile Phe Arg Leu Val Gly Cys Ala Leu Leu Ala
    370                 375                 380
```

```
Leu Gly Val Arg Ala Phe Val Cys Lys Tyr Leu Ser Ile Phe Ala Pro
385                 390                 395                 400

Phe Leu Thr Leu Gln Leu Ala Tyr Met Gly Leu Tyr Lys Tyr Phe Pro
            405                 410                 415

Lys Ser Glu Lys Lys Ile Lys Thr Thr Val Leu Thr Ala Ala Leu Leu
        420                 425                 430

Leu Ser Gly Ile Pro Ala Glu Val Ile Asn Arg Ser Met Asp Thr Tyr
        435                 440                 445

Ser Lys Met Gly Glu Val Phe Thr Asp Leu Cys Val Tyr Phe Phe Thr
    450                 455                 460

Phe Ile Phe Cys His Glu Leu Leu Asp Tyr Trp Gly Ser Glu Val Pro
465                 470                 475                 480
```

<210> SEQ ID NO 18
<211> LENGTH: 485
<212> TYPE: PRT
<213> ORGANISM: Artificial polypeptide
<220> FEATURE:
<223> OTHER INFORMATION: CAML-SITH1 fusion protein

<400> SEQUENCE: 18

```
Met Glu Ser Met Ala Val Ala Thr Asp Gly Gly Glu Arg Pro Gly Val
1               5                   10                  15

Pro Ala Gly Ser Gly Leu Ser Ala Ser Gln Arg Arg Ala Glu Leu Arg
            20                  25                  30

Arg Arg Lys Leu Leu Met Asn Ser Glu Gln Arg Ile Asn Arg Ile Met
        35                  40                  45

Gly Phe His Arg Pro Gly Ser Gly Ala Glu Glu Ser Gln Thr Lys
50                  55                  60

Ser Lys Gln Gln Asp Ser Asp Lys Leu Asn Ser Leu Ser Val Pro Ser
65                  70                  75                  80

Val Ser Lys Arg Val Leu Gly Asp Ser Val Ser Thr Gly Thr Thr
                85                  90                  95

Asp Gln Gln Gly Gly Val Ala Glu Val Lys Gly Thr Gln Leu Gly Asp
            100                 105                 110

Lys Leu Asp Ser Phe Ile Lys Pro Pro Glu Cys Ser Ser Asp Val Asn
        115                 120                 125

Leu Glu Leu Arg Gln Arg Asn Arg Gly Asp Leu Thr Ala Asp Ser Val
    130                 135                 140

Gln Arg Gly Ser Arg His Gly Leu Glu Gln Tyr Leu Ser Arg Phe Glu
145                 150                 155                 160

Glu Ala Met Lys Leu Arg Lys Gln Leu Ile Ser Glu Lys Pro Ser Gln
                165                 170                 175

Glu Asp Gly Asn Thr Thr Glu Glu Phe Asp Ser Phe Arg Ile Phe Arg
            180                 185                 190

Leu Val Gly Cys Ala Leu Leu Ala Leu Gly Val Arg Ala Phe Val Cys
        195                 200                 205

Lys Tyr Leu Ser Ile Phe Ala Pro Phe Leu Thr Leu Gln Leu Ala Tyr
    210                 215                 220

Met Gly Leu Tyr Lys Tyr Phe Pro Lys Ser Glu Lys Lys Ile Lys Thr
225                 230                 235                 240

Thr Val Leu Thr Ala Ala Leu Leu Leu Ser Gly Ile Pro Ala Glu Val
                245                 250                 255

Ile Asn Arg Ser Met Asp Thr Tyr Ser Lys Met Gly Glu Val Phe Thr
            260                 265                 270
```

```
Asp Leu Cys Val Tyr Phe Phe Thr Phe Ile Phe Cys His Glu Leu Leu
        275                 280                 285

Asp Tyr Trp Gly Ser Glu Val Pro Arg Ser Gly Gly Gly Ser Gly
        290                 295                 300

Gly Gly Gly Ser Gly Gly Gly Gly Ser Gly Gly Gly Ser Gly Gly
305                 310                 315                 320

Gly Gly Ser Leu Gln Thr Met Gly Tyr Glu Glu Lys Val Ser Ala Thr
            325                 330                 335

Gly Lys Thr Arg Leu Lys Ile Leu Ala Cys Leu Ile Val Leu Ile Leu
            340                 345                 350

Ala Ala Ala Ile Thr Met Leu Thr Leu Glu Ile Ile Ser Asn Gln Lys
        355                 360                 365

Arg Thr Thr Thr Asp Leu Glu Ala Val Thr Val Ala Leu Lys His Val
    370                 375                 380

Ser Thr Ser Leu Ala Ser Cys Thr Glu Ser Thr Thr Ser Val His Thr
385                 390                 395                 400

Asp Ser Val Thr Ser Gln Pro Thr Lys Asn Lys Glu Ser Arg Lys Lys
                405                 410                 415

Ile Glu Gly Lys Ser Pro Ser Trp Val Gln Ala Leu Thr Thr Ala Ser
            420                 425                 430

Gly Ile Ile Leu Leu Phe Cys Ile Met Met Ile Phe Ile Thr Cys Ser
        435                 440                 445

Trp Thr Thr Glu Lys Asp Thr Glu Lys Ser Glu Val Gln Ser Tyr Ala
    450                 455                 460

Ser Ser Val Glu Thr Leu Asp Ser Leu Asn Glu Ala Ile Ile Pro Lys
465                 470                 475                 480

Thr Glu Met Asn Val
            485

<210> SEQ ID NO 19
<211> LENGTH: 1440
<212> TYPE: DNA
<213> ORGANISM: Artificial sequence
<220> FEATURE:
<223> OTHER INFORMATION: nucleotide sequence of SITH1-CAML fusion
      protein

<400> SEQUENCE: 19
atgggctatg aggagaaggt cagcgccacc ggcaaaacca gactgaagat cctcgcttgc      60
ctcatcgtgc tgattctggc cgctgccatc accatgctga cactggagat catcagcaac     120
caaaagagga ccaccaccga cctggaagct gtcacagtgg ctctgaagca cgtgagcaca     180
agcctggcct cctgcaccga agcaccacc agcgtgcaca ccgacagcgt gacctcccag     240
cccaccaaga caaagaatc aggaagaaa attgagggca gtccccttc ctgggtgcaa      300 gccctcacca ccgccagcgg aatcatcctg ctgttctgca tcatgatgat tttcattacc      360
tgttcctgga ccacagagaa ggacaccgag aaatccgagg tgcagtccta cgcctccagc      420
gtggagaccc tcgactccct gaacgaggcc attatcccca aaaccgagat gaacgtggga      480
ggcggcggaa gcgaggagg cggctccggc ggcggcggct ccggcggcgg aggctccggc      540
ggcggcggca gcatggaaag catggccgtg ccaccgatg gcggagaaag acctggagtc      600
cctgctggat ccggcctgtc cgcttcccag aggagggccg agctgaggag gaggaagctg      660
ctcatgaaca gcgagcagag gatcaacagg atcatgggct ccacaggcc tgcagcgga      720 gccgaagagg agtcccagac caagagcaag cagcaggata gcgacaaact caacagcctg      780
```

```
tccgtgcctt ccgtgagcaa gagagtggtg ctgggcgaca gcgtgagcac aggaaccacc      840
gatcaacagg gcggcgtggc cgaggtcaaa ggaacccagc tgggcgataa gctggacagc      900
tttatcaagc ccccgagtg cagcagcgac gtcaatctgg agctgaggca gaggaataga      960
ggcgatctga ccgctgatag cgtccagaga ggctccagac atggactgga acagtacctc     1020
agcaggttcg aggaagccat gaagctgagg aagcagctga tcagcgagaa gccctcccag     1080
gaggacggca atacaaccga ggagttcgac tccttcagga tcttcaggct ggtcggctgt     1140
gctctgctgg ctctgggcgt gagggccttc gtgtgcaagt acctgtccat tttcgccccc     1200
tttctcaccc tccagctggc ctacatgggc ctgtacaagt atttccccaa aagcgagaaa     1260
aagatcaaga caaccgtgct caccgctgct ctgctcctga gcggcattcc cgccgaggtg     1320
atcaacaggt ccatggacac ctattccaag atgggcgagg tgttcacaga cctgtgcgtg     1380
tatttcttta ccttcatctt ctgccacgag ctgctggact actggggctc cgaggtgccc     1440
```

<210> SEQ ID NO 20
<211> LENGTH: 1455
<212> TYPE: DNA
<213> ORGANISM: Artificial sequence
<220> FEATURE:
<223> OTHER INFORMATION: nucleotide sequence of CAML-SITH1 fusion
      protein

<400> SEQUENCE: 20

```
atggaaagca tggccgtggc caccgatggc ggagaaagac ctggagtccc tgctggttcc       60
ggcctgtccg cttcccagag gagggccgag ctgaggagga ggaagctgct catgaacagc      120
gagcagagga tcaacaggat catgggcttc acaggcctg gcagcggagc cgaagaggag       180
tcccagacca gagcaagca gcaggatagc gacaaactca cagcctgtc cgtgccttcc        240 gtgagcaaga gagtggtgct gggcgacagc gtgagcacag gaaccaccga tcaacagggc     300
ggcgtggccg aggtcaaagg aacccagctg gcgataagc tggacagctt tatcaagccc       360
cccgagtgca gcagcgacgt caatctggag ctgaggcaga ggaatagagg cgatctgacc     420
gctgatagcg tccagagagg ctccagacat ggactggaac agtacctcag caggttcgag     480
gaagccatga agctgaggaa gcagctgatc agcgagaagc cctcccagga ggacggcaat     540
acaaccgagg agttcgactc cttcaggatc ttcaggctgg tcggctgtgc tctgctggct    600
ctgggcgtga gggccttcgt gtgcaagtac ctgtccattt tcgccccctt tctcaccctc     660
cagctggcct acatgggcct gtacaagtat tccccaaaa gcgagaaaaa gatcaagaca      720
accgtgctca ccgctgctct gctcctgagc ggcattcccg ccgaggtgat caacaggtcc    780
atggacacct attccaagat gggcgaggtg ttcacagacc tgtgcgtgta tttctttacc    840
ttcatcttct gccacgagct gctggactac tggggctccg aggtgcccag atctggaggc   900
ggtgggagcg gaggaggtgg gtctggcggt ggcgggtccg gaggcggcgg tcaggcggc    960 ggagggagtc tgcagaccat gggctatgag gagaaggtca cgccaccgg caaaaccaga    1020 ctgaagatcc tcgcttgcct catcgtgctg attctggccg ctgccatcac catgctgaca    1080
ctggagatca tcagcaacca aaagaggacc accaccgacc tggaagctgt cacagtggct    1140
ctgaagcacg tgagcacaag cctggcctcc tgcaccgaaa gcaccaccag cgtgcacacc    1200
gacagcgtga cctcccagcc caccaagaac aaagaatcca ggaagaaaat tgagggcaag    1260
tccccttcct gggtgcaagc cctcaccacc gccagcggaa tcatcctgct gttctgcatc    1320
atgatgattt tcattaccctg ttcctggacc acagagaagg acaccgagaa atccgaggtg   1380
```
cagtcctacg cctccagcgt ggagaccctc gactccctga acgaggccat tatccccaaa    1440
accgagatga acgtg                                                     1455

<210> SEQ ID NO 21
<211> LENGTH: 304
<212> TYPE: PRT
<213> ORGANISM: Artificial polypeptide
<220> FEATURE:
<223> OTHER INFORMATION: CAML-His fusion protein

<400> SEQUENCE: 21

Met Glu Ser Met Ala Val Ala Thr Asp Gly Gly Glu Arg Pro Gly Val
1               5                   10                  15

Pro Ala Gly Ser Gly Leu Ser Ala Ser Gln Arg Arg Ala Glu Leu Arg
            20                  25                  30

Arg Arg Lys Leu Leu Met Asn Ser Glu Gln Arg Ile Asn Arg Ile Met
        35                  40                  45

Gly Phe His Arg Pro Gly Ser Gly Ala Glu Glu Ser Gln Thr Lys
    50                  55                  60

Ser Lys Gln Gln Asp Ser Asp Lys Leu Asn Ser Leu Ser Val Pro Ser
65                  70                  75                  80

Val Ser Lys Arg Val Val Leu Gly Asp Ser Val Ser Thr Gly Thr Thr
                85                  90                  95

Asp Gln Gln Gly Gly Val Ala Glu Val Lys Gly Thr Gln Leu Gly Asp
            100                 105                 110

Lys Leu Asp Ser Phe Ile Lys Pro Pro Glu Cys Ser Ser Asp Val Asn
        115                 120                 125

Leu Glu Leu Arg Gln Arg Asn Arg Gly Asp Leu Thr Ala Asp Ser Val
    130                 135                 140

Gln Arg Gly Ser Arg His Gly Leu Glu Gln Tyr Leu Ser Arg Phe Glu
145                 150                 155                 160

Glu Ala Met Lys Leu Arg Lys Gln Leu Ile Ser Glu Lys Pro Ser Gln
                165                 170                 175

Glu Asp Gly Asn Thr Thr Glu Glu Phe Asp Ser Phe Arg Ile Phe Arg
            180                 185                 190

Leu Val Gly Cys Ala Leu Leu Ala Leu Gly Val Arg Ala Phe Val Cys
        195                 200                 205

Lys Tyr Leu Ser Ile Phe Ala Pro Phe Leu Thr Leu Gln Leu Ala Tyr
    210                 215                 220

Met Gly Leu Tyr Lys Tyr Phe Pro Lys Ser Glu Lys Lys Ile Lys Thr
225                 230                 235                 240

Thr Val Leu Thr Ala Ala Leu Leu Ser Gly Ile Pro Ala Glu Val
                245                 250                 255

Ile Asn Arg Ser Met Asp Thr Tyr Ser Lys Met Gly Glu Val Phe Thr
            260                 265                 270

Asp Leu Cys Val Tyr Phe Phe Thr Phe Ile Phe Cys His Glu Leu Leu
        275                 280                 285

Asp Tyr Trp Gly Ser Glu Val Pro His His His His His His
    290                 295                 300

<210> SEQ ID NO 22
<211> LENGTH: 891
<212> TYPE: DNA
<213> ORGANISM: Homo sapiens

<400> SEQUENCE: 22

```
atggagtcga tggccgtcgc taccgacggc ggggagaggc cgggggtccc agcgggctca      60
ggtctgtcgg cttcccagcg tcgggcggag ctgcgtcgga gaaagctgct catgaactcg     120
gaacagcgca tcaaccggat catgggcttt cacaggcccg ggagcggcgc ggaagaagaa     180
agtcaaacaa aatcaaagca gcaggacagt gataaactga actccctcag cgttccttcc     240
gtttcaaagc gagtagtgct gggtgattca gtcagtacag gaacaactga ccagcagggt     300
ggtgtggccg aggtaaaggg gacccaactg ggagacaaat tggactcgtt cattaaacca     360
cctgagtgca gtagtgatgt caaccttgag ctccggcagc ggaacagagg ggacctgaca     420
gcggactcgg tccagagggg ttcccgccat ggcctagagc agtaccttc cagattcgaa      480 gaagcaatga agctaaggaa acagctgatt agtgaaaaac ccagtcaaga ggatggaaat     540
acaacagaag aatttgactc ttttcgaata tttagattgg tgggatgtgc tcttcttgct     600
cttggagtca gagcttttgt ttgcaaatac ttgtccatat ttgctccatt tcttacttta     660
caacttgcgt acatgggatt atacaaatat tttcccaaga gtgaaaagaa gataaagaca     720
acagtactaa cagctgcact tctattgtcg ggaattcctg ccgaagtgat aaatcgatca     780
atggatacct atagcaaaat gggcgaagtc ttcacagatc tctgtgtcta cttttttcact    840 tttatctttt gtcatgaact gcttgattat tggggctctg aagtaccatg a              891
```